US012774283B2

(12) United States Patent
Gandla et al.

(10) Patent No.: US 12,774,283 B2
(45) Date of Patent: Oct. 27, 2026

(54) POLYMORPHS OF A $GABA_A$ α5 AGONIST AND METHODS OF USING IN THE TREATMENT OF COGNITIVE IMPAIRMENT

(71) Applicant: AGENEBIO, INC., Baltimore, MD (US)

(72) Inventors: Deepa Gandla, Albany, NY (US); Brian Gregg, Albany, NY (US); Vishnumurthy Hegde, Glen Mills, PA (US); Stephan D. Parent, West Lafayette, IN (US); Travis Lee Houston, Lafayette, IN (US)

(73) Assignee: AGENEBIO, INC., Baltimore, MD (US)

( * ) Notice: Subject to any disclaimer, the term of this patent is extended or adjusted under 35 U.S.C. 154(b) by 783 days.

(21) Appl. No.: 18/015,445

(22) PCT Filed: Jul. 9, 2021

(86) PCT No.: PCT/US2021/041179
§ 371 (c)(1),
(2) Date: Jan. 10, 2023

(87) PCT Pub. No.: WO2022/011314
PCT Pub. Date: Jan. 13, 2022

(65) Prior Publication Data

US 2023/0279021 A1 Sep. 7, 2023

Related U.S. Application Data

(60) Provisional application No. 63/050,642, filed on Jul. 10, 2020.

(51) Int. Cl.
*C07D 487/14* (2006.01)
*A61K 31/13* (2006.01)
*A61K 31/5517* (2006.01)
*A61K 45/06* (2006.01)

(52) U.S. Cl.
CPC ............ *C07D 487/14* (2013.01); *A61K 31/13* (2013.01); *A61K 31/5517* (2013.01); *A61K 45/06* (2013.01)

(58) Field of Classification Search
CPC .... A61K 31/13; A61K 31/5517; A61K 45/06; A61P 25/16; A61P 25/18; A61P 25/28; C07D 487/14
See application file for complete search history.

(56) References Cited

U.S. PATENT DOCUMENTS

| | | | |
|---|---|---|---|
| 3,391,142 | A | 7/1968 | Jack et al. |
| 3,539,573 | A | 11/1970 | Schmutz et al. |
| 4,122,193 | A | 10/1978 | Scherm et al. |
| 4,145,434 | A | 3/1979 | Van Der Burg |
| 4,273,774 | A | 6/1981 | Scherm |
| 4,710,500 | A | 12/1987 | Perregaard |
| 4,734,416 | A | 3/1988 | Banno et al. |
| 4,804,663 | A | 2/1989 | Kennis et al. |
| 4,816,456 | A | 3/1989 | Summers |
| 4,831,031 | A | 5/1989 | Lowe et al. |
| 4,879,288 | A | 11/1989 | Warawa et al. |
| 4,895,841 | A | 1/1990 | Sugimoto et al. |
| 5,006,528 | A | 4/1991 | Oshiro et al. |
| 5,041,455 | A | 8/1991 | Sauerberg et al. |
| 5,061,703 | A | 10/1991 | Bormann et al. |
| 5,106,856 | A | 4/1992 | Kosley et al. |
| 5,229,382 | A | 7/1993 | Chakrabarti et al. |
| 5,312,925 | A | 5/1994 | Allen et al. |
| 5,387,585 | A | 2/1995 | Borer et al. |
| 5,500,438 | A | 3/1996 | Barnette et al. |
| 5,532,372 | A | 7/1996 | Saji et al. |
| 5,552,409 | A | 9/1996 | Michelotti et al. |
| 5,602,176 | A | 2/1997 | Enz |
| 5,763,476 | A | 6/1998 | Delbressine et al. |
| 6,677,330 | B1 | 1/2004 | Iimura et al. |
| 6,689,816 | B2 | 2/2004 | Fogel |
| 6,743,789 | B2 | 6/2004 | Masciadri et al. |
| 7,340,299 | B2 | 3/2008 | Puskas |
| 7,381,725 | B2 | 6/2008 | Fletcher et al. |

(Continued)

FOREIGN PATENT DOCUMENTS

| | | |
|---|---|---|
| CN | 108567786 A | 9/2018 |
| CN | 108567787 A | 9/2018 |

(Continued)

OTHER PUBLICATIONS

Giron, "Thermal analysis and calorimetric methods in the characterization of polymorphs and solvates", Thirmochimica Acta, 248, 1-59 (Year: 2019).*
Thomaes et al., "Increased activation of the left hippocampus region in Complex PTSD during encoding and recognition of emotional words: A pilot study," Psychiatry Research: Neuroimaging 171 (2009) 44-53.
Tozzi et al., "[Levetiracetam in children and adolescents: Generalised vs partial seizures]," Bollellino-Lega Italiana contro l'Epilessia, 133-134:257-258 (2006) (English Abstract only).
Tremolizzo et al., "An epigenetic mouse model for molecular and behavioral neuropathologies related to schizophrenia vulnerability," PNAS, 2002, 99(26): 17095-17100.

(Continued)

*Primary Examiner* — Jeffrey H Murray
*Assistant Examiner* — Daniel John Burkett
(74) *Attorney, Agent, or Firm* — Leason Ellis LLP; James F. Haley, Jr.; Marcus J. Jellen

(57) ABSTRACT

Crystalline forms of a $GABA_A$ α5 agonist, pharmaceutical compositions and combinations comprising those crystalline forms, their use in methods of treating cognitive impairment associated with central nervous system (CNS) disorders, cognitive impairment associated with brain cancer, the brain cancer itself or Parkinson's disease psychosis and methods of producing the crystalline forms.

8 Claims, 21 Drawing Sheets

(56) References Cited

U.S. PATENT DOCUMENTS

| | | | |
|---|---|---|---|
| 7,432,256 | B2 | 10/2008 | Uettelmann et al. |
| 7,498,361 | B2 | 3/2009 | Fogel |
| 7,507,728 | B2 | 3/2009 | Knust et al. |
| 7,635,709 | B2 | 12/2009 | Korsten et al. |
| 7,642,267 | B2 | 1/2010 | Li et al. |
| 7,671,048 | B2 | 3/2010 | Knust et al. |
| 8,058,268 | B2 | 11/2011 | Kovach |
| 8,510,055 | B2 | 8/2013 | Gallagher et al. |
| 8,741,808 | B2 | 6/2014 | Li et al. |
| 8,835,425 | B2 | 9/2014 | Gasset et al. |
| 8,853,219 | B2 | 10/2014 | Hendrickson et al. |
| 9,145,372 | B2 | 9/2015 | Lowe, III |
| 9,801,879 | B2 | 10/2017 | Lowe, III |
| 10,329,301 | B2 | 6/2019 | Mekonnen et al. |
| 10,815,242 | B2 | 10/2020 | Mekonnen et al. |
| 11,142,529 | B2 | 10/2021 | Mekonnen et al. |
| 11,312,721 | B2 | 4/2022 | Mekonnen et al. |
| 11,414,425 | B2 | 8/2022 | Mekonnen et al. |
| 11,505,555 | B2 | 11/2022 | Mekonnen et al. |
| 12,024,525 | B2 | 7/2024 | Mekonnen et al. |
| 2003/0125333 | A1 | 7/2003 | Bryant et al. |
| 2004/0087658 | A1 | 5/2004 | Moebius |
| 2005/0113458 | A1 | 5/2005 | Gupta et al. |
| 2006/0079507 | A1 | 4/2006 | Knust et al. |
| 2006/0084642 | A1 | 4/2006 | Knust et al. |
| 2006/0128691 | A1 | 6/2006 | Buettelmann et al. |
| 2006/0167032 | A1 | 7/2006 | Galer et al. |
| 2006/0205822 | A1 | 9/2006 | Jonas et al. |
| 2006/0235021 | A1 | 10/2006 | Blackaby et al. |
| 2007/0112017 | A1 | 5/2007 | Barlow et al. |
| 2008/0269236 | A1 | 10/2008 | Ji et al. |
| 2009/0081259 | A1 | 3/2009 | Jonas et al. |
| 2009/0124659 | A1 | 5/2009 | Moebius |
| 2009/0143385 | A1 | 6/2009 | Buettelmann et al. |
| 2010/0075954 | A1 | 3/2010 | Knust et al. |
| 2010/0081648 | A1 | 4/2010 | Gallagher et al. |
| 2010/0081723 | A1 | 4/2010 | Jonas et al. |
| 2010/0099735 | A1 | 4/2010 | Gallagher et al. |
| 2010/0227852 | A1 | 9/2010 | Moebius |
| 2011/0212928 | A1 | 9/2011 | Gallagher et al. |
| 2012/0035139 | A9 | 2/2012 | Xu et al. |
| 2012/0046336 | A1 | 2/2012 | Gallagher et al. |
| 2012/0214859 | A1 | 8/2012 | Gallagher et al. |
| 2013/0150351 | A1 | 6/2013 | Carmichael et al. |
| 2013/0237530 | A1 | 9/2013 | Lowe, III |
| 2014/0057903 | A1 | 2/2014 | Gallagher et al. |
| 2015/0374705 | A1 | 12/2015 | Zhang et al. |
| 2016/0008357 | A1 | 1/2016 | Lowe, III |
| 2017/0022208 | A1 | 1/2017 | Mekonnen et al. |
| 2018/0010183 | A1 | 1/2018 | Gallagher et al. |
| 2018/0170941 | A1 | 6/2018 | Mekonnen et al. |
| 2019/0055258 | A1 | 2/2019 | Mekonnen et al. |
| 2019/0284196 | A1 | 9/2019 | Mekonnen et al. |
| 2020/0048268 | A1 | 2/2020 | Mekonnen et al. |
| 2021/0009602 | A1 | 1/2021 | Mekonnen et al. |
| 2021/0253588 | A1 | 8/2021 | Mekonnen et al. |
| 2022/0062296 | A1 | 3/2022 | Gallagher et al. |
| 2022/0274996 | A1 | 9/2022 | Mekonnen et al. |
| 2023/0098667 | A1 | 3/2023 | Mekonnen et al. |
| 2023/0270753 | A1 | 8/2023 | Gallagher et al. |
| 2024/0132513 | A1 | 4/2024 | Mekonnen et al. |

FOREIGN PATENT DOCUMENTS

| | | | | |
|---|---|---|---|---|
| EP | 0368388 | A2 | 5/1990 | |
| EP | 0402644 | A1 | 12/1990 | |
| EP | 0468187 | A2 | 1/1992 | |
| EP | 0481429 | A2 | 4/1992 | |
| EP | 1682109 | B1 | 10/2008 | |
| EP | 2260839 | A2 | 12/2010 | |
| GB | 2352630 | A | 2/2001 | |
| GB | 2352631 | A | 2/2001 | |
| GB | 2352632 | A | 2/2001 | |
| WO | 99/25353 | A1 | 5/1999 | |
| WO | 00/27849 | A2 | 5/2000 | |
| WO | 01/62726 | A2 | 8/2001 | |
| WO | 02/32412 | A2 | 4/2002 | |
| WO | 02/40487 | A2 | 5/2002 | |
| WO | 02/69948 | A1 | 9/2002 | |
| WO | 02/94834 | A1 | 11/2002 | |
| WO | 03/25122 | A2 | 3/2003 | |
| WO | 2004/014865 | A1 | 2/2004 | |
| WO | 2004/014891 | A1 | 2/2004 | |
| WO | 2004/048551 | A2 | 6/2004 | |
| WO | 2005/079779 | A1 | 9/2005 | |
| WO | 2006/045429 | A1 | 5/2006 | |
| WO | 2006/063708 | A1 | 6/2006 | |
| WO | 2007/018660 | A2 | 2/2007 | |
| WO | 2007/019312 | A2 | 2/2007 | |
| WO | 2007/042421 | A1 | 4/2007 | |
| WO | 2009/071477 | A1 | 6/2009 | |
| WO | 2010/036553 | A1 | 4/2010 | |
| WO | 2011/100373 | A1 | 8/2011 | |
| WO | 2011/153377 | A2 | 12/2011 | |
| WO | 2012/059482 | A1 | 5/2012 | |
| WO | 2012/068149 | A1 | 5/2012 | |
| WO | 2012/068161 | A1 | 5/2012 | |
| WO | 2012/161133 | A1 | 11/2012 | |
| WO | 2014/039920 | A1 | 3/2014 | |
| WO | 2014/078568 | A1 | 5/2014 | |
| WO | 2015/095783 | A1 | 6/2015 | |
| WO | 2016/191288 | A1 | 12/2016 | |
| WO | 2016/205739 | A1 | 12/2016 | |
| WO | 2018/130868 | A1 | 7/2018 | |
| WO | 2018/130869 | A1 | 7/2018 | |
| WO | WO-2019246300 | A1 * | 12/2019 | ............. A61K 45/06 |
| WO | 2021/127543 | A1 | 6/2021 | |

OTHER PUBLICATIONS

Van Niel et al., "A new pyridazine series of GABA.sub.A .alpha.5 ligands", J. Med. Chem., 48: 6004-6011 (2005).

Van Spronsen et al., "Synapse pathology in psychiatric and neurologic disease," Current Neurology and Neuroscience Reports, 10(3):207-214 (2010).

Vecht et al., "Seizures in low- and high-grade gliomas: current management and future outlook," Expert Review Anticancer Therapy, 10(5):663-669 (2010).

Verloes et al., "Effects of nootropic drugs in a scopolamine-induced amnesia model in mice," Psychopharmacology, 95(2):226-230 (1988).

Vinkers et al., The inhibitory GABA system as a therapeutic target for cognitive symptoms in schizophrenia: investigational agents in the pipeline, Expert Opinion on Investigational Drugs, 19(10):1217-1233 (2009).

Volk et al., "Decreased Glutamic Acid Decarboxylase.sub.67 Messenger RNA Expression in a Subset of Prefrontal Cortical .gamma.-Aminobutyric Acid Neurons in Subjects With Schizophrenia," Arch Gen Psychiatry, 2000, 57: 237-245.

Von Rosenstiel, "Brivaracetam (UCB 34714)," Neurotherapeutics: The Journal of the American Society for Experimental Neuro Therapeutics, 84-87 (2007).

Waegemans et al., "Clinical efficacy of piracetam in cognitive impairment: a meta-analysis," Dement. Geriatr. Cogn. Disord., 13(4):217-224 (2002).

Walsh et al., "Ionic currents in cultured rat suprachiasmalic neurons," Neuroscience, 69:915-929 (1995).

Wang et al., "Magnetic resonance imaging of hippocampal subfields in posttraumatic stress disorder," Archives of General Psychiatry, 67(3):296-30 (2010).

Whitehouse et al., "Alzheime s disease and senile dementia: loss of neurons in the basal forebrain," Science, 215:1237-39 (1982).

Wilby et al., "Clinical effectiveness, tolerability and cost-effectiveness of newer drugs for epilepsy in adults: a systematic review and economic evaluation," Health Technology Assessment, Executive Summary—Newer drugs for epilepsy in adult, 9(15) (2005).

Wilson et al. "Age associated alterations of hippocampal place cells are subregion specific," J. Neuroscience (2005) 25(29): 6877-6886.

(56) References Cited

OTHER PUBLICATIONS

Wilson et al., "Cognitive Aging and the Hippocampus: How Old Rais Represent New Environments," J. Neurosci., 2004, 24(15): 3870-3878.
Wilson et al., "Place cell rigidity correlates with impaired spatial learning in aged rats," Neurobiology of Aging, 2003, 24: 297-305.
Winblad et al., "Mild cognitive impairment—beyond controversies, towards a consensus: report of the International Working Group on Mild Cognitive Impairment," Journal of Internal Medicine, 2004, 256: 240-246.
Wisden et al., "The Distribution of 13 GABA.sub.A Receptor Subunit mRNAs in the Rat Brain. I. Telencephalon, Diencephalon, Mesencephalon," The Journal of Neuroscience, Mar. 1992, 12(3): 1040-1062.
Wishart et al., "Increased Brain Activation During Working Memory in Cognitively Intact Adults With the APOE c:4 Allele," Am J Psychiatry, 2006, 163: 1603-1610.
Wolthuis, "Experiments with UCB 6215, a drug which enhances acquisition in rats: its effects compared with those of metamphetamine," Eur. J. Pharmacol., 16(3):283-297 (1971).
Wood et al., "Hippocampal pathology in individuals at ultra-high risk for psychosis: a multi-modal magnetic resonance study," NeuroImage 52(1):62-68 (2010).
Woon et al., "Hippocampal volume deficits associated with exposure to psychological trauma and posttraumatic stress disorder in adults: A meta-analysis," Progress in Neuro-Psychopharmacology & Biological Psychiatry 34 (2010) 1181-1188.
Wu et al., "A Model Based Background Adjustment for Oligonucleotide Expression Arrays," Journal of American Statistical Association, 99:909-917 (2004).
Xiang et al., "Stereochemistry as a Tool in Deciphering the Processes of a Tandem Iminium Cyclization and Smiles Rearrangement," Journal of Organic Chemistry, 75(23), 8147-8154 (2010).
Yaffe et al., "Posttraumatic stress disorder and risk of dementia among US veterans," Archives of General Psychiatry, 6(6):608-613 (2010).
Yang et al., "Cyclophosphamide impairs hippocampus-dependent learning and memory in adult mice: Possible involvement of hippocampal neurogenesis in chemotherapy-induced memory deficits," Neurobiology of Leaming and Memory, 93(4):487-494 (2010).
Yassa et al., "Ultrahigh-resolution microstructural diffusion tensor imaging reveals perforant path degradation in aged humans in vivo," PNAS, 107(28):12687-12691 (2010).
Yehuda et al., "Longitudinal assessment of cognitive performance in Holocaust survivors with and without PTSD," Biological Psychiatry, 60(7):714-721 (2006).
Yoon et al., "GABA Concentration Is Reduced in Visual Cortex in Schizophrenia and Correlates with Orientation-Specific Surround Suppression," J. Neurosci., 2010, 30(10): 3777-3781.
Young et al., "Using the MATRICS to guide development of a preclinical cognitive test battery for research in schizophrenia," Pharmacology & Therapeutics, 122(2):150-202 (2009) (5 parts).
Youngjohn et al., "Stability of everyday memory in age-associated memory impairment: A longitudinal study," Neuropsychology, 7(3):406-416 (1993).
Zahodne et al., "Pathophysiology and treatment of psychosis in Parkinson's disease," Drugs Aging. vol. 25, Issue 8, 2008, pp. 665-682.
Zierhut et al., "The role of hippocampus dysfunction in deficient memory encoding and positive symptoms in schizophrenia," Psychiatry Research, 183(3):187-194 (2010).
Kobayashi et al., "Behavioral phenotypes of amyloid-based genetically modified mouse models of Alzheimer's disease," Genes, Brain, and Behavior, 4(3):173-196 (2005).
Koh et al., "Selective GABA(A) a5 positive allosteric modulators improve cognitive function in aged rats with memory impairment. Neuropharmacology," Jan. 2013;64(1 ): 145-52. (Year: 2013).
Koh et al., "Treatment with selective GABA.sub.A .alpha.5 receptor agonists improves cognitive function in aged rats with memory impairment," Society for Neuroscience meeting, Nov. 16, 2010, Handout, 1 page.
Korakas et al., "Synthesis of the novel pyrrolo[2,1-d][1,2,5]benzotriazepine, pyrrolo[2,1-e][1,3,6]benzotriazocine and pyrrolo[1,2-a]tetrazolo[1,5-d][1,4]benzodiazepine ring systems. A new route to pyrrolo[1,2-a]quinoxaline via transamination of in situ generated 1-(2-aminophenyl)-2-iminomethylpyrroles", Tetrahedron, vol. 52, No. 32, 1996, pp. 10751-10760.
Larrabee, "Age-associated memory impairment: Definition and psychometric characteristics," Aging, Neuropsychology, and Cognition, 3(2):118-131 (1996).
Lee et al., "Levetiracetam inhibits glutamate transmission through presynaptic P/Q-type calcium channels on the granule cells of the dentate gyms," British J. Pharmacol., 158:1753-1762 (2009).
Lein et al., "Defining a molecular atlas of the hippocampus using DNA microarrays and high-throughput in situ hybridization," J Neurosci., 24(15):3879-3889 (2004).
Leppik et al., "Extended-release antiepileptic drugs: a comparison of phannacokinetic parameters relative to original immediate-release formulations," Enilepsia, 54(1):28-35 (2013).
Leutgeb et al., "Independent Codes for Spatial and Episodic Memory in Hippocampal Neuronal Ensembles," Science, 2005, 309: 619-623.
Leutgeb et al., "Pattern Separation in the Dentate Gyms and CA3 of the Hippocampus," Science, 2007, 315: 961-966.
Liberzon et al., "Stress-Restress: Effects on ACTH And Fast Feedback," Psvchoneuroendocrinology, 1997, 22(6): 443-453.
Lingford-Hughes et al., "Imaging the GABA-Benzodiazepine Receptor Subtype Containing the a5-SubunilIn Vivo With [11C]Rol5 4513 Positron Emission Tomography," J_ Cereb. Blood Flow Metab, 2002, 22(7): 878-889.
Lippa et al., "Selective anxiolysis produced by ocinaplon, a GABA.sub.A receptor modulator," PNAS 102(20):7380-7385, 2005.
Liu et al., "Synthesis and Pharmacological Properties of Novel 8-Substituted Imidazobenzodiazepines: High-Affinity, Selective Probes for alpha.5-Containing GABA.sub.A Receptors.sup.1," J. Med. Chem., 1996, 39: 1928-1934.
Lodge et al., "Aberrant Hippocampal Activity Underlies the Dopamine Dysregulation in an Animal Model of Schizophrenia," J. Neurosci. (2007), 27(42), 11424-11430.
Lodge, D et al.; A Loss of Parvalbumin-Containing Interneurons Is Associated with Diminished Oscillatory Activity in an Animal Model of Schizophrenia.; J. Neurosci.; 29(8):2344-2354, (2009).
Loscher et al., "Profile of ucb L059, a novel anticonvulsant drug, in models of partial and generalized epilepsy in mice and rats," Eur. J. Pharmacol., 232(2-3):147-158 (1993).
Luciano et al., "Results of treatment changes in patients with apparently drug-resistant chronic epilepsy," Annals of Neurology, 62(4):375-381 (2007).
Lukyanetz et al., "Selective blockade of N-type calcium channels by levetiracetam," Epilepsia, 43(1):9-18 (2002).
Lupien et al., "Effects of stress throughout the lifespan on the brain, behaviour and coe.nition," Nature Review/Neuroscience, Jun. 2009, vol. 10, 434-445.
Maeda et al., "Visualization of .alpha.5 Subunit of GABA.sub.A/ Benzodiazepine Receptor by [.sup.11C]Ro15-4513 Using Positron Emission Tomography," Synapse, 2003, 47: 200-208.
Maggini M, Vanacore N, Raschetti R (2006) Cholinesterase Inhibitors: Drugs Looking for a Disease? PLoS Med 3(4): e140. doi:10.1371/journal.pmed.0030140.
Marini et al., "Placebo-controlled double-blind study of pramiracetam (CI-879) in the treatment of elderly subjects with memory impairment," Advances in Therapy 9(3):136-146 (1992).
Marquis et al., "Independent predictors of cognitive decline in healthy elderly persons," Archives of Neurology, 59:601-606 (2002).
Masur et al., "Neuropsychological prediction of dementia and the absence of dementia in healthy elderly persons" Neurology, vol. 44, Issue 8, 1994, pp. 1427-1432.
Meador et al., "Cognitive and behavioral effects of carbamazepine and levetiracetam in healthy volunteers: S09.002: 2:15 pm," Neurology, 66(S2) p. A72 (2006) (Abstract).

(56) References Cited

OTHER PUBLICATIONS

Meador et al., "Neurocognitive effects of brivaracetam, levetiracetam, and lorazepam," Epilepsia, 52(2):264-272 (2011).
Meador, "Cognitive effects of levetiracetam versus topiramate," Epilepsy Currents, 8(3):64-65 (2008).
Mecarelli et al., "Clinical cognitive, and neurophysiologic correlates of short-term treatment with carbamazepine, oxcarbazepine, and levetiracetam in healthy volunteers," Annual Pharmacotherapy, 38(11):1816-1822 (2004).
Medical College Of Wisconsin: "Network-Level Mechanisms for Preclinical Alzheimer's Disease Development," Clinicaltrials.gov, NCT03461861 version 13, retrieved from https://clinicaltrials.gov/ct2/show/NCT03461861?V 13, Mar. 12, 2018, pp. 9.
Meguro K. "Subjective memory complaints are not sine qua non as diagnostic criteria for MCI: the Tajiri project," Acta Neurologica Taiwanica, vol. 15, 2006, pp. 55-57.
Mendez et al., "The brain GABA-benzodiazepine receptor alpha-5 subtype in autism spectrum disorder: a pilot [.sup.11-C]R015-4513 position emission tomography study," Neuropharmacology (2013), 68:195-201.
Meo et al., "Use of levetiracetam monotherapy in patients with post-traumatic epilepsy: Preliminarv data," Epilepsia, 47(S4):162, p. 2135 (2006) (Abstract).
Meyers et al., "Neurocognitive Function," Symptoms Secondary to Cancer and its Treatment, pp. 557-571, (2002).
Miller et al., "Hippocampal activation in adults with mild cognitive impairment predicts subsequent cognitive decline," J Neural. Neurosurg. Psychiatry 79: 630-635 (2008).
Mirza et al., "NS11394 [3'-[5-(1-hydroxy-1-methyl-ethyl)-benzoimidazol-1-y1]-biphenyl-2-carbonitrile], a unique subtype-selective GABAA receptor positive allosteric modulator: in vitro actions, pharmacokinetic properties and in vivo anxiolytic efficacy," J Pharmacol Exp Ther 327(3): 954-68, 2008.
Mondadori et al., "Enhanced brain activity may precede the diagnosis of Alzheimer's disease by 30 years," Brain. 129:2908-22, 2006.
Mondadori et al., "The Effects of Nootropics on Memory: New Aspects for Basic Research," Pharmacopsychiatry, 22(S 2):102-106 (1989).
Morris, "Spatial Localization Does Nol Require the Presence of Local Cues," Leaming and Motivation 12:239-260 (1981).
Munro et al., "Comparison of the Novel Subtype-Selective GABA.sub.A Receptor-Positive Allosteric Modulator NS11394 [3'-[5-(1-Hydroxy-1-methyl-ethyl)-benzoimidazol-1-yl]-bipheny1-2-carbonilrile] with Diazepam, Zolpidem, Bretazenil, and Gaboxadol in Rat Models of Inflammatory and Neuropalhic Pain," J Pharmacol. Exp. Ther. 327(3):969-81 (2008).
Murray et al., "The effect of pramiracetam (CI-879) on the acquisition of a radial arm maze task," Psychopharmacology (Berl), 89(3):378-381 (1986).
Muscas et al., "[Efficacy and tolerability of Levetiracetam in epileptic patients with acquired progressive cognitive impairment]," Bollettino—Lega Italiana contro l'Epilessia, 129-130:233-234 (2005) (full text English translation).
Nicholson, "Pharmacology of nootropics and metabolically active compounds in relation to their use in dementia," Psychopharmacology, 101(No. 2):147-159 (1990).
Nishio et al., "A Mouse Model Characterizing Features of Vascular Dementia With HiDDOCampal Atrophy," Stroke vol. 41, pp. 1278-1284 (2010).
Nyberg, "Cognitive Impairments in Drug Addicts," Chapter 9 from the book Brain Damage—Bridging Between Basic Research and Clinics, 221-245 (2012).
Oler et al., "Age-Related Deficits in the Ability to Encode Contextual Change: A Place Cell Analysis," Hiooocampus, 2000, 10: 338-350.
Owens et al., "Alternative Routes of Insulin Delivery," Diabetic Medicine, 20:886-898 (2003).
Palop et al., "Aberrant excitatory neuronal activity and compensatory remodeling of inhibitory hippocampal circuits in mouse models of Alzheimer's disease," Neuron 55: 697-711 (2007).
Buchanan et al., "The FDA-NIMH-MATRICS guidelines for clinical trial design of cognitive-enchanceing drugs: what do we know 5 years later?," Schizophrenia Bulletin, 37(6):1209-1217 (2011).
El Youssoufi et al., "Glycosylated benzocycloheptadipyrazoles: a new class of water-soluble heterocyclic compounds," Bulletin de la Societe Chimique de France, 134(6):571-581 (1997).
Koh et al., "664.17/YY12-BPN-27473: a novel GABAaa5 positive allosteric modulator that improves memory performance of rats with conditions of hippocampal hyperactivity," Neuorscience, 2022 (https://www.abstractsonline.com/pp8/#!/10619/presentation/79719) (2 pages).
Nicolle et al., "In Vitro Autoradiography Of Ionolropic Glutamate Receptors In Hippocampus And Striatum Of Aged Long-Evans Rais: Relationship To Spatial Leaming," Neuroscience, 74(3):741-756 (1996).
Nicolle et al., "Metabotropic Glutamate Receptor-Mediated Hippocampal Phosphoinositide Turnover Is Blunted in Spatial Learning-Impaired Aged Rats," Journal of Neuroscience, 19(21):9604-9610 (1999).
Ronald et al., "Mild cognitive impairment: Aging to Alzheimer's Disease," New England Journal of Medicine, 349(14):1393 (2003) (1 page).
Buettelmann, et al., "Imidazo[1,5-a][1,2,4]-triazolo[1,5-d][1,4]benzodiazepines as potent and highly selective GABAA alpha5 inverse agonists with potential for the treatment of congnitive dysfunction," Bioorganic & Medicinal Chemistry Letters, 19(20):5958-5961 (2009).
Ciesielski, et al., "Neuropsychological and psychiatric impact of add-on titration of pregabalin versus levetiracetam: A comparative short-term study," Epilepsia, 47(S3):135 (2006)(Abstract).
Gill, et al., "The role of a5 GABAA receptor agonists in the treatment of cognitive deficits in schizophrenia," Current Pharmaceutical Design, 20(31):5069-5076 (2014).
Witt, et al., "The impact of antiepileptic drug treatment on attention and executive functions," Epilepsia, 51(S4):20 (2010) (Abstract).
Dickerson et al., "Increased hippocampal activation in mild cognitive impairment compared to normal aging and AD," Neurology, 2005, 65: 404-411.
Dietrich et al., "Clinical patterns and biological correlates of cognitive dysfunction associated with cancer therapy," Oncologist, vol. 13, 2008, pp. 1285-1295.
Donald et al., "Application of a sequential multicomponent assembly process/huisgen cycloaddilion strategy to the preparation of libraries of 1,2,3-Iriazole-fused 1,4-benzodiazepines," ACS Combinatorial Science, 14(2):135-143 (2012).
Ellison et al., "Beyond the "C" in MCI: Noncognitive Symptoms in Amnestic and Non-amnestic Mild Co!mi.tive Impairment," CNS Spectr. 13(1):66-72, 2008.
Ennaceur et al., "A new one-trial test for neurobiological studies of memory in rats. II: Effects of piracetam and pramiracetam," Behav. Brain Research, 33(2):197-207 (1989).
Enomoto et al., "Disruptions in spatial working memory, but not short-term memory, induced by repealed kelamine exposure," Progress in Neuro-Psychopharmacology & Biological Psychiatry 33 (2009) 668-675.
Essassi et al., "Recherches En Serie Benzodiazepine-1,5: Syntheses Des Dilriazolo-[4,3-a;3,4-d]-Benzodiazepines-1,5", Wiley Online Library, vol. 100, No. 3, 1991, pp. 277-286.
Fauser et al., "Effect of levetiracetam in limbic encephalitis: A case report," Epilepsia, 44(S 8): 111-112 p. 298 (2003) (Abstract).
Fedi et al., "Long-term efficacy and safety of piracetam in the treatment of progressive myoclonus epilepsy," Arch. Neurol., 58(5):781-786 (2001).
Folslein et al., ""Mini-mental state". A practical method for grading the cognitive state of patients for the clinician," Journal of Psychiatric Research, 12(3):189-198 (1975).
Fritz et al., "Effects of add-on treatment with topiramate or levetiracetam on cognition and health related quality of life for patients with epilepsy," Epilepsia, 46(S6):106-107 (2005) (Abstract).

(56) References Cited

OTHER PUBLICATIONS

Gallagher et al., "Relationship of age-related decline across several behavioral domains," Neurobiology of Aging, 10(6):691-708 (1989).
Gallagher et al., "Severity of spatial learning impairment in aging: development of a learning index for performance in the Morris water maze," Behavioral Neuroscience, 107(4):618-626 (1993).
Gallagher, "Animal models of memory impairment," Phil. Trans. R. Soc. Land. B., 352:1711-1717 (1997).
Gaudenzi et al., "[Levetiracetam therapy in patients with epilepsy and dementia]," Bollettino—Lega Italiana contro l'Epilessia, 125-126:215-216 (2004) (English Abstract onlv).
Gerecke, M., et al., New tetracyclic derivatives of imidazo-[1,5-a][1,4]benzodiazepines and of imidazo-[1,5-a]lhieno[3,2-f][1,4]diazepines, Helerocycles, 39(2):693-721 (1994).
Gharaghani et al., "A Structure-based QSAR and Docking Study on Imidazo[l,5-a][l,2,4]-triazolo[l,5-d][l,4,]benzodiazepines as Selective GABAAa5 Inverse Agonists", Chemical Biology Drug Design, vol. 78, No. 4, 2011, pp. 612-621.
Gill et al., "A novel a5GABA(A)R-positive allosteric modulator reverses hyperactivation of the dopamine system in the MAM model of schizophrenia," Neuropsychopharmacology, 36:1903-1911 (2011).
Giusti et al., "Imidazenil: A New Partial Positive Allosteric Modulator of .gamma.-Aminobutyric Acid (GABA) Action at GABA.sub.A Receptors.sup.I," The Journal of Pharmacology and Experimental Therapeutics, 1993, 266(2): 1018-1028.
Goldin et al., "Maintenance of Xenopus laevis and oocyte injection," Methods in Enzymology, 207: 266-279 (1992).
Goodacre et al., "Imidazo[1,2-.alpha.]pyrimidines as Functionally Selective and Orally Bioavailable GABA.sub.A.alpha.2/.alpha.3 Binding Site Agonists for the Treatment of Anxiety Disorders," J. Med. Chem., 2006, 49: 35-38.
Gotz et al., "Animal models of Alzheimer's disease and frontotemporal dementia," Nature Review vol. 9, pp. 532-544 (2008).
Gourevitch et al., "Working memory deficits in adult rats after prenatal disruption of neurogenesis," Behavioral Pharmacology, 15:287-292 (2004).
Grauer et al., "WAY-163909, a 5-HT2C agonist, enhances the preclinical potency of current antipsychotics," Psychopharmacology, 204(1):37-48 (2004).
Gualtieri et al., "Design and study of piracetam-like nootropics, controversial members of the problematic class of cognition-enhancing drugs," Current Pharmaceutical Design, 8(2):125-138 (2002).
Guido et al., "Event-related potentials (ERPs) in the evaluation of the effect of levetiracetam and carbamazepine on cognitive functions in adult patients with newly diagnosed epilepsy," European Journal of Neurology, 15(S3):305 (2008) (Abstract).
Guidotti et al., "GABAergic dysfunction in schizophrenia: new treatment strategies on the horizon," Psychopharmacology, 180:191-205 (2005).
Guo et al., "Effects of levetiracetam on quality of life in children with refractory epilepsy," Changjiang Daxue Xuebao, Ziran Kexueban, 8(1):151-155 (2011) (English Abstract onlv).
Haberman et al., "Rapid encoding of new information alters the profile of plasticity-related mRNA transcripts in the hippocampal CA3 region," PNAS, 105(30): 10601-10606 (2008).
Harvey et al., "Stress-restress evokes sustained iNOS activity and altered GABA levels and NMDA receptors in rat hippocampus," Psychopharmacology, 175: 494-502 (2004).
Hashimoto et al., "Alterations in GABA-related transcriptome in the dorsolateral prefrontal cortex of subjects with schizophrenia," Molecular Psychiatry, 13: 147-161 (2008).
Hashimoto et al., "Gene Expression Deficits in a Subclass of GABA Neurons in the Prefrontal Cortex of Subjects with Schizophrenia," J. Neurosc., 2003, 23(15): 6315-6326.
Helm et al., "GABAB receptor antagonist SGS?42 improves spatial memory and reduces protein binding to the cAMP response element (CRE) in the hippocampus," Neuropharmacology, 2005, 48: 956-964.
Helmstaedter, "'Real life' cohort study on levetiracetam versus carbamazepine monotherapy: a controlled surveillance study," Epilepsia, 50(S10): 100, p. 465 (2009) (Abstract).
Herholz et al., "Discrimination between Alzheimer dementia and controls by automated analysis of multicenter FDG PET," Neuroimage, 17(1):302-316 (2002).
Hill et al., "First Occurrence of Hippocampal Spatial Firing in a New Environment," Experimental Neurology, 1978, 62: 282-297.
Hines et al., "Functional regulation of GABAA receptors in nervous system pathologies," Current Opinion in Neurobiology, 22(3):552-558 (2012).
Huang et al., "Comparative cognitive effects of levetiracetam and topiramate in intractable epilepsy," Psychiatry and Clinical Neurosciences, 62(5):548-553 (2008).
Hughes et al., "Physiochemical drug properties associated with in vivo toxicological outcomes," Bioorganic & Medicinal Chemistry Letters, 18: 4872-4875 (2008).
Hussain, M. K., et al., Tandem C-2 Functionalization—Intramolecular Azide—Alkyne 1,3-Dipolar Cycloaddition Reaction: A Convenient Route to Highly Diversified 9H-Benzo[b]pyrrolo[1,2-g][1,2,3]triazolo[1,5-d][1,4]diazepines, Org. Lett., 16(2):560-563 (2014).
Jarrard "On the role of the hippocampus in learning and memory in the rat," Behav. Neural. Biol. 60(1):9-26 (1993).
Jonas et al., "First In Vivo Testing of Compounds Targeting Group 3 Medulloblastomas Using an Implantable Microdevice as a New Paradigm for Drug Development," Journal of Biomedical Nanotechnology, 12(6):1297-302 (2016).
Kamenelz et al. "APP processing and synaptic function," Neuron (2003) 37: 925-37.
Karakas et al., "Synthesis of the novel pyrrolo[2,l-d][l,2,5]benzotriazepine, pyrrolo[2,l-e][1,3,6]benzotriazocine and pyrrolo[l,2-a]tetrazolo[l,5-d][l,4]benzodiazepine ring systems. A new route to pyrrolo[l,2-a]quinoxaline via transamination of in situ generated 1-(2-aminophenyl)-2-iminomethylpyrroles", Tetrahedron, vol. 52, No. 32, 1996, pp. 10751-10760.
Kauer et al., "Synaptic plasticity and addiction," Nature. Reviews Neuroscience, 8:844-858 (2007).
Khan et al., "Topiramate attenuates exaggerated acoustic startle in an animal model of PTSD," Psychopharmacology 172(2):225-229 (2004).
Kim et al., "Transient impairment of hippocampus-dependent learning and memory in relatively low-dose of acute radiation syndrome is associated with inhibition of hippocampal neurogenesis," Journal of Radiation Research, 49:517-526 (2008).
Kluger et al., "Neuropsychological prediction of decline to dementia in nondemented elderly," Journal of Geriatric Psychiatry and Neurology, 12(4):168-79 (1999).
Knust H. et al., "The discovery and unique pharmacological profile of RO4938581 and RO4882224 as potent and selective GABA (Alfa5) inverse agonists for the treatment of cognitive dysfunction", Bioorganic & Medical Chemistry Letters, vol. 19, 2009, pp. 5940-5944.
Caira, "Crystalline Polymorphism of Organic Compounds," Topics in Current Chemistry, 198:168-214 (228 pages) (1998).
Kaminski et al., "Benefit of combination therapy in epilepsy: A review of the preclinical evidence with levetiracetam," Epilepsia , 50(3):387-97 (2009).
Parnetti et al., "Neuropsychological results of long-term therapy with oxiracetam in patients with dementia of Alzheimer type and multi-infarct dementia in comparison with a control group," Neuropsychobiology, 22(2):97-100 (1989).
Paschel et al., "Pharmacologic therapeutic window of pramiracetam demonstrated in behavior, EEG, and single neuron firing rates," Experientia., 41(9):1153-1156 (1985).
Paschel et al., "Pharmacology of the cognition activator pramiracetam (CI-879)," Drugs under Experimental and Clinical Research, 9(12):853-872 (1983).
Pastor et al., "Tolerability and efficacy of the combination of piracetam and citicoline in acute ischemic stroke. A randomized comparative open study," p. e286, top right-hand column, paragraph 1 of Abstract of the 5th World Stroke Conference, Jan. 2004,

(56) References Cited

OTHER PUBLICATIONS

Retrieved from the Internet: http://stroke.ahajournals.org/content/35/6/e276.full.pdf#page=1$view=Fith.
Patani et al., "Bioisosterism: A Rational Approach in Drug Design," Chemical Reviews vol. 96, pp. 3147-3176 (1996)* .sup.4.
Patsalos, "Clinical pharmacokinetics of levetiracetam," Clin. Pharmacokinet., 43(11):707-724 (2004).
Pepeu et al., "Mild cognitive impairment: animal models," Dialogs Clin. Neurosci., vol. 6 pp. 369-377 (2004).
Petersen et al., "Mild cognitive impairment: clinical characterization and outcome," Archives in Neurology, 56(3):303-308 (1999).
Petersen RC, Negash S. Mild cognitive impairment: an overview. CNS spectrums. Jan. 2008; 13(1):45-53.
Petersen RC, Smith GE, Waring SC, Ivnik RJ, Tangalos EG, Kokmen E. Mild cognitive impairment: clinical characterization and outcome. Archives of neurology. Mar. 1, 1999;56(3):303-8.
Petersen RC. Mild cognitive impairment: current research and clinical implications. InSeminars in neurology Feb. 2007 (vol. 27, No. 01, pp. 022-031). Copyright © 2007 by Thieme Medical Publishers, Inc., 333 Seventh Avenue, New York, NY 10001, USA.
Plassman et al., "Prevalence of cognitive impairment without dementia in the United States," Annals of Internal Medicine, 148(6):427-434 (2008).
Platel et al., "Habituation of exploratory activity in mice: effects of combinations of piracetam and choline on memory processes," Pharmacol. Biochem. Behav., 21(2):209-212 (1984).
Platt et al., "Contribution of .alpha..sub.1GABA.sub.A and .alpha..sub.5GABA.sub.A receptor subtypes to the discriminative stimulus effects of ethanol in squirrel monkeys," J. Pharmacol. & Exp. Ther., 313(2):658-667 (2005).
Pugsley et al., "Some neurochemical properties of pramiracetam (CI-879) a new cognition enhancing agent," Drug Development Research, 3(5):407-420 (1983).
Pym et al., "Selective labelling of diazepam-insensitive GABA.sub.A receptors in vivo using [.sup.3H]Ro 15-4513," British Journal of Pharmacology, 2005, 146: 817-825.
Qin et al., "Evaluation of methods for oligonucleotide array data via quantitative real-time PCR," BMC Bioinformatics, 7:23: 1-12 (2006).
Rapp et al., "An Evaluation of Spatial Information Processing in Aged Rats," Behavioral Neuroscience, 1987, 101(1):3-12.
Rapp et al., "Memory systems in normal and pathological aging," Curr. Opin. Neurol., 7:294-298 (1994).
Rapp et al., "Preserved neuron No. In the hippocampus of aged rats with spatial learning deficits," Proceedings of the National Academy of Science USA, 93(18):9926-9930(1996).
Reid et al., "Synthese neuer 1,3-Diazepine", Zeitung, vol. 111, No. 5, 1987, pp. 179-180.
Reilly et al., "Effects of Acamprosate on Neuronal Receptors and Ion Channels Expressed in Xenopus Oocytes," Alcohol Clin Exp Res, Feb. 2008, 32(2): 188-196.
Rinaldi et al., "Hyper-connectivity and hyper-plasticity in the medial prefrontal cortex in the valproic acid animal model of autism," (2008), Frontiers in Neural Circuits, 2, 1-7.
Robbins et al., "Cambridge Neuropsychological Test Automated Battery (CANTAB): a factor analytic study of a large sample of normal elderly volunteers," Dementia, 5(5):266-281 (1994).
Rodier et al., "Linking etiologies in humans and animal models: studies of autism," (1997) Reprod. Toxicol. 11, 417-422.
Rosche et al. "Different cognitive effects of inducing levetiracetam or topiramate into an antiepileptic pharmacotherapy in patients with therapy refractory epilepsy," Neurology, Psychiatry and Brain Research, 11:109-114 (2004).
Rosenzweig-Lipson et al., "Antidepressant-like effects of the novel, selective, 5-HT2c receptor agonist WAY-163909 in rodents," (2007) Psychopharmacology 192:159-170.
Rozzini et al., "Treatment of cognitive impairment secondary to degenerative dementia. Effectiveness of oxiracetam therapy," Acta. Neurol. (Napoli), 15(1):44-52 (1993).
Rudakova et al., "Levetiracetam (keppra) in the treatment of different epileptic syndromes in adults," Zhumal nevrologii i psikhiatrii imeni S.S. Korsakova / Ministerstvo zdravookhraneniia i meditsinskoi promyshlennosti Rossiiskoi Federatsii, Vserossiiskoe obshchestvo nevrologov [ii Vserossiiskoe obshchestvo psikhiatrov, 109(10):25-29 (2009) (English Abstract only).
Ryzhkov, "Advantages oflevetiracetam as monotherapy in treating epileptic syndromes of early childhood, characterized by psychological disorders," European Journal of Neurology, 14(S1):90, p. 1224 (2007) (Abstract).
Sankaranarayanan, "Genetically modified mice models for Alzheimer's disease," Current Topics in Medicinal Chemistry, 6(6):609-627 (2006).
Sara et al., "Piracetam facilitates retrieval but does not impair extinction of bar-pressing in rats," Psvchopharnacology (Berl.), 61(1):71-75 (1979).
Schneider et al., "Validity and reliability of the Alzheimer's Disease Cooperative Study—Clinical Global Impression of Change," The Alzheimer's Disease Cooperative Study, Alzheimer Dis. Assoc. Disord., 11 SuDDL 2:S22-S32 (1997).
Schoenberg et al., "Results of a randomized double-blind placebo controlled cross-over study of the cognitive and mood effects of levetiracetam in healthy older adults," Epilepsia, 48(S6):339, p. 3.246 (2007) (Abstract).
Schoenberg, M. R., "A randomized, double-blind, placebo-controlled crossover study of the effects of levetiracetam on cognition, mood, and balance in healthy older adults", Epilepsia, 58:(9) 1566-1574 (2017).
Sengupta et al., "a5-GABAA receptors negatively regulate MYC-amplified medulloblastoma growth.," Acta Neuropathologica, 127(4):593-603 (2014).
Shorvon, "Pvrrolidone derivatives," Lancet, 358(9296):1885-1892 (2001).
Silverman et al., "Negative Allosteric Modulation of the mGluR5 Receptor Reduces Repetitive Behaviors and Rescues Social Deficits in Mouse Models of Autism," Sci Transl. Med., Apr. 25, 2012, 4(131) 1-9.
Singhal et al., "Drug polymorphism and dosage form design: a practical perspective", Advanced Drug Delivery Reviews, 56:335-347 (2004).
Small et al., "Imaging correlates of brain function in monkeys and rats isolates a hippocampal subregion differentially vulnerable to aging," Proc. Nall. Acad. Sci. USA., 101(18):7181-7186 (2004).
Smith et al., "Circuit-specific alterations in hippocampal synaptophysin immunoreactivity predict spatial learning impairment in aged rats," J. Neuroscience, 20(17):6587-6593 (2000).
Smith, G et al.; Age-associated memory impairment diagnoses: problems of reliability and concerns for terminology.; 6(4):551-558 (1991).
Soussain et al., "CNS complications of radiotherapy and chemotherapy," Lancet vol. 374, 2009, pp. 1639-1651.
Specchio et al., "Event-related potentials (erps) in the evaluation of the effect of levetiracetam and carbamazepine on cognitive functions in adult newly diagnosed epileptic patients. preliminary results of a randomized open trial," Epilepsia, 50(54):98, T189 (2009) (Abstract).
Steele et al., "Delay-dependent impairment of a matching-to-place task with chronic and intrahippocampal infusion of the NMDA-antagonist D-AP5," Hippocampus 9(2):118-36 (1999).
Sternfeld et al., "Selective, orally active .gamma.-aminobutyric acid.sub.A .alpha.5 receptor inverse agonists as cognitition enhancers," J. Med. Chem., 47:2176-2179 (2004).
Sur et al., "Rat and Human Hippocampal .alpha.5 Subunit-Containing .gamma-Aminobutyric Acid.sub.A Receptors Have .alpha.5.beta.3.gamma.2 Pharmacological Characteristics." Molecular Pharmacology, 1998, 54: 928-933.
Szekeres et al., "3,4-Dihydronaphthalen-1(2H)-ones: novel ligands for the benzodiazepine site of .alpha.5-containing GABA.sub.A receptors," Bioorg. Med. Chem. Lett., 14:2871-2875 (2004).
Tanila et al., "Discordance of Spatial Representation in Ensembles of Hiooocampal Place Cells," Hiooocampus, 1997, 7: 613-623.
Abou-Khalil, "Benefit-risk assessment of levetiracetam in the treatment of partial seizures," Drug Safety, 28(10):871-890 (2005).
Achermann et al., "Discovery of the imidazo [1,5-.alpha.][1,2,4]-triazolo[1,5-d][1,4] benzodiazepine scaffold as a novel, potent and

(56) References Cited

OTHER PUBLICATIONS selective GABA.sub.A .alpha.5 inverse agonist series," Aug. 2009, Bioorganic & Medicinal Chemistry Letters, vol. 19, pp. 5746-5752*. sup.16.
Adams et al., "Hippocampal dependent learning ability correlates with N-methyl-D-aspartate (NMDA) receptor levels in CA3 neurons of young and aged rats," J. Comp. Neural., 432:230-243 (2001).
Agam et al., "Levetiracetam does not interfere with attention to novel and targeted stimuli: An psychophysiological study," Neurology, 68(12), S1, p. 06.051 (2007) (Abstract).
Aisen et al., "Clinical Core of the Alzheimer's Disease Neuroimaging Initiative: progress and plans," Alzheimer's & Dementia, 6(3):239-246 (2010).
Akbarian et al., "Gene Expression for Glutamic Acid Decarboxylase Is Reduced Without Loss of Neurons in Prefrontal Cortex of Schizophrenics," Arch. Gen. Psychiatry 52:258-266, 1995.
Albert, "The ageing brain: normal and abnormal memory," Philos. Trans. R. Soc. Land. B. Biol. Sci., 352:1703-1709 (1997).
Arcas et al., "Levetiracetaminn children and adolescents with refractory epilepsy: A clinical experience," Epilepsia, 47(S3):179 Absp696 (2006) (Abstract).
Ashe et al., "Probing the biology of Alzheimer's disease in mice," Neuron., 2010, 66(5): 631-645.
Auta et al., "Imidazenil: A Low Efficacy Agonist at .alpha.1—but High Efficacy at alpha.5-GABA.sub.A Receptors Fail to Show Anticonvulsant Cross Tolerance to Diazepam or Zolpidem," Neuropharmacology, 2008, 55(2): 148-153.
Bakker et al., "Pattern separation in the human hippocampal CA3 and dentate gyms," Science, 319: 1640-1642 (2008).
Bakker et al., "Reduction of hippocampal hyperactivity improves cognition in amnestic mild cognitive impairment," Neuron, 74(3): 467-474 (2012).
Bakker et al., "Response of the medial temporal lobe network in amnestic mild cognitive impairment to therapeutic intervention assessed by fMRI and memory task performance," NeuroImage Clinical, 21(7):688-698 (2015).
Baldessarini et al., "Drugs and the Treatment of Psychiatric Disorders," (2001) Goodman & Gilman's The Pharmacological Basis of Therapeutics 10 Edition, 485-520.
Ballard et al., "R04938581, a novel cognitive enhancer acting at GABA.sub.A .alpha.5 subunit-containing receptors," Psychopharmacology, 2009, 202: 207-223.
Barker et a1, "A Prevalence Study of Age-Associated Memory Impairment," British Journal of Psychiatry, 167:642-648 (1995).
Barnes et al., "Region-specific age effects on AMP A sensitivity: electrophysiological evidence for loss of synaptic contacts in hippocampal field CA1," Hippocampus, 2:457-468 (1992).
Bartus et al., "The cholinergic hypothesis of geriatric memory dysfunction," Science, 217:408-417 (1982).
Basseti et al., "Familial risk for Alzheime(s disease alters fMRI activation patterns," Brain., 2006, 129(5): 1229-1239.
Baxter et al., "Neurobiological substrates of behavioral decline: models and data analytic strategies for individual differences in aging," Neurobiol. Of Aging, 17:491-495 (1996).
Beatrice Brunner et al., Neurocognitive effects of antiepileptic drugs frequently used in long term treatement of epilepsies: A review, Epileptologie, 25:118-130 (2008).
Becker et al., "Why Do So Many Drugs for Alzheimer's Disease Fail in Development? Time for New Methods and New Practices?" J. Alzheimers Disease vol. 15 (2): 303-325 (2008).
Berezhnoy et al., "Pharmacological Properties of DOV 315,090, an ocinaplon metabolite," BMC Pharmacology, 2008, 8:11: 1-10.
Berntsen, "The Unbidden Past: Involuntary Autobiographical Memories as a Basic Mode of Remembering," Current Directions in Psychological Science 19(3) 138-142, 2010.
Berton et al., "Acamprosate Enhances N-Methyl-D-Apartate Receptor-Mediated Neurotransmission But Inhibits Presynaptic GABAB Receptors in Nucleus Accumbens Neurons," Alcohol Clin Exp Res, Feb. 1998, 22(1): 183-191.
Betarbet et al., "Animal models of Parkinson's disease," BioEssays, 24(4):308-318 (2002).
Blalock et al., Gene Microarrays in Hippocampal Aging: Statistical Profiling Identifies Novel Processes Correlated with Cognitive Impairment, J. Neurosci., 2003, 23(9): 3807-3819.
Bontekoe et al., "Knockout mouse model for Fxr2: a model for mental retardation," Human Molecular Genetics, 11(5):487-498 (2002).
Bookheimer et al., "Patterns of Brain Activation in People at Risk for Alzheime s Disease", N Engl J Med., 2000, 343(7): 450-456.
Bootsma et al., "The effect of antiepileptic drugs on cognition: patient perceived cognitive problem of topiramale versus leveliracetam in clinical practice," Epilepsia, 47(S2):24-27 (2006).
Brewer et al., "Optimized survival of hippocampal neurons in B27-supplemented Neurobasal, a new serum-free medium combination," J. Neuroscience Res. 35:567-576 (1993).
Brown et al., "Impact of levetiracetam on mood and cognition during prednisone therapy," European Psychiatry, 22(7):448-452 (2007).
Busche et al., "Clusters of Hyperactive Neurons Near Amyloid Plaques in a Mouse Model of Alzheime s Disease," Science, 2008, 321: 1686-1689.
Buschke et al., "Evaluating storage, retention, and retrieval in disordered memory and learning," Neurology, 24:1019-1025 (1974).
Bustamante et al., "A Modification of the Extended Hildebrand Approach to Predict the Solubility of Structurally Related Drugs in Solvent Mixtures," Journal of Pharmacy and Pharmacology, 45:253-257 (1993).
Carling et al., "7-(1, l-Dimethylethyl)-6-(2-ethyl-2H-l,2,4-Iriazol-3-ylmelhoxy)-3-(2-fluorophenyl)-l,2,4-triazolo[4,3-b]pyridazine: A Functionally Selective .gamma.-Aminobutyric Acid.sub.A (GABA.sub.A).alpha.2/.alpha.3-Subtype Selective Agonisl Thal Exhibits Potent Anxiolytic Activity but Is Nol Sedating in Animal Models", Journal of Medicinal Chemistry, 2005, 48(23): 7089-7092.
Celone et al., "Alterations in Memory Networks in Mild Cognitive Impairment and Alzheimers Disease: An Independent Component Analysis," J. Neurosci., 2006, 26(40): 10222-10231.
Chambers "An Orally Bioavailable, Functionally Selective Inverse Agonisl at the Benzodiazepine Site of GABA.sub.A .alpha.5 Receptors with Cognition Enhancing Properties," J. Med. Chem., 47:5829-5832 (2004).
Chambers et al. Identification of a Novel, Selective GABAA a5 Receptor Inverse Agonisl Which Enhances Cognition, J. Med. Chem., vol. 46, 2003, pp. 2227-2240.
Chappell et al., "A re-examination of the role of basal forebrain cholinergic neurons in spatial working memory," Neuropharmacology, 37(4-5):481-487 (1998).
Ciccocioppo et al., "Genetically selected Marchigian Sardinian alcohol-preferring (msP) rats: an animal model to study the neurobiology of alcoholism," Addiction Biology, 11(3-4):339-355 (2006).
Cicolin et al., "[Levetiracetam and cognitive functions: A single blind, crossover, placebo controlled study in healthy volunteers]," Bolletinno Lega Italiana contro l'Epilessia, No. 113-114:79-81 (2001) (English Abstract only).
Ciesielski et al., "Neuropsychological and psychiatric impact of add-0n titration of pregabalin versus levetiracetam: a comparative short-term study," Epilepsy & Behavior, 9(3):424-431 (2006).
Colombo et al., "Spatial memory is related to hippocampal subcellular concentrations of calcium-dependent protein kinase C isoforms in young and aged rats," Proceedings of the National Academy of Science USA, 94(25):14195-14199 (1997).
Costa et al., "GABA.sub.A receptors and benzodiazepines: a role for dendritic resident subunit mRNAs," Neuropharmacology 43: 925-937 (2002).
Crook et al., "Age-associated memory impairment: Proposed diagnostic criteria and measures of clinical change—report of a national institute of mental health work group," Developmental Neuropsychology, 2(4):261-276 (1986).
Cross et al., "Rules for the Nomenclature of Organic Chemistry: Section E: Stereochemistry," Pure Annl. Chem. (1976), 45, 11-30.
De Hoz et al., "Spatial learning with unilateral and bilateral hippocampal networks," European Journal of Neuroscience, 22(3):745-54 (2005).

(56) References Cited

OTHER PUBLICATIONS

Di Braccia et al., "1,5-Benzodiazepines XIV. Synthesis of new substituted 9H-bis-[1,2,4] Iriazolo[4,3-a:3',4'-d][1,5]benzodiazepines and relate compounds endowed with in vitro cytotoxic properties", Farmaco, vol. 60, No. 2, 2005, pp. 113-125.
Dickerson BC et al., "Medial temporal lobe function and structure in mild cognitive impairment," Ann. Neural. 56:27-35 (2004).
Black, "Flow Chart Determination of Isomer Relationships," Journal of Chemical Education, 67(2):141-142 (1990).
Manoj et al., "Review of Brain and Brain Cancer Treatment," International Journal of Pharma and Bio Sciences, 2(1): p. 468-p. 477 (2011).

* cited by examiner

| | BPN-27473 |
|---|---|
| Bravais Type | Primitive Monoclinic |
| a [Å] | 14.254 |
| b [Å] | 4.041 |
| c [Å] | 36.069 |
| α [deg] | 90 |
| β [deg] | 106.84 |
| γ [deg] | 90 |
| Volume [$Å^3$/cell] | 1,988.5 |
| Chiral Contents? | Not Specified |
| Extinction Symbol | P 1 c 1 |
| Space Group(s) | Pc (7), P2/c (13) |
| Source | Manual Input |

Indexing is a non-cGMP activity

Output Rendered using Triads v2.1.1

Indexing results for XRPD file 981288 collected with Cu-Kα radiation.

| | BPN-27473 |
|---|---|
| Bravais Type | Triclinic |
| a [Å] | 9.104 |
| b [Å] | 9.279 |
| c [Å] | 12.416 |
| α [deg] | 89.06 |
| β [deg] | 86.31 |
| γ [deg] | 77.95 |
| Volume [Å$^3$/cell] | 1,023.6 |
| Chiral Contents? | Not Specified |
| Extinction Symbol | P - |
| Space Group(s) | Pc (1), $P\bar{1}$ (2) |
| Source | Triads Algorithm |

Indexing is a non-cGMP activity

Output Rendered using Triads v2.1.1

| | BPN-27473 |
|---|---|
| Bravais Type | Primitive Monoclinic |
| a [Å] | 14.406 |
| b [Å] | 4.028 |
| c [Å] | 38.206 |
| α [deg] | 90 |
| β [deg] | 100.94 |
| γ [deg] | 90 |
| Volume [$Å^3$/cell] | 2,176.7 |
| Chiral Contents? | Not Specified |
| Extinction Symbol | P 1 c 1 |
| Space Group(s) | Pc (7), P2/c (13) |
| Source | Manual Input |

POLYMORPHS OF A GABA$_A$ α5 AGONIST AND METHODS OF USING IN THE TREATMENT OF COGNITIVE IMPAIRMENT

CROSS-REFERENCE TO RELATED APPLICATIONS

This application is a national stage application under 35 U.S.C. § 371 of International Application PCT/US2021/041179, filed Jul. 9, 2021, which claims the benefit of and priority from U.S. Provisional Application 63/050,642, filed Jul. 10, 2020, both of which applications are incorporated herein by reference in their entireties.

STATEMENT OF GOVERNMENT SUPPORT

This invention was made with government support under Grant No. UH3NS101856 awarded by the National Institutes of Health (NIH), and in particular, its National Institute on Aging (NIA) division, an agency of the United States Government. The United States Government has certain rights in the invention.

FIELD OF THE INVENTION

The invention relates to crystalline forms i.e., polymorphs of a GABA$_A$ α5 agonist, pharmaceutical compositions and combinations comprising those crystalline forms, and their use in methods of treating cognitive impairment associated with central nervous system (CNS) disorders, cognitive impairment associated with brain cancer, the brain cancer itself or Parkinson's disease psychosis.

BACKGROUND OF THE DISCLOSURE

Cognitive ability may decline as a normal consequence of aging or as a consequence of a central nervous disorder. For example, a significant population of elderly adults experiences a decline in cognitive ability that exceeds what is typical in normal aging. Such age-related loss of cognitive function is characterized clinically by progressive loss of memory, cognition, reasoning, and judgment. Age-related Mild Cognitive Impairment (MCI), Age-Associated Memory Impairment (AAMI), Age-Related Cognitive Decline (ARCD) or similar clinical groupings are among those related to such age-related loss of cognitive function. According to some estimates, there are more than 16 million people with AAMI in the U.S. alone (Barker et al., 1995), and age-related MCI is estimated to affect 5.5-7 million in the U.S. over the age of 65 (Plassman et al., 2008).

Cognitive impairment is also associated with other central nervous system (CNS) disorders, such as dementia, Alzheimer's Disease (AD), prodromal AD, post-traumatic stress disorder (PTSD), schizophrenia, bipolar disorder (in particular, mania), amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

There is, therefore, a need for effective treatment of cognitive impairment associated with central nervous system (CNS) disorders, including, but not limited to those related to aging, such CNS disorders include, for example, age-related cognitive impairment, MCI, amnestic MCI, AAMI, ARCD, dementia, Alzheimer's disease (AD), prodromal AD, post-traumatic stress disorder (PTSD), schizophrenia, bipolar disorder (e.g., mania), amyotrophic lateral sclerosis, cancer-therapy-related cognitive impairment, mental retardation, Parkinson's disease (PD), autism, compulsive behavior, and substance addiction, as well as other central nervous system (CNS) disorders associated with cognitive impairment.

Further, there is a need to treat cognitive impairment associated with brain cancer, or to treat brain cancer itself, in a subject in need thereof. Additionally, there is a need to treat Parkinson's disease psychosis in subject in need thereof.

Studies have demonstrated that the use of GABA$_A$ α5 agonists are useful in the treatment of cognitive impairment associated with CNS disorders, cognitive impairment associated with brain cancer, brain cancer, or Parkinson's disease psychosis. See, for example, WO 2015/095783, WO 2016/205739, WO 2018/130869, WO 2018/130868, WO 2019/246300, and U.S. 62/950,886. It has further been found that the compound having the structure

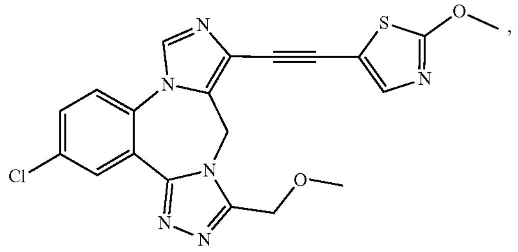 [SMILES: COCc1nnc2n1Cc1c(C#Cc3cnc(OC)s3)ncn1-c1ccc(Cl)cc1-2]

herein designated Compound 1 is a specific example of a GABA$_A$ α5 agonist that, for example, improves cognition in cognitively impaired subjects. A synthetic procedure has been described for Compound 1 (see WO 2019/246300). However, Compound 1 was not heretofore known to exist in any polymorphic forms.

SUMMARY OF THE DISCLOSURE

The present disclosure provides crystalline forms of Compound 1, having the structure

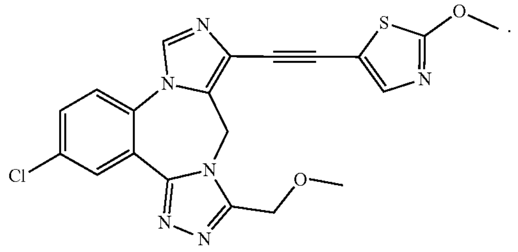 [SMILES: COCc1nnc2n1Cc1c(C#Cc3cnc(OC)s3)ncn1-c1ccc(Cl)cc1-2]

In some embodiments, the crystalline forms are salts, solvates, or hydrates. The disclosure also provides pharmaceutical compositions comprising the crystalline forms of Compound 1. The disclosure also provides processes for preparing the crystalline forms of Compound 1, as well as methods for using them in the treatment of cognitive impairment associated with a central nervous system (CNS) disorder or a brain cancer, treating a brain cancer, or treating Parkinson's disease psychosis.

In one aspect, this disclosure is directed to a crystalline form of Compound 1, wherein the crystalline form is Form A.

In another aspect, this disclosure is directed to a crystalline form of Compound 1, wherein the crystalline form is Form B.

In another aspect, this disclosure is directed to a crystalline form of Compound 1, wherein the crystalline form is Form C.

In another aspect, this disclosure is directed to a crystalline form of Compound 1, wherein the crystalline form is Form E.

In another aspect, this disclosure is directed to a crystalline form of Compound 1, wherein the crystalline form is Form F.

In one aspect, this disclosure is directed to a pharmaceutical composition comprising a crystalline form of Compound 1.

In another aspect, this disclosure is directed to a pharmaceutical combination comprising:

a. a first pharmaceutical composition comprising a crystalline form of Compound 1 as described herein; and b. one or more additional pharmaceutical compositions comprising one or more therapeutic agents selected from the group consisting of an antipsychotic, memantine, an SV2A inhibitor, and an acetylcholineesterase inhibitor (AChEI), or a pharmaceutically acceptable salt, hydrate, solvate, polymorph or prodrug of any of the foregoing.

In another aspect of the disclosure, there is provided a method for treating cognitive impairment associated with a CNS disorder in a subject in need of treatment or at risk of said cognitive impairment, the method comprising the step of administering to said subject a therapeutically effective amount of a crystalline form of Compound 1 according to this disclosure. In some embodiments, the CNS disorder with cognitive impairment includes, without limitation, age-related cognitive impairment, including age-related Mild Cognitive Impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

In another aspect of the disclosure, there is provided a method of preserving or improving cognitive function in a subject in need thereof, the method comprising the step of administering to said subject a therapeutically effective amount of a crystalline form of Compound 1 according to the disclosure. In certain embodiments of the disclosure, a crystalline form of Compound 1 of the disclosure is administered every 12 or 24 hours.

In another aspect of the disclosure, there is provided a method for treating brain cancers (including brain tumors, e.g., medulloblastomas) in a subject in need thereof, the method comprising the step of administering to said subject a therapeutically effective amount of a crystalline form of Compound 1 of the disclosure.

In another aspect of the disclosure, there is provided a method of preserving or improving cognitive function in a subject suffering from brain cancers (including brain tumors, e.g., medulloblastomas), the method comprising the step of administering to said subject a therapeutically effective amount of a crystalline form of a compound of the disclosure. In certain embodiments of the disclosure, a crystalline form of a compound of the is administered every 12 or 24 hours.

In another aspect of the disclosure, there is provided a method for treating Parkinson's disease psychosis in a subject in need thereof, the method comprising the step of administering to said subject a therapeutically effective amount of a crystalline form of a compound of the disclosure. In certain embodiments, a crystalline form of a compound of the is administered every 12 or 24 hours.

In some embodiments, the crystalline forms of the compounds according to this disclosure, and the pharmaceutical combinations and compositions comprising those crystalline forms are for use as, or in the manufacture of, a medicament. In some embodiments, the crystalline forms of the compounds, and the pharmaceutical combinations and compositions comprising those crystalline forms, are for use in, or in the manufacture of a medicament for, treating cognitive impairment associated with a CNS disorder in a subject in need of treatment or at risk of said cognitive impairment. In some embodiments, the CNS disorder with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In some embodiments, the compounds, compositions and combinations of the present disclosure are for use as a medicament in treating brain cancers (including brain tumors, e.g., medulloblastomas). In some embodiments, the crystalline form of the compounds, compositions and combinations of the present disclosure are for use as, or in the manufacture of, a medicament for treating cognitive impairment associated with brain cancers (including brain tumors, e.g., medulloblastomas). In some embodiments, the crystalline form of the compounds, compositions and combinations of the present disclosure are for use as a medicament in treating Parkinson's disease psychosis.

In another aspect of the disclosure is provided a method of producing an anhydrous crystalline form, Form A, of Compound 1, the method comprising:

a. dissolving the compound in dichloromethane;

b. evaporating the dichloromethane to produce a precipitate; and c. recovering the precipitate to afford the anhydrous crystalline, Form A, of the compound.

In another aspect is provided a method of producing an anhydrous crystalline form, Form A, of Compound 1, the method comprising:

a. dissolving the compound in a first solvent to produce a solution at a first temperature;

b. adding a second solvent to the solution to form a mixture;

c. optionally cooling the mixture to a second temperature; and d. recovering the resulting precipitate to afford the anhydrous crystalline form, Form A, of the compound.

In another aspect is provided a method of producing methanolate crystalline form, Form C, of Compound 1, the method comprising:

a. Combining the compound in a methanol to form a mixture;

b. mixing the mixture for a period of time;

c. optionally evaporating the methanol from the mixture; and d. recovering the precipitate to afford the methanolate crystalline form, Form C, of the compound.

In another aspect is provided a method of producing a desolvated crystalline form, Form B, of Compound 1, the method comprising:

a. obtaining methanolate Form C of the compound;

b. heating the compound for a period of time to form the desolvated crystalline form, Form B, of the compound.

In another aspect is provided a method of producing a monohydrate crystalline form, Form F, of Compound 1, the method comprising:

a. obtaining a hydrochloride salt of the compound;

b. adding the hydrochloride salt of the compound to a solvent to form a mixture;

c. mixing the mixture for a period of time;

d. recovering the precipitate to afford the monohydrate crystalline form, Form F, of the compound.

In another aspect is provided a method of producing an anhydrous crystalline form, Form E, of Compound 1, the method comprising:

a. dissolving the compound in tetrahydrofuran at a first temperature to form a solution;

b. adjusting the first temperature to a second temperature to induce precipitation;

c. recovering the precipitate to afford the anhydrous crystalline form, Form E, of the compound.

BRIEF DESCRIPTION OF THE DRAWINGS

FIG. 3A (top) corresponds to the thermogravimetric analysis (TGA) curve and FIG. 3B (bottom) corresponds to the differential scanning calorimetry (DSC) curve.

FIG. 9A (top) corresponds to the TGA curve, and FIG. 9B (bottom) corresponds to the DSC curve.

FIG. 12A (top) corresponds to the TGA curve, and FIG. 12B (bottom) corresponds to the DSC curve.

FIG. 15A (top) corresponds to the TGA curve, and FIG. 15B (bottom) corresponds to the DSC curve.

FIG. 18A (top) corresponds to the TGA curve, and FIG. 18B (bottom) corresponds to the DSC curve.

FIG. 21A shows the amount of time spent in target quadrants after acute treatment with Compound 1 (10 mg/kg); FIG. 21B shows the amount of time spent in target quadrants after chronic treatment (12 weeks) with Compound 1 (10 mg/kg).

DETAILED DESCRIPTION OF THE DISCLOSURE

Definitions

Figure 1:
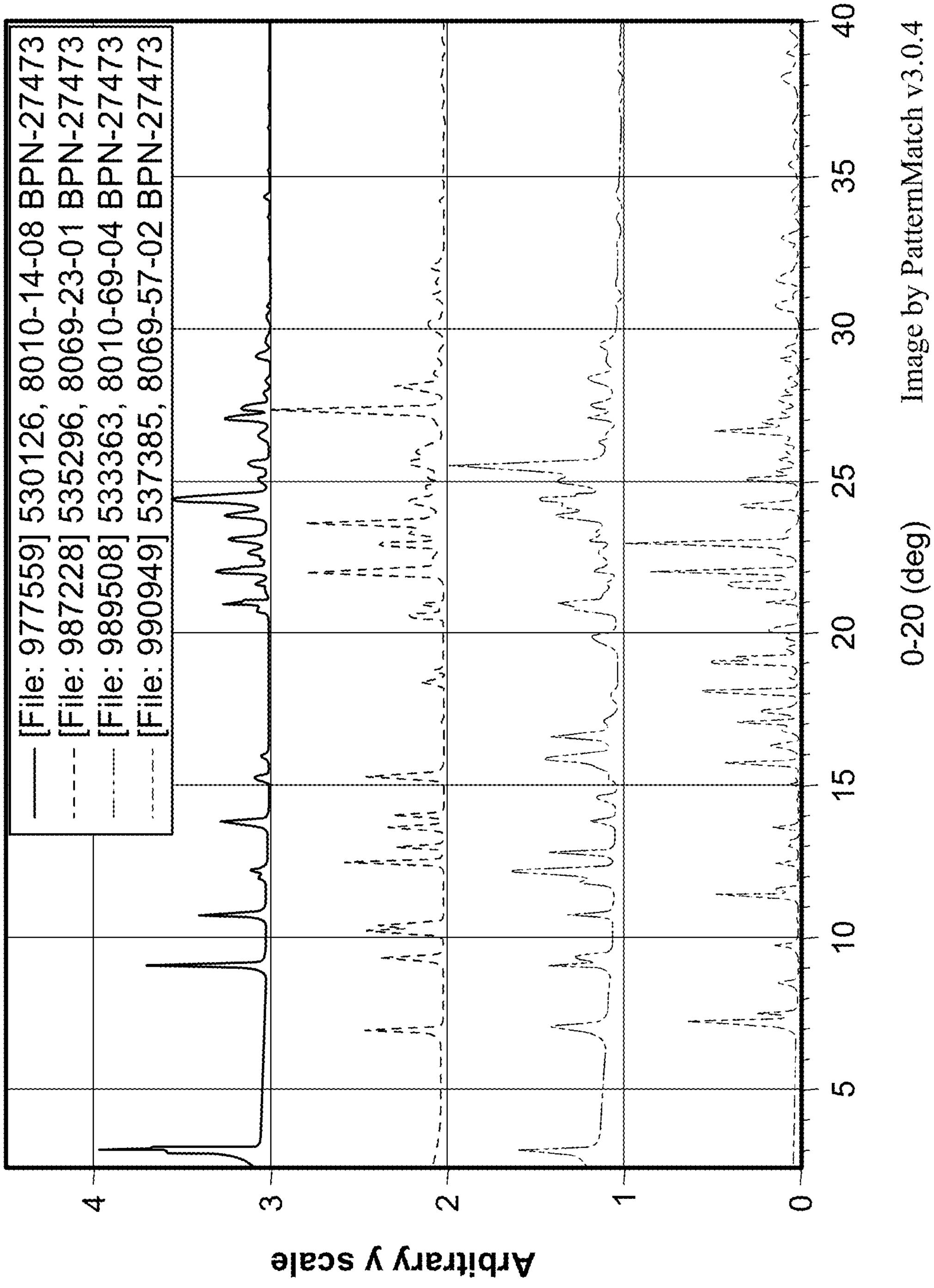
FIG. 1 is an XRPD pattern overlay of anhydrous polymorphic forms of Compound 1. The top diffractogram corresponds to anhydrous Form A, the second from the top corresponds to desolvated Form B, the third from the top corresponds to anhydrous Material D (as a mixture with Form A), and the bottom corresponds to anhydrous Form E

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science," McGraw-Hill Medical, New York, N.Y. (2000); Motulsky, "Intuitive Biostatistics," Oxford University Press, Inc. (1995); Lodish et al., "Molecular Cell Biology, 4th ed.," W. H. Freeman & Co., New York (2000); Griffiths et al., "Introduction to Genetic Analysis, 7th ed.," W. H. Freeman & Co., N.Y. (1999); and Gilbert et al., "Developmental Biology, 6th ed.," Sinauer Associates, Inc., Sunderland, Mass. (2000).

Chemistry terms used herein are used according to conventional usage in the art, as exemplified by "The McGraw- Hill Dictionary of Chemical Terms," Parker S., Ed., McGraw-Hill, San Francisco, Calif. (1985).

All of the publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to. "Including" and "including but not limited to" are used interchangeably.

A "patient," "subject," or "individual" are used interchangeably and refer to either a human or a non-human animal. These terms include mammals, such as humans, primates, livestock animals (including bovine, porcine, etc.), companion animals (e.g., canine, feline, etc.) and rodents (e.g., mice and rats).

"Cognitive function" or "cognitive status" refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, expressing an interest in one's surroundings and self-care, speed of processing, reasoning and problem solving and social cognition.

In humans, cognitive function may be assessed, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test, or the explicit 3-alternative forced choice task, or MATRICS consensus neuropsychological test battery. See Folstein et al., *J Psychiatric Res* 12: 189-98, (1975); Robbins et al., Dementia 5: 266-81, (1994); Rey, L'examen clinique en psychologie, (1964); Kluger et al., *J Geriatr Psychiatry Neurol* 12:168-79, (1999); Marquis et al., 2002 and Masur et al., 1994. Also see Buchanan, R. W., Keefe, R. S. E., Umbricht, D., Green, M. F., Laughren, T., and Marder, S. R. (2011), The FDA-NIMH-MATRICS guidelines for clinical trial design of cognitive-enhancing drugs: what do we know 5 years later-?Schizophr. Bull. 37, 1209-1217.

In animal model systems, cognitive function may be assessed in various conventional ways known in the art, including using a Morris Water Maze (MWM), Barnes circular maze, elevated radial arm maze, T maze or any other mazes in which the animals use spatial information. Cognitive function can be assessed by reversal learning, extradimensional set shifting, conditional discrimination learning and assessments of reward expectancy. Other tests known in the art may also be used to assess cognitive function, such as novel object recognition and odor recognition tasks.

Cognitive function may also be assessed using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

"Promoting" cognitive function refers to affecting impaired cognitive function so that it more closely resembles the function of a normal subject. Cognitive function may be promoted to any detectable degree, but in humans preferably is promoted sufficiently to allow an impaired subject to carry out daily activities of normal life at a level of proficiency as close as possible to a normal subject or an age-matched normal subject.

In some cases, "promoting" cognitive function in a subject affected by age-related cognitive refers to affecting impaired cognitive function so that it more closely resembles the function of an aged-matched normal subject, or the function of a young adult subject. Cognitive function of that subject may be promoted to any detectable degree, but in humans preferably is promoted sufficiently to allow an impaired subject to carry out daily activities of normal life at a level of proficiency close as possible to a normal subject or a young adult subject or an age-matched normal subject.

"Preserving" cognitive function refers to affecting normal or impaired cognitive function such that it does not decline or does not fall below that observed in the subject upon first presentation or diagnosis, or delays such decline.

"Improving" cognitive function includes promoting cognitive function and/or preserving cognitive function in a subject.

"Cognitive impairment" refers to cognitive function in subjects that is not as robust as that expected in a normal subject. In some cases, cognitive function is reduced by about 5%, about 10%, about 30%, or more, compared to cognitive function expected in a normal subject. In some cases, "cognitive impairment" in subjects affected by aged-related cognitive impairment refers to cognitive function in subjects that is not as robust as that expected in a normal subject or in an aged-matched normal subject, or a young adult subject (i.e. subjects with mean scores for a given age in a cognitive test).

"Age-related cognitive impairment" refers to cognitive impairment in aged subjects, which is thought to be a function of aging, wherein their cognitive function is not as robust as that expected in an age-matched normal subject or as that expected in young adult subjects or in a young adult subject. In some cases, cognitive function is reduced by about 5%, about 10%, about 30%, or more, as compared to cognitive function expected in an age-matched normal subject. In some cases, cognitive function is as expected in an age-matched normal subject, but reduced by about 5%, about 10%, about 30%, about 50% or more, compared to cognitive function expected in a young adult subject. Age-related impaired cognitive function may be associated with Mild Cognitive Impairment (MCI) (including amnestic MCI and non-amnestic MCI), Age-Associated Memory Impairment (AAMI), and Age-related Cognitive Decline (ARCD).

"Cognitive impairment" associated with AD or related to AD or in AD refers to cognitive function in subjects that is not as robust as that expected in subjects who have not been diagnosed with AD using conventional methodologies and standards.

"Mild Cognitive Impairment" or "MCI" refers to a condition, not necessarily age-related, characterized by isolated memory impairment unaccompanied other cognitive abnormalities and relatively normal functional abilities. One set of criteria for a clinical characterization of MCI specifies one of more of the following characteristics: (1) memory complaint (as reported by patient, informant, or physician), (2) normal activities of daily living (ADLs), (3) normal global cognitive function, (4) abnormal memory for age (defined as scoring more than 1.5 standard deviations below the mean for a given age), and (5) absence of indicators of dementia (as defined by DSM-IV guidelines). Petersen et al., *Srch. Neurol.* 56: 303-308 (1999); Petersen, "Mild cognitive impairment: Aging to Alzheimer's Disease." Oxford University Press, N.Y. (2003). The cognitive deficit in subjects with MCI may involve any cognition area or mental process including memory, language, association, attention, perception, problem solving, executive function and visuospatial skills. See, e.g., Winbald et al., *J. Intern. Med.* 256:240-240, 2004; Meguro, *Acta. Neurol. Taiwan.* 15:55-57, 2008; Ellison et al., *CNS Spectr.* 13:66-72, 2008, Petersen, *Semin. Neurol.* 27:22-31, 2007. MCI is further subdivided into amnestic MCI (aMCI) and non-amnestic MCI, characterized by the impairment (or lack thereof) of memory in particular. MCI is defined as aMCI if memory is found to be impaired given the age and education level of the subject. If, on the other hand, the memory of the subject is found to be intact for age and education, but other non-memory cognitive domains are impaired, such as language, executive function, or visuospatial skills, MCI is defined as non-amnestic MCI. aMCI and non-amnestic MCI can both be further subdivided into single or multiple domain MCI. aMCI-single domain refers to a condition where memory, but not other cognitive areas are impaired. aMCI-multiple domain refers to a condition where memory and at least one other cognitive area are impaired. Non-amnestic MCI is single domain or multiple domain dependent on whether nor not more than one non-memory cognitive area is impaired. See, e.g., Peterson and Negash, *CNS Spectr.* 13:45-53, 2008.

Diagnosis of MCI usually entails an objective assessment of cognitive impairment, which can be garnered through the use of well-established neuropsychological tests, including the Mini Mental State Examination (MMSE), the Cambridge Neuropsychological Test Automated Battery (CANTAB) and individual tests such as Rey Auditory Verbal Learning Test (AVLT), Logical Memory Subtest of the revised Wechsler Memory Scale (WMS-R) and the New York University (NYU) Paragraph Recall Test. See Folstein et al., *J Psychiatric Res* 12: 189-98 (1975); Robbins et al., *Dementia* 5: 266-81 (1994); Kluger et al., *J Geriatric Psychiatry Neurol* 12:168-79 (1999).

"Age-Associate Memory Impairment (AAMI)" refers to a decline in memory due to aging. A patient may be considered to have AAMI if he or she is at least 50 years old and meets all of the following criteria: a) The patient has noticed a decline in memory performance, b) The patient performs worse on a standard test of memory compared to young adults, c) All other obvious causes of memory decline, except normal aging, have been ruled out (in other words, the memory decline cannot be attributed to other causes such as a recent heart attack or head injury, depression, adverse reactions to medication, Alzheimer's disease, etc.).

"Age-Related Cognitive Decline (ARCD)" refers to declines in memory and cognitive abilities that are a normal consequence of aging in humans (e.g., Craik & Salthouse, 1992). This is also true in virtually all mammalian species. Age-Associated Memory Impairment refers to older persons with objective memory declines relative to their younger years, but cognitive functioning that is normal relative to their age peers (Crook et al., 1986). Age-Consistent Memory Decline is a less pejorative label which emphasizes that these are normal developmental changes (Crook, 1993; Larrabee, 1996), are not pathophysiological (Smith et al., 1991), and rarely progress to overt dementia (Youngjohn & Crook, 1993). The DSM-IV (1994) has codified the diagnostic classification of ARCD.

"Dementia" refers to a condition characterized by severe cognitive deficit that interferes in normal activities of daily living. Subjects with dementia often display other symptoms such as impaired judgment, changes in personality, disorientation, confusion, behavior changes, trouble speaking, and motor deficits. There are different types of dementias, such as Alzheimer's disease (AD), vascular dementia, dementia with Lewy bodies, and frontotemporal dementia.

Alzheimer's disease (AD) may be characterized by memory deficits in its early phase. Later symptoms may include impaired judgment, disorientation, confusion, behavior changes, trouble speaking, and motor deficits. Histologically, AD is characterized by beta-amyloid plaques and tangles of protein tau.

Vascular dementia may be caused by strokes. Symptoms overlap with those of AD, but without the focus on memory impairment.

Dementia with Lewy bodies may be characterized by abnormal deposits of alpha-synuclein that form inside neurons in the brain. Cognitive impairment may be similar to AD, including impairments in memory and judgment and behavior changes.

Frontotemporal dementia may be characterized by gliosis, neuronal loss, superficial spongiform degeneration in the frontal cortex and/or anterior temporal lobes, and Picks' bodies. Symptoms include changes in personality and behavior, including a decline in social skills and language expression/comprehension.

"Post-traumatic stress disorder (PTSD)" refers to a disorder characterized by an immediate or delayed response to a catastrophic event, characterized by re-experiencing the trauma, psychic numbing or avoidance of stimuli associated with the trauma, and increased arousal. Re-experiencing phenomena include intrusive memories, flashbacks, nightmares, and psychological or physiological distress in response to trauma reminders. Such responses produce anxiety and can have significant impact, both chronic and acute, on a patient's quality of life and physical and emotional health. PTSD is also associated with impaired cognitive performance, and older individuals with PTSD have greater decline in cognitive performance relative to control patients.

"Schizophrenia" refers to a chronic debilitating disorder, characterized by a spectrum of psychopathology, including positive symptoms such as aberrant or distorted mental representations (e.g., hallucinations, delusions), negative symptoms characterized by diminution of motivation and adaptive goal-directed action (e.g., anhedonia, affective flattening, avolition), and cognitive impairment. While abnormalities in the brain are proposed to underlie the full spectrum of psychopathology in schizophrenia, currently available antipsychotics are largely ineffective in treating cognitive impairments in patients ad may exacerbate those impairments.

"Bipolar disorder" or "BP" or "manic depressive disorder" or "manic depressive illness" refers to a chronic psychological/mood disorder which can be characterized by significant mood changes including periods of depression and euphoric manic periods. BP may be diagnosed by a skilled physician based on personal and medical history, interview consultation and physical examinations. The term "mania" or "manic periods" or other variants refers to periods where an individual exhibits some or all of the following characteristics: racing thoughts, rapid speech, elevated levels of activity and agitation as well as an inflated sense of self-esteem, euphoria, poor judgment, insomnia, impaired concentration and aggression.

"Amyotrophic lateral sclerosis," also known as ALS, refers to a progressive, fatal, neurodegenerative disease characterized by a degeneration of motor neurons, the nerve cells in the central nervous system that control voluntary muscle movement. ALS may be characterized by neuronal degeneration in the entorhinal cortex and hippocampus, memory deficits, and neuronal hyperexcitability in different brain areas such as the cortex.

"Cancer-therapy-related cognitive impairment" refers to cognitive impairment that develops in subjects that are treated with cancer therapies such as chemotherapy (e.g., chemo brain) and radiation. Cytotoxicity and other adverse side-effects on the brain of cancer therapies may result in cognitive impairment in such functions as memory, learning and attention.

Parkinson's disease (PD) is a neurological disorder that may be characterized by a decrease of voluntary movements. The afflicted patient may have reduction of motor activity and slower voluntary movements compared to the normal individual. The patient may have characteristic "mask" face, a tendency to hurry while walking, bent over posture and generalized weakness of the muscles. There is a typical "lead-pipe" rigidity of passive movements. Another important feature of the disease is the tremor of the extremities occurring at rest and decreasing during movements.

Parkinson's disease psychosis is experienced by about one third of PD patients and significantly affects the patient's quality of life. Psychosis is characterized by hallucinations, delusions, and other sensory disturbances including illusions and "sense of presence" hallucinations. The underlying cause of psychosis in PD patients is not well understood. However, the occurrence of cognitive impairment in PD patients has been identified as a risk factor associated with the development of psychosis (Laura B. Zahodne and Hubert H. Fernandez, *Drugs Aging.* 2008, 25(8), 665-682).

"Autism," as used herein, refers to an autism spectrum disorder characterized by a neural development disorder leading to impaired social interaction and communication by restricted and repetitive behavior. "Autism Spectrum Disorder" refers to a group of developmental disabilities that include: autism; Asperger syndrome; pervasive developmental disorder not otherwise specified (PDD-NOS or atypical autism); Rett syndrome; and childhood disintegrative disorder.

Mental retardation is a generalized disorder characterized by significantly impaired cognitive function and deficits in adaptive behaviors. Mental retardation is often defined as an Intelligence Quotient (IQ) score of less than 70. Inborn causes are among many underlying causes for mental retardation. The dysfunction in neuronal communication is also considered one of the underlying causes for mental retardation (Myrrhe van Spronsen and Casper C. Hoogenraad, *Curr. Neurol. Neurosci. Rep.* 2010, 10, 207-214).

In some instances, mental retardation includes, but are not limited to, Down syndrome, velocariofacial syndrome, fetal alcohol syndrome, Fragile X syndrome, Klinefelter's syndrome, neurofibromatosis, congenital hypothyroidism, Williams syndrome, phenylketonuria (PKU), Smith-Lemli-Opitz syndrome, Prader-Willi syndrome, Phelan-McDermid syndrome, Mowat-Wilson syndrome, ciliopathy, Lowe syndrome and siderium type X-linked mental retardation. Down syndrome is a disorder that includes a combination of birth defects, including some degree of mental retardation, characteristic facial features and, often, heart defects, increased infections, problems with vision and hearing, and other health problems. Fragile X syndrome is a prevalent form of inherited mental retardation, occurring with a frequency of 1 in 4,000 males and 1 in 8,000 females. The syndrome is also characterized by developmental delay, hyperactivity, attention deficit disorder, and autistic-like behavior. There is no effective treatment for fragile X syndrome.

Obsessive compulsive disorder ("OCD") is a mental condition that is most commonly characterized by intrusive, repetitive unwanted thoughts (obsessions) resulting in compulsive behaviors and mental acts that an individual feels driven to perform (compulsion). Current epidemiological data indicates that OCD is the fourth most common mental disorder in the United States. Some studies suggest the prevalence of OCD is between one and three percent, although the prevalence of clinically recognized OCD is much lower, suggesting that many individuals with the disorder may not be diagnosed. Patients with OCD are often diagnosed by a psychologist, psychiatrist, or psychoanalyst according to the Diagnostic and Statistical Manual of Mental Disorders, 4th edition text revision (DSM-IV-TR) (2000) diagnostic criteria that include characteristics of obsessions and compulsions.

Substance addiction (e.g., drug addiction, alcohol addiction) is a mental disorder. The addiction is not triggered instantaneously upon exposure to the substance. Rather, it involves multiple, complex neural adaptations that develop with different time courses ranging from hours to days to months (Kauer J. A. *Nat. Rev. Neurosci.* 2007, 8, 844-858). The path to addiction generally begins with the voluntary use of one or more controlled, or other substances, such as narcotics, barbiturates, methamphetamines, alcohol, nicotine, and any of a variety of other such substances. Over time, with extended use of the substance(s), the voluntary ability to abstain from the substance(s) is compromised due to the effects of prolonged use on brain function, and thus on behavior. As such, substance addiction generally is characterized by compulsive substance craving, seeking and use that persist even in the face of negative consequences. The cravings may represent changes in the underlying neurobiology of the patient which likely must be addressed in a meaningful way if recovery is to be obtained. Substance addiction is also characterized in many cases by withdrawal symptoms, which for some substances are life threatening (e.g., alcohol, barbiturates) and in others can result in substantial morbidity (which may include nausea, vomiting, fever, dizziness, and profuse sweating), distress, and decreased ability to obtain recovery. For example, alcoholism, also known as alcohol dependence, is one such substance addiction. Alcoholism is primarily characterized by four symptoms, which include cravings, loss of control, physical dependence and tolerance. These symptoms also may characterize addictions to other substances. The craving for alcohol, as well as other substances, often is as strong as the need for food or water. Thus, an alcoholic may continue to drink despite serious family, health and/or legal ramifications.

Brain cancer is the growth of abnormal cells in the tissues of the brain usually related to the growth of malignant brain tumors. Brain tumors grow and press on the nearby areas of the brain which can stop that part of the brain from working the way it should. Brain cancer rarely spreads into other tissues outside of the brain. The grade of tumor, based on how abnormal the cancer cells look under a microscope, may be used to tell the difference between slow- and fast-growing tumors. Brain tumors are classified according to the kind of cell from which the tumor seems to originate. Diffuse, fibrillary astrocytomas are the most common type of primary brain tumor in adults. These tumors are divided histopathologically into three grades of malignancy: World Health Organization (WHO) grade II astrocytoma, WHO grade III anaplastic astrocytoma and WHO grade IV glioblastoma multiforme (GBM). WHO grade II astocytomas are the most indolent of the diffuse astrocytoma spectrum. Astrocytomas display a remarkable tendency to infiltrate the surrounding brain, confounding therapeutic attempts at local control. These invasive abilities are often apparent in low-grade as well as high-grade tumors.

Glioblastoma multiforme is the most malignant stage of astrocytoma, with survival times of less than 2 years for most patients. Histologically, these tumors are characterized by dense cellularity, high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

There are biologic subsets of astrocytomas, which may reflect the clinical heterogeneity observed in these tumors. These subsets include brain stem gliomas, which are a form of pediatric diffuse, fibrillary astrocytoma that often follow a malignant course. Brain stem GBMs share genetic features with those adult GBMs that affect younger patients. Pleomorphic xanthoastrocytoma (PXA) is a superficial, low-grade astrocytic tumor that predominantly affects young adults. While these tumors have a bizarre histological appearance, they are typically slow-growing tumors that may be amenable to surgical cure. Some PXAs, however, may recur as GBM. Pilocytic astrocytoma is the most common astrocytic tumor of childhood and differs clinically and histopathologically from the diffuse, fibrillary astrocytoma that affects adults. Pilocytic astrocytomas do not have the same genomic alterations as diffuse, fibrillary astrocytomas. Subependymal giant cell astrocytomas (SEGA) are periventricular, low-grade astrocytic tumors that are usually associated with tuberous sclerosis (TS), and are histologically identical to the so-called "candle-gutterings" that line the ventricles of TS patients. Similar to the other tumorous lesions in TS, these are slowly-growing and may be more akin to hamartomas than true neoplasms. Desmoplastic cerebral astrocytoma of infancy (DCAI) and desmoplastic infantile ganglioglioma (DIGG) are large, superficial, usually cystic, benign astrocytomas that affect children in the first year or two of life.

Oligodendrogliomas and oligoastrocytomas (mixed gliomas) are diffuse, usually cerebral tumors that are clinically and biologically most closely related to the diffuse, fibrillary astrocytomas. The tumors, however, are far less common than astrocytomas and have generally better prognoses than the diffuse astrocytomas. Oligodendrogliomas and oligoastrocytomas may progress, either to WHO grade III anaplastic oligodendroglioma or anaplastic oligoastrocytoma, or to WHO grade IV GBM. Thus, the genetic changes that lead to oligodendroglial tumors constitute yet another pathway to GBM.

Ependymomas are a clinically diverse group of gliomas that vary from aggressive intraventricular tumors of children to benign spinal cord tumors in adults. Transitions of ependymoma to GBM are rare. Choroid plexus tumors are also a varied group of tumors that preferentially occur in the ventricular system, ranging from aggressive supratentorial intraventricular tumors of children to benign cerebellopontine angle tumors of adults. Choroid plexus tumors have been reported occasionally in patients with Li-Fraumeni syndrome and von Hippel-Lindau (VHL) disease.

Medulloblastomas are highly malignant, primitive tumors that arise in the posterior fossa, primarily in children. Medulloblastoma is the most common childhood malignant brain tumor. The most lethal medulloblastoma subtype exhibits a high expression of the $GABA_A$ receptor α5 subunit gene and MYC amplification. See, e.g., J Biomed Nanotechnol. 2016 June; 12(6):1297-302.

Meningiomas are common intracranial tumors that arise in the meninges and compress the underlying brain. Meningiomas are usually benign, but some "atypical" meningiomas may recur locally, and some meningiomas are frankly malignant and may invade the brain or metastasize. Atypical and malignant meningiomas are not as common as benign meningiomas. Schwannomas are benign tumors that arise on peripheral nerves. Schwannomas may arise on cranial nerves, particularly the vestibular portion of the eighth cranial nerve (vestibular schwannomas, acoustic neuromas) where they present as cerebellopontine angle masses. Hemangioblastomas are tumors of uncertain origin that are composed of endothelial cells, pericytes and so-called stromal cells. These benign tumors most frequently occur in the cerebellum and spinal cord of young adults. Multiple hemangioblastomas are characteristic of von Hippel-Lindau disease (VHL). Hemangiopericytomas (HPCs) are dural tumors which may display locally aggressive behavior and may metastasize. The histogenesis of dural-based hemangiopericytoma (HPC) has long been debated, with some authors classifying it as a distinct entity and others classifying it as a subtype of meningioma.

"Treating cognitive impairment" refers to taking steps to improve cognitive function in a subject with cognitive impairment so that the subject's performance in one or more cognitive tests is improved to any detectable degree, or is prevented from further decline. Preferably, that subject's cognitive function, after treatment of cognitive impairment, more closely resembles the function of a normal subject. Treatment of cognitive impairment in humans may improve cognitive function to any detectable degree but is preferably improved sufficiently to allow the impaired subject to carry out daily activities of normal life at the same level of proficiency as a normal subject. In some cases, "treating cognitive impairment" refers to taking steps to improve cognitive function in a subject with cognitive impairment so that the subject's performance in one or more cognitive tests is improved to any detectable degree or is prevented from further decline. Preferably, that subject's cognitive function, after treatment of cognitive impairment, more closely resembles the function of a normal subject. In some cases, "treating cognitive impairment" in a subject affected by age-related cognitive impairment refers to taking steps to improve cognitive function in the subject so that the subject's cognitive function, after treatment of cognitive impairment, more closely resembles the function of an age-matched normal subject, or the function of a young adult subject. Beneficial or desired clinical results for treating cognitive impairment include, but are not limited to, preventing, delaying or slowing the progression of the cognitive impairment; reducing the rate of decline of cognitive function in a subject suffering from cognitive impairment; or alleviating, ameliorating, or slowing the progression, of one or more symptoms of the cognitive impairment associated with CNS disorders, such as age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. Treating age-related cognitive impairment further comprises slowing the conversion of age-related cognitive impairment (including, but not limited to MCI, ARCD and AAMI) into dementia (e.g., AD).

"Treating brain cancer" refers to preventing or slowing the progression of brain cancers. In certain embodiments, treatment comprises alleviation, amelioration, or slowing the progression of one or more symptoms associated with brain cancers. In certain embodiments, the symptom to be treated is cognitive impairment. For example, methods and compositions of the disclosure can be used to treat the cognitive impairment and/or to improve cognitive function in patients with brain cancers. In some embodiments of the invention, there is provided a method of preserving or improving cognitive function in a subject with brain cancers, the method comprising the step of administering to said subject a therapeutically effective amount of a compound of the invention or a pharmaceutically acceptable salt, hydrate, solvate, polymorph, isomer, or combination thereof. In some embodiments, the brain tumor is medulloblastoma.

"Administering" or "administration of" a compound, composition, combination, or crystalline form of a compound to a subject can be carried out using one of a variety of methods known to those skilled in the art. For example, a compound, composition, combination, or crystalline form of a compound can be administered, intravenously, arterially, intradermally, intramuscularly, intraperitoneally, intravenously, subcutaneously, ocularly, sublingually, orally (by ingestion), intranasally (by inhalation), intraspinally, intracerebrally, and transdermally (by absorption, e.g., through a skin duct). A compound, composition, combination, or crystalline form of a compound can also appropriately be introduced by rechargeable or biodegradable polymeric devices or other devices, e.g., patches and pumps, or formulations, which provide for the extended, slow, or controlled release of the compound or agent. Administering can also be performed, for example, once, a plurality of times, and/or over one or more extended periods. In some aspects, the administration includes both direct administration, including self-administration, and indirect administration, including the act of prescribing a compound, composition, combination, or crystalline form of a compound. For example, as used herein, a physician who instructs a patient to self-administer a compound, composition, combination, or crystalline form of a compound, or to have the compound, composition, combination, or crystalline form of a compound administered by another and/or who provides a patient with a prescription for a drug is administering the compound, composition, combination, or crystalline form of a compound to the patient.

Appropriate methods of administering a compound, composition, combination, or crystalline form of a compound to a subject will also depend, for example, on the age of the subject, whether the subject is active or inactive at the time of administering, whether the subject is cognitively impaired at the time of administering, the extent of the impairment, and the chemical and biological properties of the a compound, composition, combination, or crystalline form of a compound (e.g. solubility, digestibility, bioavailability, stability and toxicity). In some embodiments, a compound, composition, combination, or crystalline form of a compound is administered orally, e.g., to a subject by ingestion, or intravenously, e.g., to a subject by injection. In some embodiments, the orally administered compound, composition, combination, or crystalline form of a compound is in an extended release or slow release formulation, or administered using a device for such slow or extended release.

As used herein, a "α5-containing $GABA_A$ receptor agonist," "α5-containing $GABA_A$R agonist" or a "$GABA_A$ α5 receptor agonist" and other variations as used herein refers to a compound that enhances the function of α5-containing $GABA_A$ receptor ($GABA_A$ R), i.e., a compound that increase GABA-gated $Cl^-$ currents. In some embodiments, α5-containing $GABA_A$ R agonist as used herein refers to a positive allosteric modulator, which potentiates the activity of GABA. α5-containing $GABA_A$ receptor agonists, suitable for use in the present disclosure, include the α5-containing $GABA_A$ receptor agonists of all formulas and specific α5-containing $GABA_A$ receptor agonists described herein, and their hydrates, solvates, polymorphs, salts (e.g., pharmaceutically acceptable salts), isomers (e.g., stereoisomers, E/Z isomers, and tautomers), and combinations thereof.

"Antipsychotic", "antipsychotic agent", "antipsychotic drug", or "antipsychotic compound" refers to (1) a typical or an atypical antipsychotic; (2) an agent that is selected from dopaminergic agents, glutamatergic agents, NMDA receptor positive allosteric modulators, glycine reuptake inhibitors, glutamate reuptake inhibitor, metabotropic glutamate receptors (mGluRs) agonists or positive allosteric modulators (PAMs) (e.g., mGluR2/3 agonists or PAMs), glutamate receptor glur5 positive allosteric modulators (PAMs), M1 muscarinic acetylcholine receptor (mAChR) positive allosteric modulators (PAMs), histamine H3 receptor antagonists, AMPA/kainate receptor antagonists, ampakines (CX-516), glutathione prodrugs, noradrenergic agents, serotonin receptor modulators, cholinergic agents, cannabinoid CB1 antagonists, neurokinin 3 antagonists, neurotensin agonists, MAO B inhibitors, PDE10 inhibitors, nNOS inhibits, neurosteroids, and neurotrophic factors, alpha-7 agonists or positive allosteric modulators (PAMs) PAMs, serotonin 2C agonists; and/or (3) an agent that is useful in treating one or more signs or symptoms of schizophrenia or bipolar disorder (in particular, mania).

"Typical antipsychotics", as used herein, refers to conventional antipsychotics, which produce antipsychotic effects as well as movement related adverse effects related to disturbances in the nigrostriatal dopamine system. These extrapyramidal side effects (EPS) include Parkinsonism, akathisia, tardive dyskinesia and dystonia. See Baldessarini and Tarazi in Goodman & Gilman's The Pharmacological Basis of Therapeutics 10 Edition, 2001, pp. 485-520.

"Atypical antipsychotics", as used herein, refers to antipsychotic drugs that produce antipsychotic effects with little or no EPS and include, but are not limited to, aripiprazole, asenapine, clozapine, iloperidone, olanzapine, lurasidone, paliperidone, quetiapine, risperidone and ziprasidone. "Atypical" antipsychotics differ from conventional antipsychotics in their pharmacological profiles. While conventional antipsychotics are characterized principally by $D_2$ dopamine receptor blockade, atypical antipsychotics show antagonist effects on multiple receptors including the $5HT_a$ and $5HT_c$ serotonin receptors and varying degrees of receptor affinities. Atypical antipsychotic drugs are commonly referred to as serotonin/dopamine antagonists, reflecting the influential hypothesis that greater affinity for the $5HT_2$ receptor than for the $D_2$ receptor underlies "atypical" antipsychotic drug action or "second generation" antipsychotic drugs. However, the atypical antipsychotics often display side effects, including, but not limited to, weight gain, diabetes (e.g., type II diabetes mellitus), hyperlipidemia, QTc interval prolongation, myocarditis, sexual side effects, extrapyramidal side effects and cataract. Thus, atypical antipsychotics do not represent a homogeneous class, given their differences in the context of both alleviation of clinical symptoms and their potential for inducing side effects such as the ones listed above. Further, the common side effects of the atypical antipsychotics as described above often limit the antipsychotic doses that can be used for these agents.

In some embodiments of this disclosure, the SV2A inhibitor is levetiracetam, or a pharmaceutically acceptable salt, hydrate, solvate, polymorph, or isomer thereof. Levetiracetam refers to the compound (2S)-2-(2-oxopyrrolidin-1-yl) butanamide (International Union of Pure and Applied Chemistry (IUPAC) name). Levetiracetam is sold as the FDA approved antiepileptic drug KEPPRA. Typically, the therapeutically effective dose of levetiracetam (KEPPRA) is in a range of 1000-3000 mg/day. Levetiracetam is a widely used antiepileptic drug. Levetiracetam binds to a specific site in the CNS: the synaptic vesicle protein 2A (SV2A) (See, e.g., Noyer et al. 1995; Fuks et al. 2003; Lynch et al. 2004; Gillard et al. 2006) and has further been shown to directly inhibit synaptic activity and neurotransmission by inhibiting presynaptic neurotransmitter release (Yang et al., 2007).

In some embodiments of this disclosure, the SV2A inhibitor is brivaracetam (sold under the name BRIVIAC, or a pharmaceutically acceptable salt, hydrate, solvate, polymorph, or isomer thereof. Brivaracetam refers to the compound (2S)-2-[(4R)-2-oxo-4-propylpyrrolidin-1-yl]butanamide (IUPAC name). It has anticonvulsant activity and binds to SV2A in the brain.

In some embodiments of this disclosure, the SV2A inhibitor is seletracetam, or a pharmaceutically acceptable salt, hydrate, solvate, polymorph, or isomer thereof. Seletracetam refers to the compound (2S)-2-[(4S)-4-(2,2-difluoroethenyl)-2-oxopyrrolidin-1-yl]butanamide (IUPAC name). It is an antiepileptic agent and binds to SV2A in the brain.

Various studies have shown that SV2A inhibitors, compounds that bind to SV2A and reduce synaptic function by reducing pre-synaptic vesicle release (See, e.g., Noyer et al. 1995; Fuks et al. 2003; Lynch et al. 2004; Gillard et al. 2006; Custer et al., 2006; Smedt et al., 2007; Yang et al., 2007; Meehan, "Levetiracetam has an activity-dependent effect on inhibitory transmission," *Epilepsia,* 2012 Jan. 31; and Example 8 of WO 2001/62726, all of which are specifically incorporated herein by reference.), may be effective in the treatment of cognitive impairment associated with CNS disorders in a narrow, low dose range. See, e.g., International Patent Application PCT/US2009/005647 (Pub. No. WO2010/044878), International Patent Application PCT/US2011/024256 (Pub. No. WO2011/100373), International Patent Application PCT/US2012/024556 (Pub. No. WO2012/109491), International Patent Application PCT/US2013/070144 (Pub. No. WO2014/078568), International Patent Application PCT/US2014/029170 (Pub. No. WO2014/144663), International Patent Application PCT/US2014/029362 (Pub. No. WO2014/144801), and International Patent Application PCT/US2016/033567 (Pub. No. WO2016/191288), all of which are specifically incorporated herein by reference.

Memantine is chemically known as 3,5-dimethyladamantan-1-amine or 3,5-dimethyltricyclo[3.3.1.$1^{3,7}$]decan-1-amine, which is an uncompetitive N-methyl-D-aspartate (NMDA) receptor antagonist with moderate affinity. The proprietary names for memantine include: Axura® and Akatinol® (Merz), Namenda® (Forest Laboratories), Ebixa® and Abixa® (Lundbeck), and Memox® (Unipharm). Memantine is approved for the treatment of moderate to severe Alzheimer's disease (AD) in the United States at a dose of up to 28 mg/day. Derivatives or analogs of memantine, which include compounds that structurally or chemically resemble memantine, are also useful in the present disclosure. Such derivatives or analogs of memantine include, but are not limited to those compounds disclosed in U.S. Pat. Nos. 3,391,142; 4,122,193; 4,273,774; and 5,061,703; U.S. Patent Application Publication US20040087658, US20050113458, US20060205822, US20090081259, US20090124659, and US20100227852; EP Patent Application Publication EP2260839A2; EP Patent EP1682109B1; and PCT Application Publication WO2005079779, all of which are incorporated herein by reference. Memantine, as used in the present disclosure, includes memantine and its derivatives and analogs, as well as hydrates, polymorphs, prodrugs, salts, and solvates thereof. Memantine, as used herein, also includes a composition comprising memantine or a derivative or an analog or a pharmaceutically acceptable salt, hydrate, solvate, polymorph, or prodrug thereof, wherein the composition optionally further comprises at least one additional therapeutic agent (such as a therapeutic agent useful for treating a CNS disorder or cognitive impairments associated thereof). In some embodiments, the memantine composition suitable for use in the present disclosure comprises memantine and a second therapeutic agent that is donepezil (under the trade name ARICEPT).

"Acetylcholinesterase inhibitor" or "AChEI" as used herein refers to an agent that inhibits the ability of the cholinesterase enzyme to break down the neurotransmitter acetylcholine, thereby increasing the concentration and duration of acetylcholine, mainly in brain synapses or neuromuscular junctions. AChEIs suitable for use in this application may include, for example, the subcategories of (i) reversible non-competitive inhibitors or reversible competitive inhibitors, (ii) irreversible, and (iii) quasi-irreversible inhibitors. ARICEPT (donepezil) is one example of an AChEI. Other non-limiting examples include rivastigmine, galantamine (RAZADYNE) and ambenonium (MYTELASE).

The term "simultaneous administration," as used herein, may means that a α5-containing $GABA_A$ receptor agonist (e.g., a α5-containing $GABA_A$ receptor positive allosteric modulator), or a crystalline form thereof, and a second therapeutic agent (e.g., an antipsychotic, memantine or an AChEI), or their pharmaceutically acceptable salts, hydrates, solvates, or polymorphs, are administered with a time separation of no more than about 15 minutes, and in some embodiments no more than about 10 minutes. When the drugs are administered simultaneously, the α5-containing $GABA_A$ receptor agonist (e.g., an α5-containing $GABA_A$ receptor positive allosteric modulator), or a crystalline form thereof, and a second therapeutic agent (e.g., an antipsychotic, memantine or an AChEI), or their salts, hydrates, solvates, or polymorphs, may be contained in the same dosage (e.g., a unit dosage form comprising both the α5-containing $GABA_A$ receptor agonist (e.g., an α5-containing $GABA_A$ receptor positive allosteric modulator) and a second therapeutic agent (e.g., an antipsychotic, memantine or an AChEI) or in discrete dosages (e.g., the α5-containing $GABA_A$ receptor agonist (e.g., an α5-containing $GABA_A$ receptor positive allosteric modulator) or its salt, hydrate, solvate, or polymorph is contained in one dosage form and a second therapeutic agent (e.g., an antipsychotic, memantine or an AChEI), or its salt, hydrate, solvate, or polymorph is contained in another dosage form).

The term "sequential administration" as used herein means that the α5-containing $GABA_A$ receptor agonist (e.g., a α5-containing $GABA_A$ receptor positive allosteric modulator), or a crystalline form thereof, and a second therapeutic agent (e.g., an antipsychotic, memantine or an AChEI), or their pharmaceutically acceptable salts, hydrates, solvates, polymorphs, are administered with a time separation of more than about 15 minutes, and in some embodiments more than about one hour, or up to 12-24 hours. Either the α5-containing $GABA_A$ receptor agonist (e.g., a α5-containing $GABA_A$ receptor positive allosteric modulator), or a crystalline form thereof, or a second therapeutic agent (e.g., an antipsychotic, memantine or an AChEI) may be administered first. The α5-containing $GABA_A$ receptor agonist (e.g., a α5-containing $GABA_A$ receptor positive allosteric modulator), or a crystalline form thereof, and a second therapeutic agent (e.g., an antipsychotic, memantine or an AChEI), or their salts, hydrates, solvents, or polymorphs, for sequential administration may be contained in discrete dosage forms, optionally contained in the same container or package.

A "therapeutically effective amount" of a drug or agent is an amount of a drug or an agent that, when administered to a subject will have the intended therapeutic effect, e.g. improving cognitive function in a subject, e.g., a patient having cognitive impairment associated with a CNS disorder. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of the cognitive impairment or other symptoms of the CNS disorder (such as age-related cognitive impairment, Mild Cognitive Impairment (MCI), dementia, Alzheimer's Disease (AD), prodromal AD, post-traumatic stress disorder (PTSD), schizophrenia, bipolar, ALS, cancer-therapy-related cognitive impairment, mental retardation, Parkinson's disease (PD), autism spectrum disorders, fragile X disorder, Rett syndrome, compulsive behavior, and substance addiction), and the therapeutics or combination of therapeutics selected for administration, and the mode of administration. The skilled worker can readily determine the effective amount for a given situation by routine experimentation.

The term "pharmaceutical combination" refers to a drug product containing two active agents either together (i.e., in one formulation), or separately (i.e., as two separate formulations). The active agents in the pharmaceutical combination can be administered simultaneously or sequentially. The two active agents can be administered using the same method, i.e., intraperitoneally, orally, etc., or by different methods. For example, one agent can be administered using one method, e.g., orally, and the other can be administered using a different method, e.g., intraperitoneally.

The various CNS disorders associated with cognitive impairment (e.g., age-related cognitive impairment (including age-related Mild Cognitive Impairment) Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction) may have a variety of etiologies. However, the symptom of cognitive impairment in each of the above-mentioned disorders may have overlapping causes. Thus, a composition or method of treatment that treats cognitive impairment associated with in one CNS disorder may also treat cognitive impairment associated with another.

As used herein, the term "crystalline form" refers to an anhydrate, hydrate, solvate or salt form of Compound 1.

As used herein, the term "hydrate" refers to a combination of water with a compound according to this disclosure, wherein the water is either absorbed, adsorbed or contained within a crystal lattice of the substrate compound.

As used herein, the term "solvate" refers to a combination of a solvent with a compound according to this disclosure, wherein the solvate is either absorbed, adsorbed or contained within a crystal lattice of the compound.

As used herein, the term "anhydrous" refers to a form of a compound according to this disclosure that is completely without solvent, e.g., no solvent molecules are contained within the crystal lattice of the compound.

As used herein, the term "polymorph" refers to different crystalline forms of the same compound and other solid state molecular forms including pseudo-polymorphs, such as hydrates (e.g., bound water present in the crystalline structure) and solvates (e.g., bound solvents other than water) of the same compound. Different crystalline polymorphs have different crystal structures due to a different packing of the molecules in the lattice. This results in a different crystal symmetry and/or unit cell parameters which directly influences its physical properties such the X-ray diffraction characteristics of crystals or powders. A different polymorph, for example, will in general diffract at a different set of angles and will give different values for the intensities. Therefore, X-ray powder diffraction can be used to identify or distinguish different polymorphs, or a solid form that comprises more than one polymorph, in a reproducible and reliable way. Crystalline polymorphic forms are of interest to the pharmaceutical industry and especially to those involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since Impurities present may produce undesired toxicological effects. Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies.

Compounds According to the Disclosure

In some aspects, this disclosure is directed to Compound 1, having the structure,

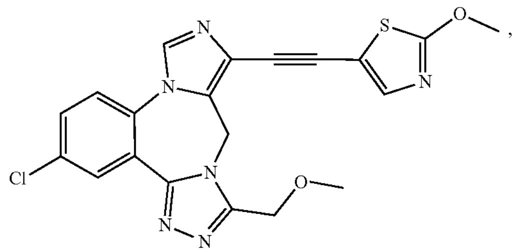 [SMILES: COCc1nnc2n1Cc1c(C#Cc3cnc(OC)s3)ncn1-c1ccc(Cl)cc1-2]

and its amorphous forms, salt forms, anhydrous forms, and solvated forms. Compound 1 is a $GABA_A$ α5 positive allosteric modulator, and is useful for treating cognitive impairment associated with a CNS disorder in a subject in need or at risk thereof, and/or slowing the progression of cognitive impairment in a subject in need or at risk thereof, and/or reducing the rate of decline of cognitive function in a subject in need or at risk thereof (see WO 2019/246300). Compound 1 is also useful in the treatment of a brain cancer, cognitive impairment associated with a brain cancer, and Parkinson's disease psychosis.

In some instances, it is desirable to use an amorphous form of Compound 1 for improved solubility and bioavailability properties. In other instances, it is desirable to use a crystalline form of Compound 1 for improved stability.

Compound 1 has been found to exist in at least 5 crystalline polymorphic forms (i.e., Form A, Form B, Form C, Material D, Form E and Form F). In some embodiments, the disclosure is directed to a crystalline form of Compound 1, wherein the crystalline form corresponds to Form A, Form B, Form C, Material D, Form E or Form F, or any mixtures thereof. In some embodiments, this disclosure is directed to an anhydrous crystalline form of Compound 1, wherein the crystalline form corresponds to Form A, Form B, Material D or Form E. In some embodiments, this disclosure is directed to a solvated crystalline form of Compound 1, wherein the crystalline form corresponds to Form C or Form F. In certain such embodiments, the solvated crystalline form of Compound 1 is a methanolate or a hydrate.

Salt forms of Compound 1 are also contemplated by this disclosure. The $pK_a$ value of Compound 1 (free base) is 1.16±0.04. Thus, salt forms can be achieved by reacting the free base form of Compound 1 with a suitable strong acid, e.g., hydrochloric, sulfuric, benzenesulfonic, ethane-1,2-disulfonic, methanesulfonic, naphthalene-1,5-disulfonic, naphthalene-2-sulfonic and toluenesulfonic. In some embodiments, this disclosure is directed to a crystalline salt form of Compound 1, wherein the salt is a hydrochloride, besylate, mesylate, napadisylate, napsylate, sulfate or tosylate salt. Additional salt forms can be achieved using other strong acids known to those skilled in the art.

In some embodiments, the crystalline form of compound 1 is Form A and exhibits an XRPD pattern comprising at least one peak selected from 3.0, and 21.0 degrees 2θ±0.2 degrees 2θ.

In some embodiments, the crystalline form of compound 1 is Form A and exhibits an XRPD pattern further comprising at least one additional peak selected from the group consisting of 9.1, 10.7, 13.8, 22.0, 23.1, 23.9, 24.4, and 27.1 degrees 2θ±0.2 degrees 2θ.

Figure 3A:
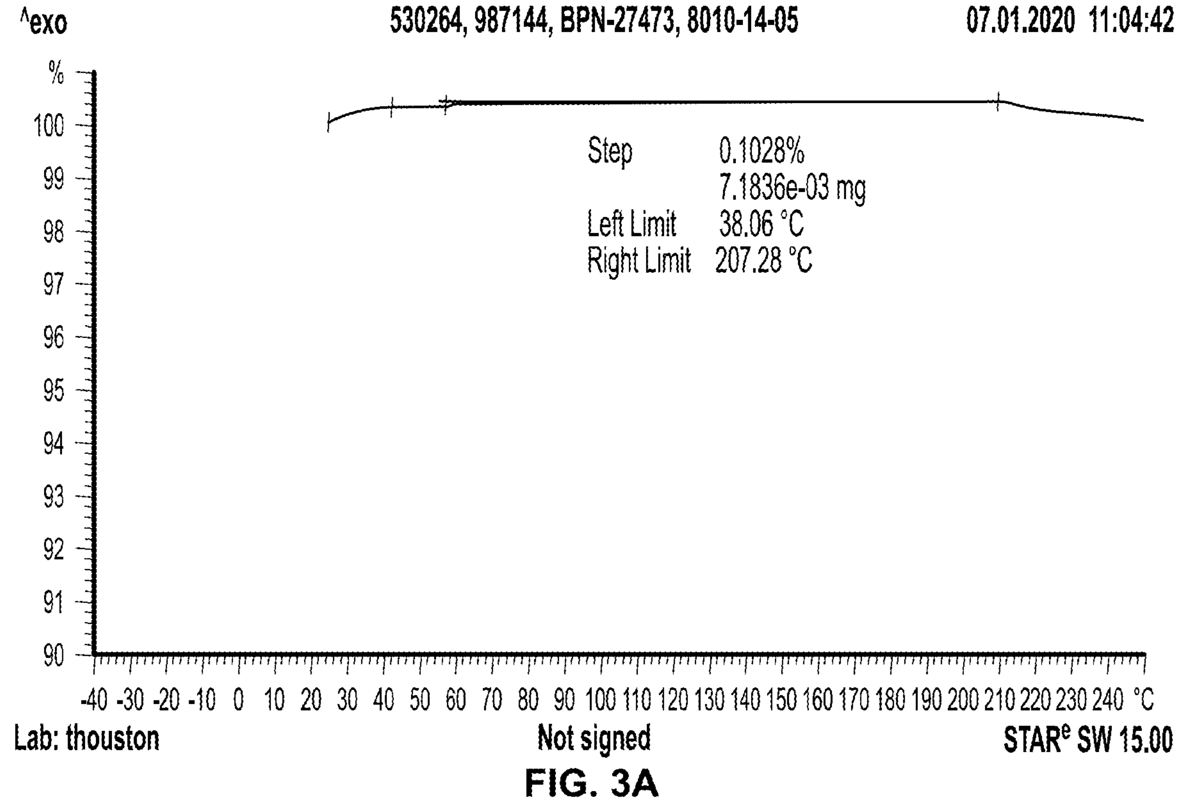
FIGS. 3A and 3B depict the thermograms of anhydrous Form A.
Figure 3B:
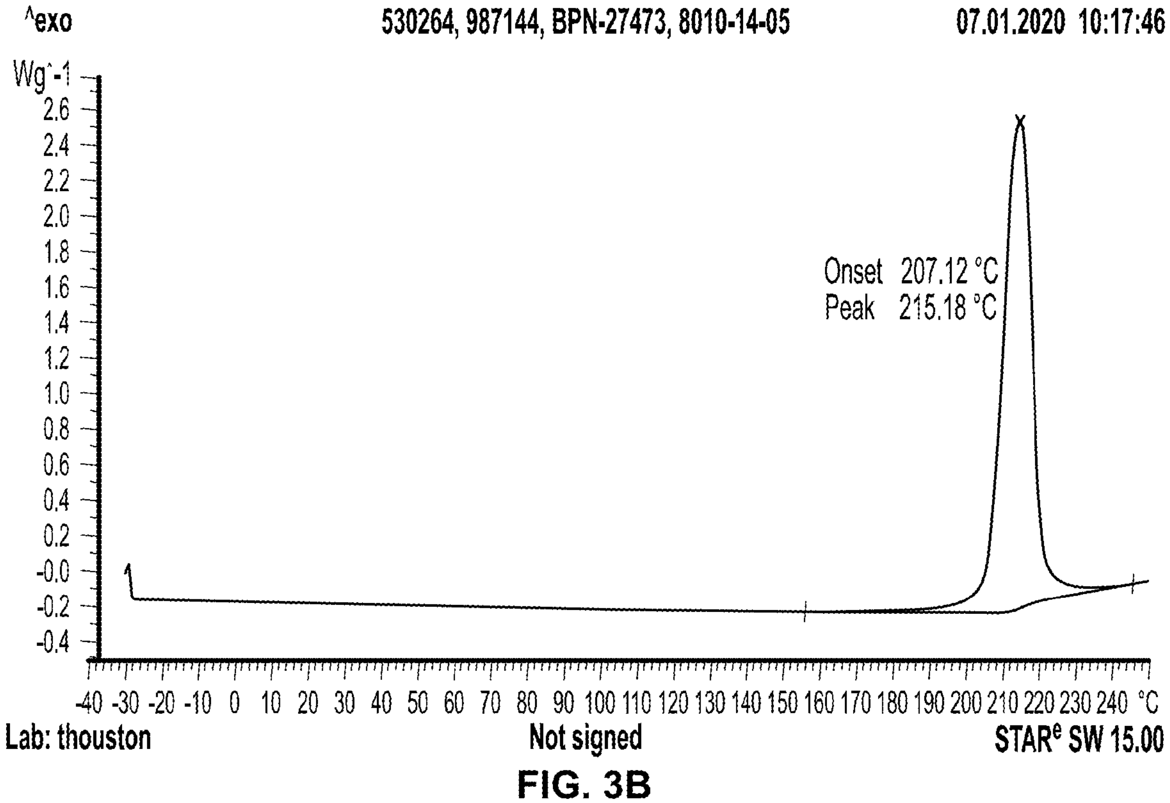
Figure 5:
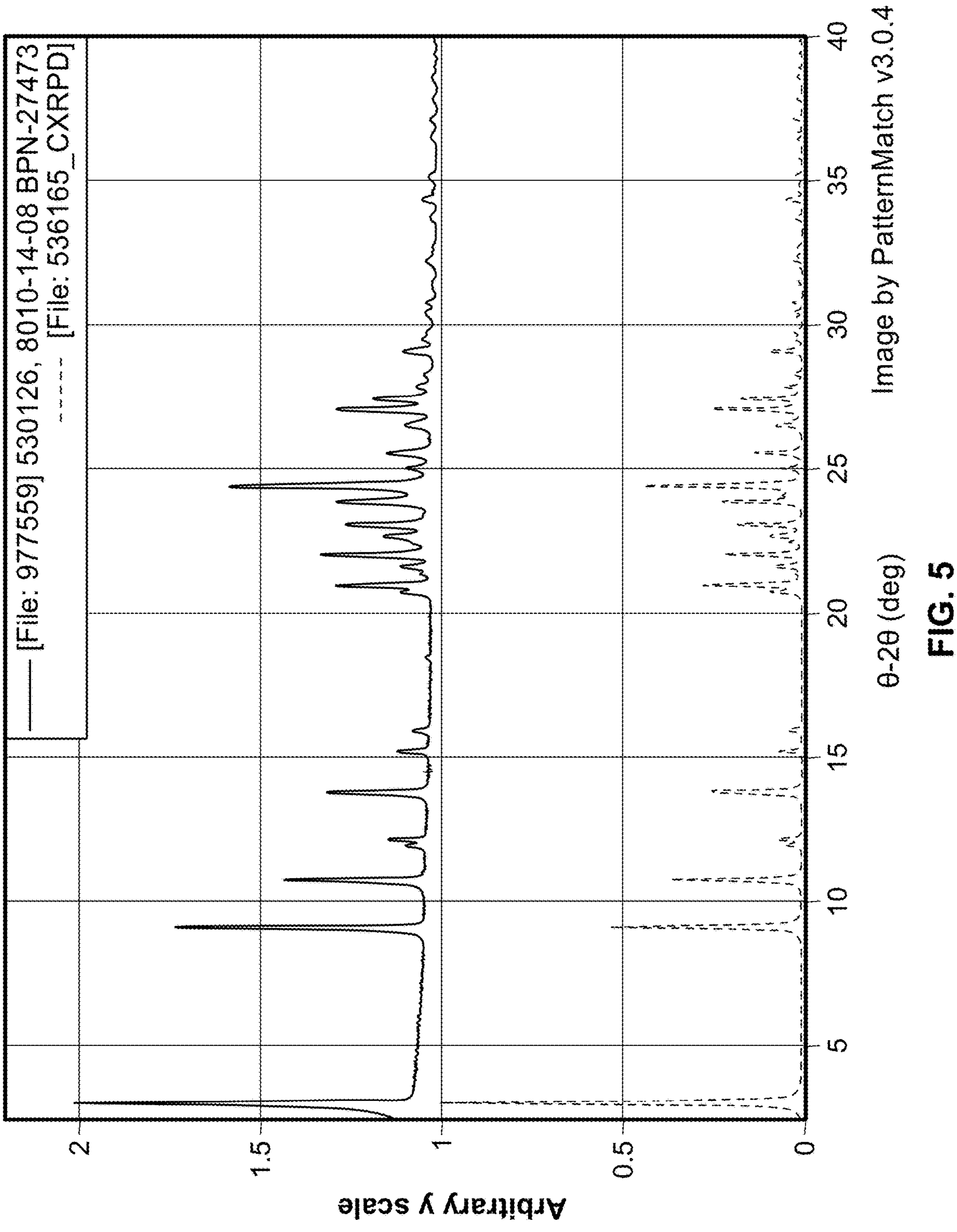
FIG. 5 is an XRPD overlay of the experimental (top) and calculated (bottom) patterns for anhydrous Form A.

In some embodiments, this disclosure provide a crystalline form of Compound 1, wherein the crystalline form is anhydrous. In some embodiments, the crystalline form of Compound 1 is Form A. In some embodiments, crystalline Form A is characterized by one or more of:

a. an x-ray powder diffraction (XRPD) pattern substantially as set forth in FIG. 5;
b. a C2/c single crystal x-ray diffraction space group;
c. a single crystal x-ray diffraction unit cell having the parameters: a=58.1415(14) Å, b=4.03974(8) Å, c=17.1204(3) Å, α=90°, β=90.261(2)°, γ=90°, V=4021.15(14) $Å^3$;
d. a differential scanning calorimetry (DSC) curve substantially as set forth in FIG. 3B; and
e. a differential scanning calorimetry (DSC) curve having an exotherm with an onset at about 207° C.

In some embodiments, crystalline Form A is characterized by two or more of:

a. an x-ray powder diffraction (XRPD) pattern substantially as set forth in FIG. 5;
b. a C2/c single crystal x-ray diffraction space group;
c. a single crystal x-ray diffraction unit cell having the parameters: a=58.1415(14) Å, b=4.03974(8) Å, c=17.1204(3) Å, α=90°, β=90.261(2)°, γ=90°, V=4021.15(14) $Å^3$;
d. a differential scanning calorimetry (DSC) curve substantially as set forth in FIG. 3B; and
e. a differential scanning calorimetry (DSC) curve having an exotherm with an onset at about 207° C.

In some embodiments, crystalline Form A is characterized by three or more of:

a. an x-ray powder diffraction (XRPD) pattern substantially as set forth in FIG. 5;
b. a C2/c single crystal x-ray diffraction space group;
c. a single crystal x-ray diffraction unit cell having the parameters: a=58.1415(14) Å, b=4.03974(8) Å, c=17.1204(3) Å, α=90°, β=90.261(2)°, γ=90°, V=4021.15(14) $Å^3$;
d. a differential scanning calorimetry (DSC) curve substantially as set forth in FIG. 3B; and
e. a differential scanning calorimetry (DSC) curve having an exotherm with an onset at about 207° C.

In some embodiments, crystalline Form A is characterized by the following properties:

a. an x-ray powder diffraction (XRPD) pattern substantially as set forth in FIG. 5;
b. a C2/c single crystal x-ray diffraction space group;
c. a single crystal x-ray diffraction unit cell having the parameters: a=58.1415(14) Å, b=4.03974(8) Å, c=17.1204(3) Å, α=90°, β=90.261(2)°, γ=90°, V=4021.15(14) $Å^3$;
d. a differential scanning calorimetry (DSC) curve substantially as set forth in FIG. 3B; and
e. a differential scanning calorimetry (DSC) curve having an exotherm with an onset at about 207° C.

In one or more embodiments, crystalline Form A of Compound 1 is characterized by a differential scanning calorimetry (DSC) having an exotherm between 200° C. and 215° C. For example, Form A of Compound 1, can be characterized by a differential scanning calorimetry (DSC) having an exotherm at 200° C., 201° C., 202° C., 203° C., 204° C., 205° C., 206° C., 207° C., 208° C., 209° C., 210° C., 211° C., 212° C., 213° C., 214° C. or 215° C. For example, Form A of Compound 1, can be characterized by a differential scanning calorimetry (DSC) having an exotherm at about 200° C., about 201° C., about 202° C., about 203° C., about 204° C., about 205° C., about 206° C., about 207° C., about 208° C., about 209° C., about 210° C., about 211° C., about 212° C., about 213° C., about 214° C. or about 215° C. In some embodiments, crystalline Form A of Compound 1 is characterized by a differential scanning calorimetry (DSC) having an exotherm at 207° C. In some embodiments, crystalline Form A of Compound 1 is characterized by a differential scanning calorimetry (DSC) having an exotherm at about 207° C.

In some embodiments, the crystalline form of compound 1 is Form B and exhibits an XRPD pattern comprising at least one peak selected from 13.0 and 15.3 degrees 2θ±0.2 degrees 2θ.

In some embodiments, the crystalline form of compound 1 is Form B and exhibits an XRPD pattern further comprising at least one additional peak selected from the group consisting of 7.0, 9.3, 10.2, 10.4, 12.5, 13.6, 14.0, 22.0, 23.0, 23.6, and 27.3 degrees 2θ±0.2 degrees 2θ.

Figure 7:
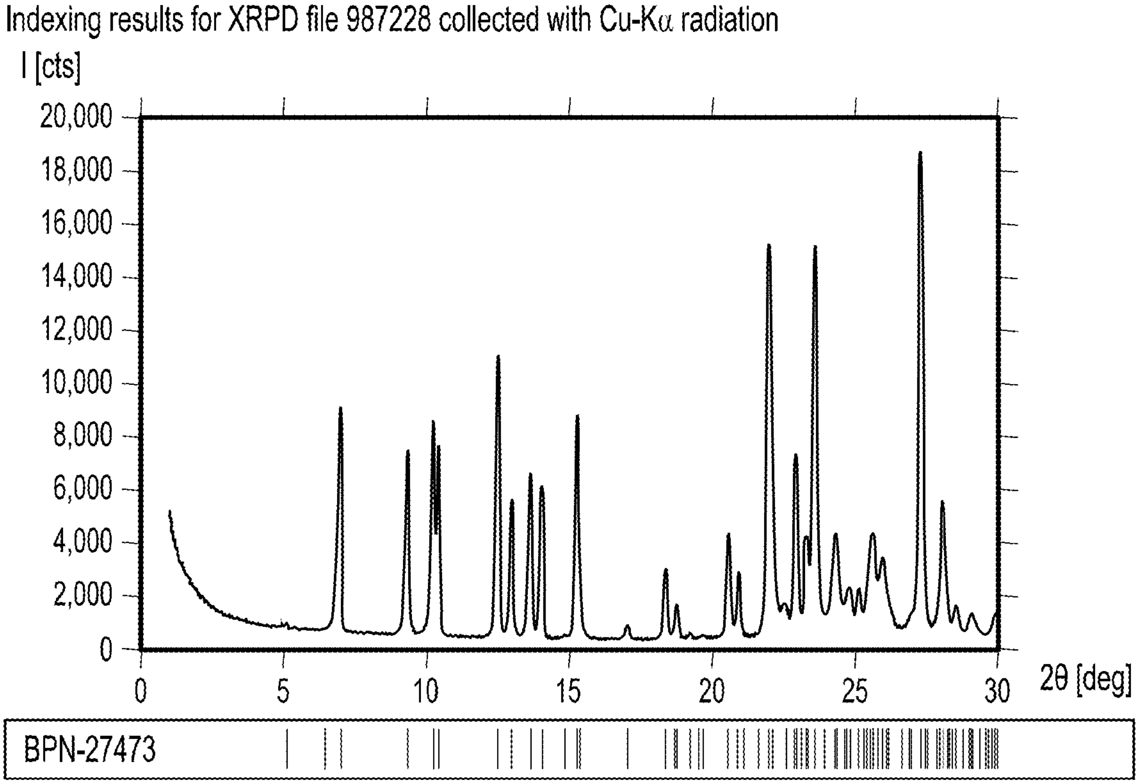
FIG. 7 depicts the indexed XRPD pattern of desolvated Form B.

In some embodiments, this disclosure provides a crystalline form of Compound 1, wherein the crystalline form is desolvated. In some embodiments, the crystalline form of Compound 1 is Form B. In some embodiments, crystalline Form B is characterized by one or more of:

a. an x-ray powder diffraction (XRPD) pattern substantially as set forth in FIG. 7;
b. a monoclinic single crystal x-ray diffraction unit cell;
c. a single crystal x-ray diffraction formula unit volume of about 497 $Å^3$; and
d. a differential scanning calorimetry (DSC) curve having an exotherm with an onset at about 190° C.

In some embodiments, crystalline Form B is characterized by two or more of:

a. an x-ray powder diffraction (XRPD) pattern substantially as set forth in FIG. 7;
b. a monoclinic single crystal x-ray diffraction unit cell;
c. a single crystal x-ray diffraction formula unit volume of about 497 $Å^3$; and
d. a differential scanning calorimetry (DSC) curve having an exotherm with an onset at about 190° C.

In some embodiments, crystalline Form B is characterized by three or more of:

a. an x-ray powder diffraction (XRPD) pattern substantially as set forth in FIG. 7;
b. a monoclinic single crystal x-ray diffraction unit cell;
c. a single crystal x-ray diffraction formula unit volume of about 497 $Å^3$; and
d. a differential scanning calorimetry (DSC) curve having an exotherm with an onset at about 190° C.

In some embodiments, crystalline Form B is characterized by:

a. an x-ray powder diffraction (XRPD) pattern substantially as set forth in FIG. 7;
b. a monoclinic single crystal x-ray diffraction unit cell;
c. a single crystal x-ray diffraction formula unit volume of about 497 $Å^3$; and
d. a differential scanning calorimetry (DSC) curve having an exotherm with an onset at about 190° C.

In one or more embodiments, crystalline Form B of Compound 1 is characterized by a single crystal x-ray diffraction formula unit volume between 495 $Å^3$ and 500 $Å^3$. For example, Form B of Compound 1, can be characterized by single crystal x-ray diffraction formula unit volume of 495 $Å^3$, 496 $Å^3$, 497 $Å^3$, 498 $Å^3$, 499 $Å^3$, or 500 $Å^3$. In some embodiments, crystalline Form B of Compound 1 is characterized by a single crystal x-ray diffraction formula unit volume 497° C.

In one or more embodiments, crystalline Form B of Compound 1 is characterized by a differential scanning calorimetry (DSC) having an exotherm between 185° C. and 195° C. For example, Form B of Compound 1, can be characterized by a differential scanning calorimetry (DSC) having an exotherm at 185° C., 186° C., 187° C., 188° C., 189° C., 190° C., 191° C., 192° C., 193° C., 194° C., 195° C. For example, Form B of Compound 1, can be characterized by a differential scanning calorimetry (DSC) having an exotherm at about 185° C., about 186° C., about 187° C., about 188° C., about 189° C., about 190° C., about 191° C., about 192° C., about 193° C., about 194° C., about 195° C. In some embodiments, crystalline Form B of Compound 1 is characterized by a differential scanning calorimetry (DSC) having an exotherm at 190° C. In some embodiments, crystalline Form B of Compound 1 is characterized by a differential scanning calorimetry (DSC) having an exotherm at about 190° C.

In some embodiments, the crystalline form of compound 1 is Form C and exhibits an XRPD pattern comprising at least one peak selected from 8.5 and 18.9 degrees 2θ±0.2 degrees 2θ.

In some embodiments, the crystalline form of compound 1 is Form C and exhibits an XRPD pattern further comprising at least one additional peak selected from the group consisting of 7.1, 9.4, 10.3, 12.3, 12.5, 14.2, 20.7, 22.1, 23.2, 23.7, 24.0, and 26.4 degrees 2θ±0.2 degrees 2θ.

Figure 17:
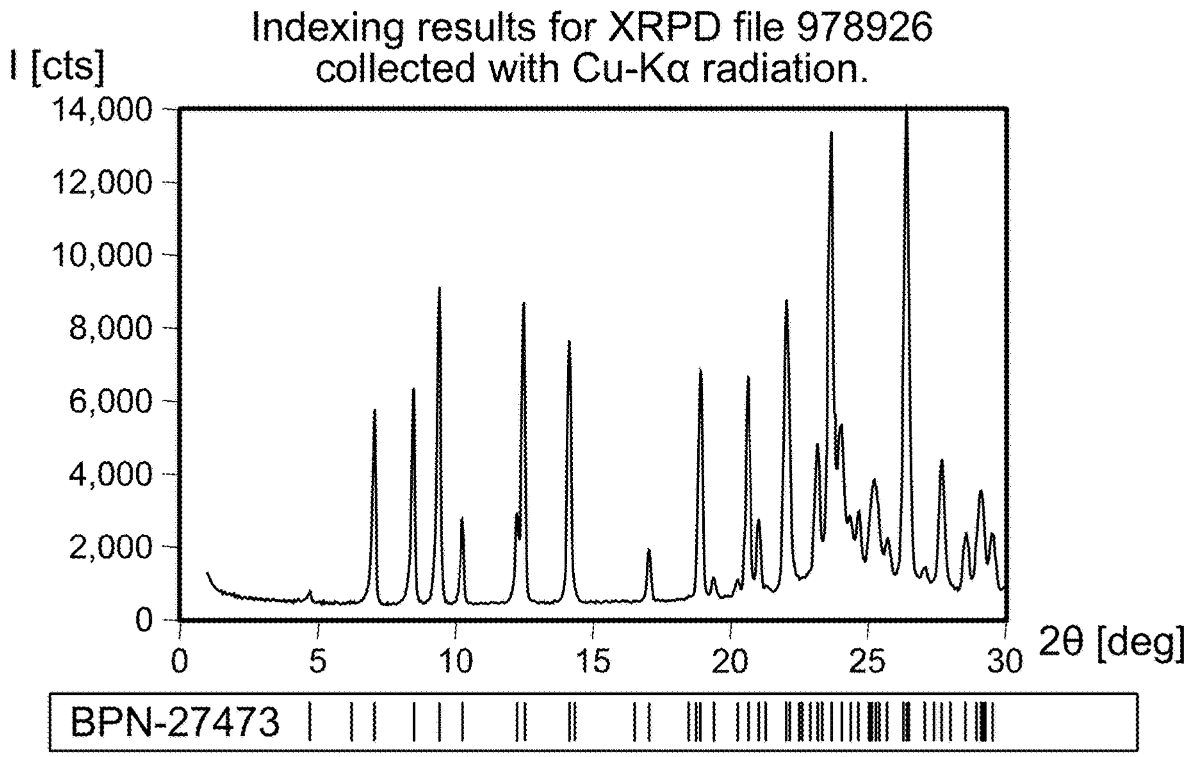
FIG. 17 is the indexed XRPD pattern of methanolate Form C.
Figure 18A:
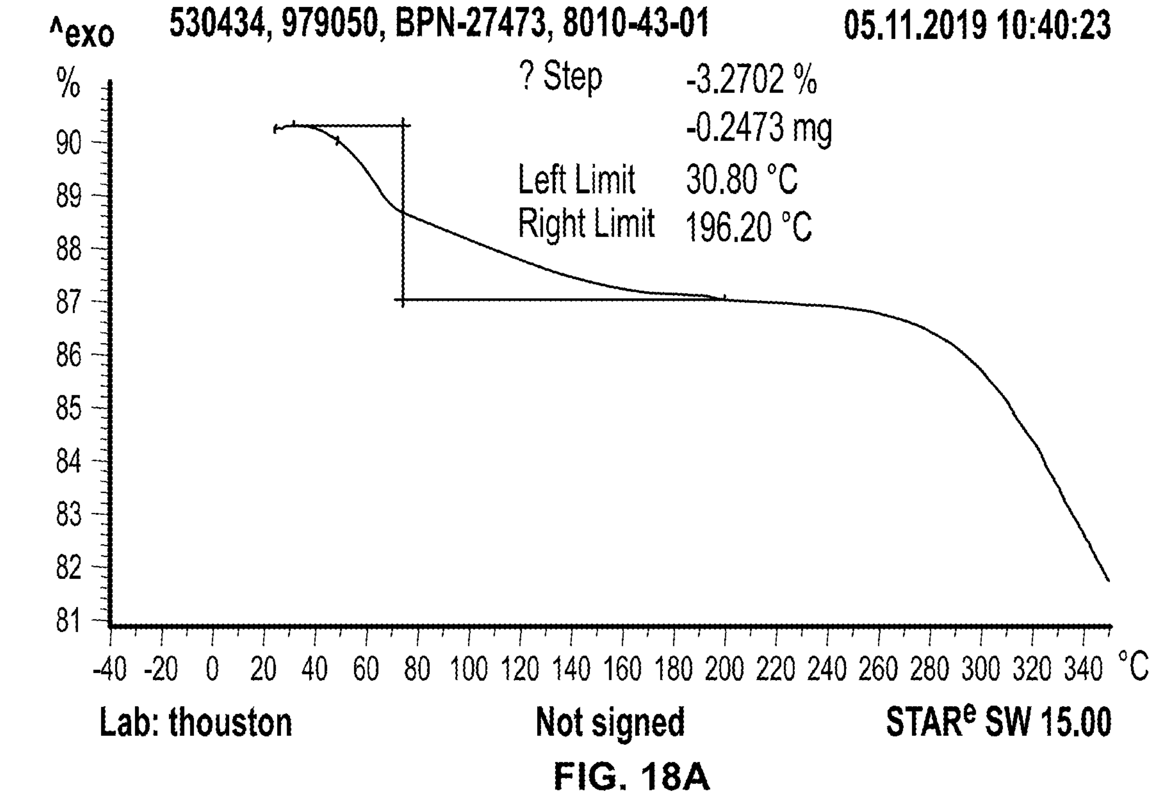
FIGS. 18A and 18B depict the thermograms of methanolate Form C.
Figure 18B:
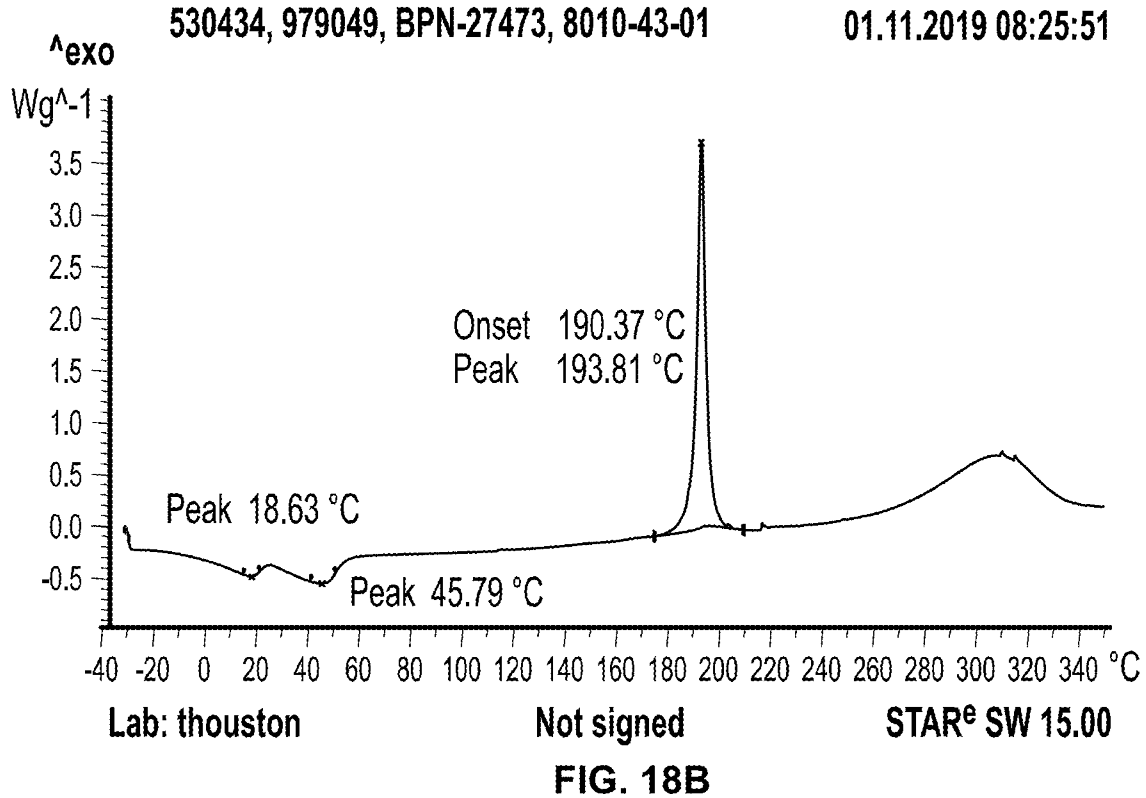

In some embodiments, this disclosure provides a crystalline form of Compound 1, wherein the crystalline form is solvated. In some embodiments, the solvated crystalline form of Compound 1 is a methanolate. In some embodiments, the solvated crystalline form of Compound 1 is Form C. In some embodiments, crystalline Form C is characterized by one or more of:

a. an x-ray powder diffraction (XRPD) pattern substantially as set forth in FIG. 17;
b. a monoclinic single crystal x-ray diffraction unit cell;
c. a single crystal x-ray diffraction formula unit volume of about 544 $Å^3$.
d. a differential scanning calorimetry (DSC) curve substantially as set forth in FIG. 18B; and
e. a differential scanning calorimetry (DSC) curve having an exotherm with an onset at about 190° C.

In some embodiments, crystalline Form C is characterized by two or more of:

a. an x-ray powder diffraction (XRPD) pattern substantially as set forth in FIG. 17;
b. a monoclinic single crystal x-ray diffraction unit cell;
c. a single crystal x-ray diffraction formula unit volume of about 544 $Å^3$.
d. a differential scanning calorimetry (DSC) curve substantially as set forth in FIG. 18B; and
e. a differential scanning calorimetry (DSC) curve having an exotherm with an onset at about 190° C.

In some embodiments, crystalline Form C is characterized by three or more of:

a. an x-ray powder diffraction (XRPD) pattern substantially as set forth in FIG. 17;
b. a monoclinic single crystal x-ray diffraction unit cell;
c. a single crystal x-ray diffraction formula unit volume of about 544 $Å^3$.
d. a differential scanning calorimetry (DSC) curve substantially as set forth in FIG. 18B; and
e. a differential scanning calorimetry (DSC) curve having an exotherm with an onset at about 190° C.

In some embodiments, crystalline Form C is characterized by four or more of:

a. an x-ray powder diffraction (XRPD) pattern substantially as set forth in FIG. 17;

b. a monoclinic single crystal x-ray diffraction unit cell;

c. a single crystal x-ray diffraction formula unit volume of about 544 $Å^3$.

d. a differential scanning calorimetry (DSC) curve substantially as set forth in FIG. 18B; and e. a differential scanning calorimetry (DSC) curve having an exotherm with an onset at about 190° C.

In some embodiments, crystalline Form C is characterized by:

a. an x-ray powder diffraction (XRPD) pattern substantially as set forth in FIG. 17;

b. a monoclinic single crystal x-ray diffraction unit cell;

c. a single crystal x-ray diffraction formula unit volume of about 544 $Å^3$.

d. a differential scanning calorimetry (DSC) curve substantially as set forth in FIG. 18B; and e. a differential scanning calorimetry (DSC) curve having an exotherm with an onset at about 190° C.

In one or more embodiments, crystalline Form C of Compound 1 is characterized by a single crystal x-ray diffraction formula unit volume between 495 $Å^3$ and 505 $Å^3$. For example, Form C of Compound 1, can be characterized by single crystal x-ray diffraction formula unit volume of 495 $Å^3$, 496 $Å^3$, 497 $Å^3$, 498 $Å^3$, 499 $Å^3$, 500 $Å^3$, 501 $Å^3$, 502 $Å^3$, 503 $Å^3$, 504 $Å^3$, or 505 $Å^3$. In some embodiments, crystalline Form C of Compound 1 is characterized by a single crystal x-ray diffraction formula unit volume at 497 $Å^3$.

In one or more embodiments, crystalline Form C of Compound 1 is characterized by a differential scanning calorimetry (DSC) having an exotherm between 185° C. and 195° C. For example, Form C of Compound 1, can be characterized by a differential scanning calorimetry (DSC) having an exotherm at 185° C., 186° C., 187° C., 188° C., 189° C., 190° C., 191° C., 192° C., 193° C., 194° C., or 195° C. For example, Form C of Compound 1, can be characterized by a differential scanning calorimetry (DSC) having an exotherm at about 185° C., about 186° C., about 187° C., about 188° C., about 189° C., about 190° C., about 191° C., about 192° C., about 193° C., about 194° C., or about 195° C. In some embodiments, crystalline Form C of Compound 1 is characterized by a differential scanning calorimetry (DSC) having an exotherm at 190° C. In some embodiments, crystalline Form C of Compound 1 is characterized by a differential scanning calorimetry (DSC) having an exotherm at about 190° C.

In some embodiments, the crystalline form of compound 1 is Form E and exhibits an XRPD pattern comprising at least one peak selected from the group consisting of 11.4, 18.1, and 21.6 degrees 2θ±0.2 degrees 2θ.

In some embodiments the crystalline form of compound 1 is Form E and exhibits an XRPD pattern further comprising at least one additional peak selected from the group consisting of 7.2, 22.0, 23.0, 24.2, 25.0, and 26.6 degrees 2θ±0.2 degrees 2θ.

Figure 11:
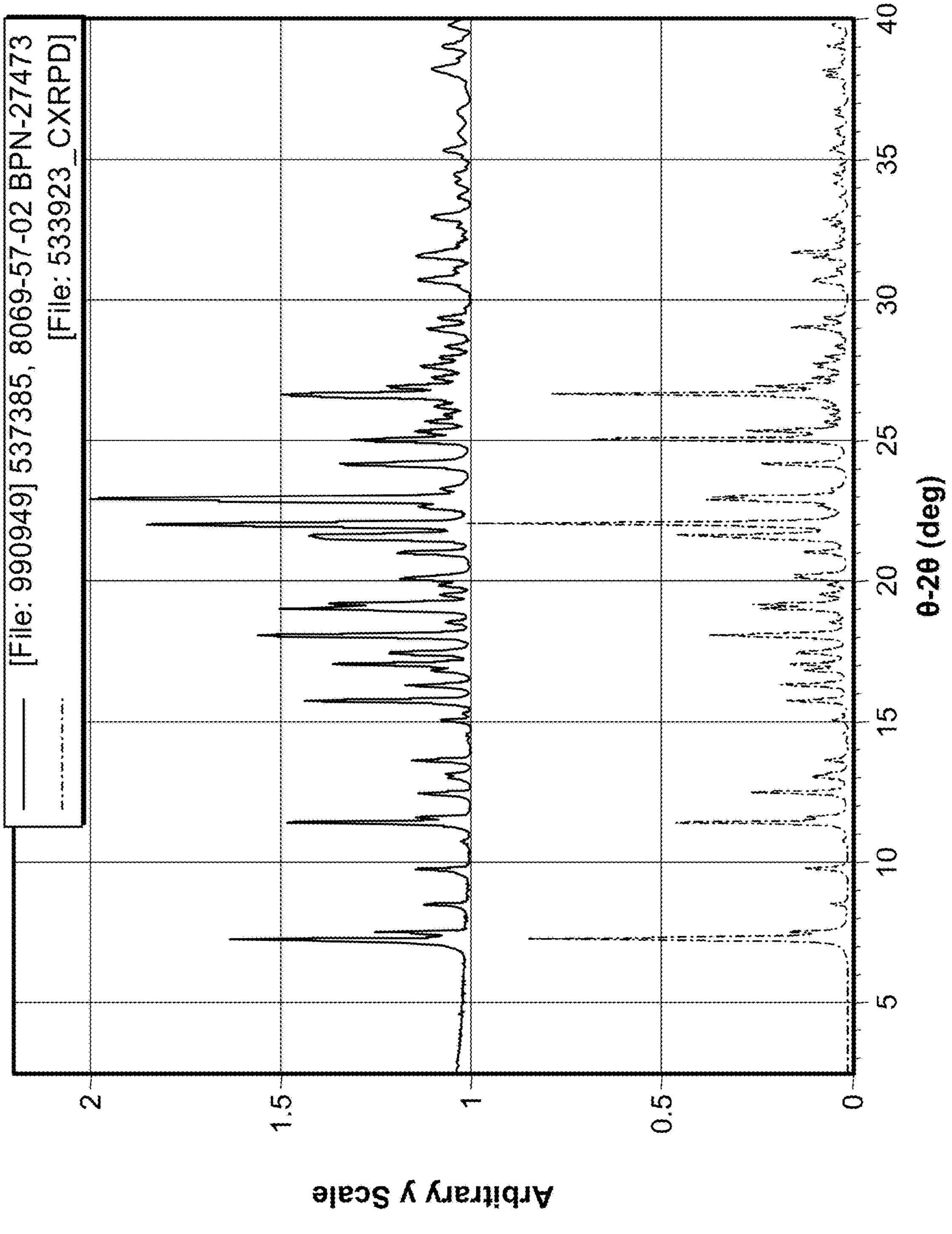
FIG. 11 is an XRPD overlay of the experimental (top) and calculated (bottom) anhydrous Form E.
Figure 12A:
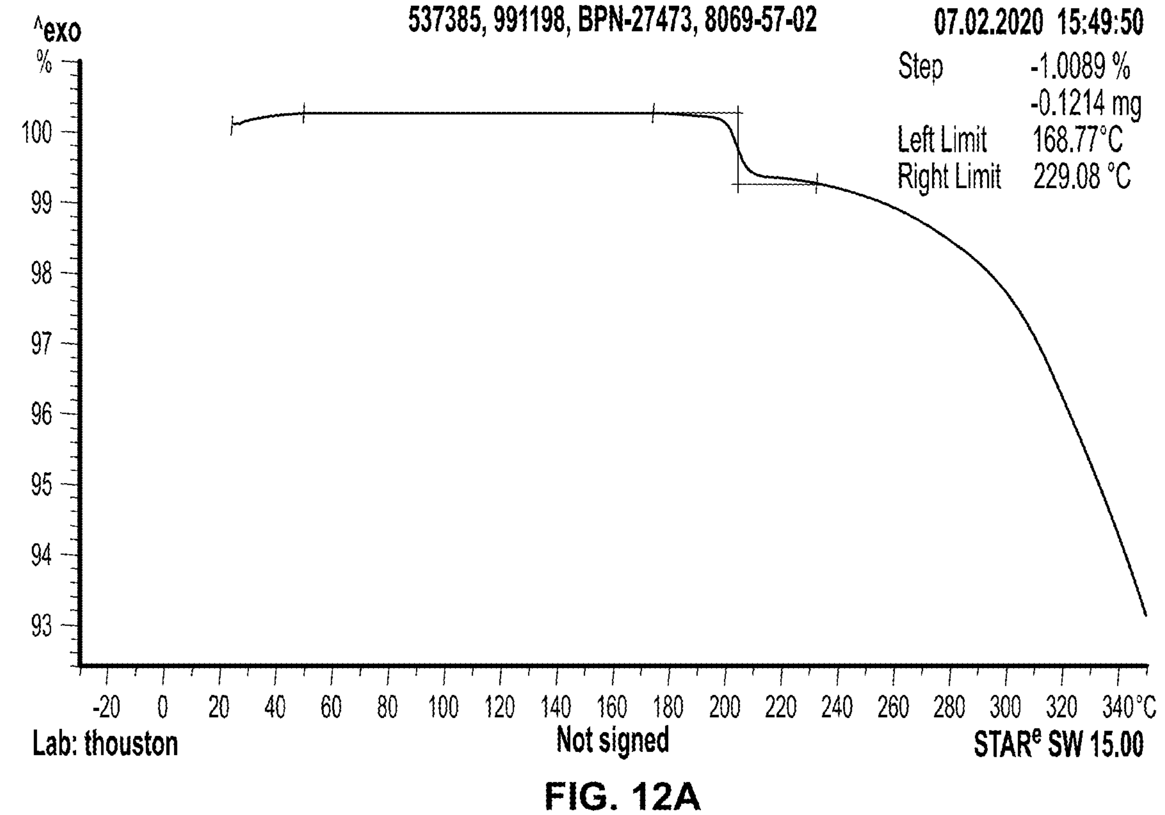
FIGS. 12A and 12B depict the thermograms of anhydrous Form E.
Figure 12B:
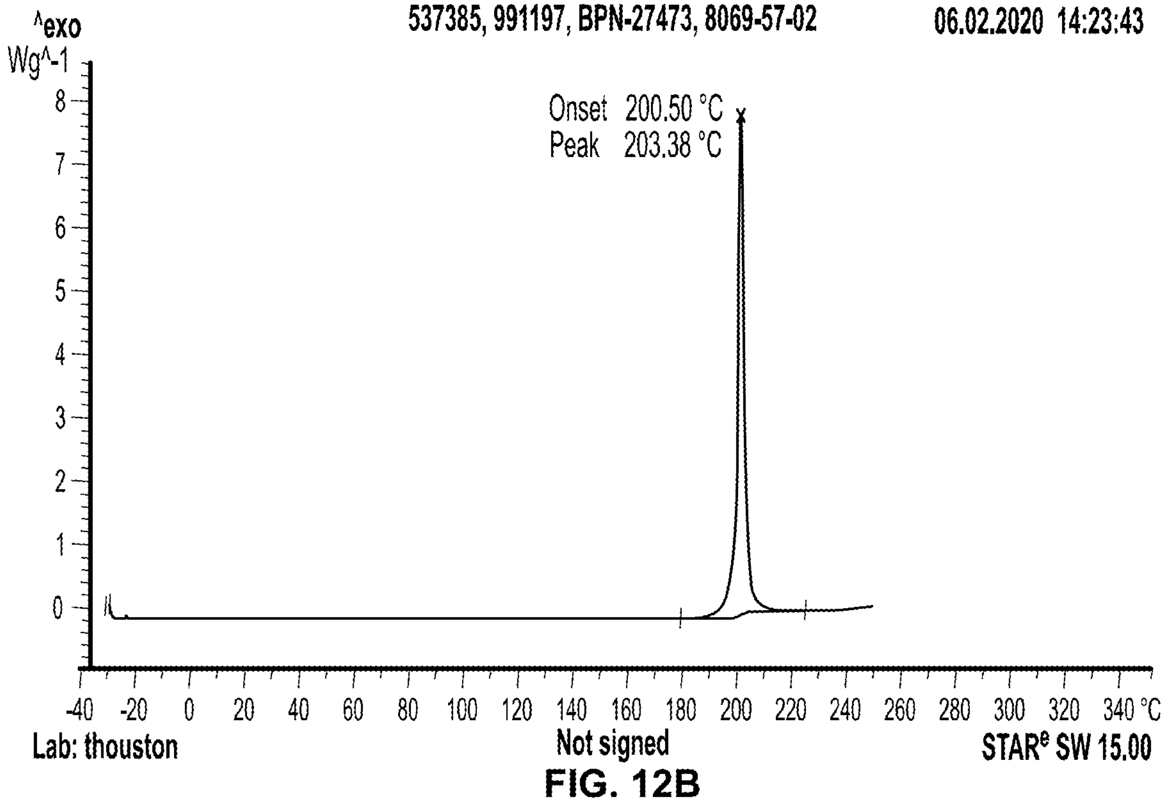

In some embodiments, this disclosure provides a crystalline form of Compound 1, wherein the crystalline form is anhydrous. In some embodiments, the solvated crystalline form of Compound 1 is Form E. In some embodiments, crystalline Form E is characterized by one or more of:

a. an x-ray powder diffraction (XRPD) pattern substantially as set forth in FIG. 11;

b. a $P2_1/n$ single crystal x-ray diffraction space group;

c. single crystal x-ray diffraction unit cell having the parameters: a=11.83974(13) Å, b=23.5195(2) Å, c=14.48807(17) Å, α=90°, β=101.5333(11)°, γ=90°, V=3952.96(7) $Å^3$;

d. a differential scanning calorimetry (DSC) curve substantially as set forth in FIG. 12B; and e. a differential scanning calorimetry (DSC) curve having an exotherm with an onset at about 201° C.

In some embodiments, the solvated crystalline form of Compound 1 is Form E. In some embodiments, crystalline Form E is characterized by two or more of:

a. an x-ray powder diffraction (XRPD) pattern substantially as set forth in FIG. 11;

b. a $P2_1/n$ single crystal x-ray diffraction space group;

c. single crystal x-ray diffraction unit cell having the parameters: a=11.83974(13) Å, b=23.5195(2) Å, c=14.48807(17) Å, α=90°, β=101.5333(11)°, γ=90°, V=3952.96(7) $Å^3$;

d. a differential scanning calorimetry (DSC) curve substantially as set forth in FIG. 12B; and e. a differential scanning calorimetry (DSC) curve having an exotherm with an onset at about 201° C.

In some embodiments, the solvated crystalline form of Compound 1 is Form E. In some embodiments, crystalline Form E is characterized by three or more of:

a. an x-ray powder diffraction (XRPD) pattern substantially as set forth in FIG. 11;

b. a $P2_1/n$ single crystal x-ray diffraction space group;

c. single crystal x-ray diffraction unit cell having the parameters: a=11.83974(13) Å, b=23.5195(2) Å, c=14.48807(17) Å, α=90°, β=101.5333(11)°, γ=90°, V=3952.96(7) $Å^3$;

d. a differential scanning calorimetry (DSC) curve substantially as set forth in FIG. 12B; and e. a differential scanning calorimetry (DSC) curve having an exotherm with an onset at about 201° C.

In some embodiments, the solvated crystalline form of Compound 1 is Form E. In some embodiments, crystalline Form E is characterized by four or more of:

a. an x-ray powder diffraction (XRPD) pattern substantially as set forth in FIG. 11;

b. a $P2_1/n$ single crystal x-ray diffraction space group;

c. single crystal x-ray diffraction unit cell having the parameters: a=11.83974(13) Å, b=23.5195(2) Å, c=14.48807(17) Å, α=90°, β=101.5333(11)°, γ=90°, V=3952.96(7) $Å^3$;

d. a differential scanning calorimetry (DSC) curve substantially as set forth in FIG. 12B; and e. a differential scanning calorimetry (DSC) curve having an exotherm with an onset at about 201° C.

In some embodiments, the solvated crystalline form of Compound 1 is Form E. In some embodiments, crystalline Form E is characterized by:

a. an x-ray powder diffraction (XRPD) pattern substantially as set forth in FIG. 11;

b. a $P2_1/n$ single crystal x-ray diffraction space group;

c. single crystal x-ray diffraction unit cell having the parameters: a=11.83974(13) Å, b=23.5195(2) Å, c=14.48807(17) Å, α=90°, β=101.5333(11)°, γ=90°, V=3952.96(7) $Å^3$;

d. a differential scanning calorimetry (DSC) curve substantially as set forth in FIG. 12B; and e. a differential scanning calorimetry (DSC) curve having an exotherm with an onset at about 201° C.

In one or more embodiments, crystalline Form E of Compound 1 is characterized by a differential scanning calorimetry (DSC) having an exotherm between 195° C. and 205° C. For example, Form E of Compound 1, can be characterized by a differential scanning calorimetry (DSC) having an exotherm at 195° C., 196° C., 197° C., 198° C., 199° C., 200° C., 201° C., 202° C., 203° C., 204° C., or 205°

C. For example, Form E of Compound 1, can be characterized by a differential scanning calorimetry (DSC) having an exotherm at about 195° C., about 196° C., about 197° C., about 198° C., about 199° C., about 200° C., about 201° C., about 202° C., about 203° C., about 204° C., or about 205° C. In some embodiments, crystalline Form E of Compound 1 is characterized by a differential scanning calorimetry (DSC) having an exotherm at 190° C. In some embodiments, crystalline Form E of Compound 1 is characterized by a differential scanning calorimetry (DSC) having an exotherm at about 190° C.

In some embodiments, the crystalline form of compound 1 is Form F and exhibits an XRPD pattern comprising at least one peak selected from a group consisting of 9.9, 11.9, 17.3, 19.4, and 25.7 degrees 2θ±0.2 degrees 2θ.

In some embodiments, the crystalline form of compound 1 is Form F and exhibits an XRPD pattern further comprising at least one additional peak selected from the group consisting of 9.7, 12.1, 20.8, 23.2, 23.7, 24.2, 25.0, and 26.4 degrees 2θ±0.2 degrees 2θ.

Figure 13:
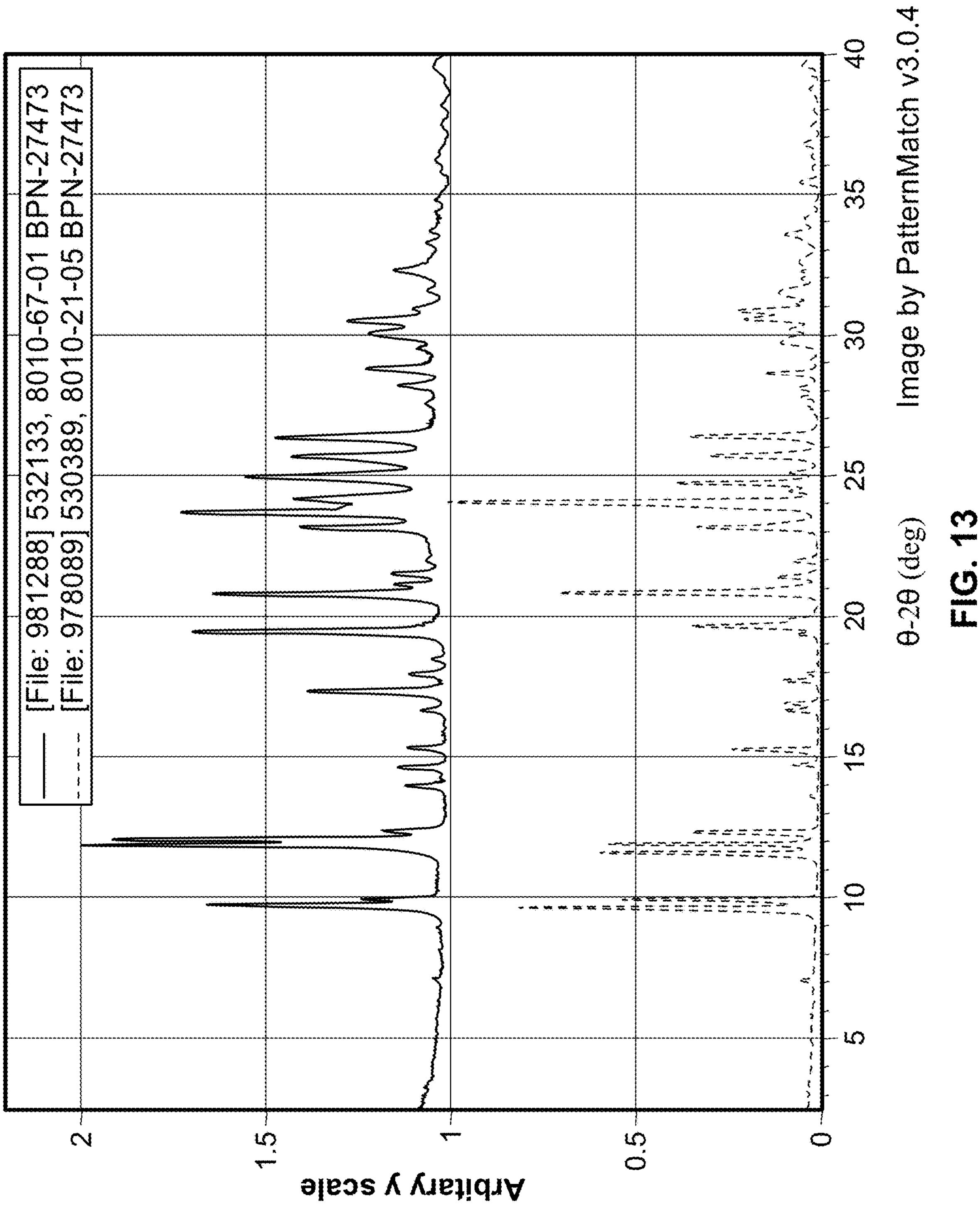
FIG. 13 is an XRPD overlay of monohydrate Form F (top) and the HCl salt of Compound 1 (bottom) for reference.

In some embodiments, this disclosure provides a crystalline form of Compound 1, wherein the crystalline form is solvated. In some embodiments, the solvated crystalline form of Compound 1 is a hydrate. In some embodiments, the solvated crystalline form of Compound 1 is Form F. In some embodiments, crystalline Form F is characterized by one or more of:

a. an x-ray powder diffraction (XRPD) pattern substantially as set forth in FIG. 13;
b. a triclinic single crystal x-ray diffraction unit cell; and
c. a single crystal x-ray diffraction formula unit volume of about 511 $Å^3$; and
d. a differential scanning calorimetry (DSC) curve having an exotherm at about 120° C.

In some embodiments, crystalline Form F is characterized by two or more of:

a. an x-ray powder diffraction (XRPD) pattern substantially as set forth in FIG. 13;
b. a triclinic single crystal x-ray diffraction unit cell; and
c. a single crystal x-ray diffraction formula unit volume of about 511 $Å^3$; and
d. a differential scanning calorimetry (DSC) curve having an exotherm at about 120° C.

In some embodiments, crystalline Form F is characterized by three or more of:

a. an x-ray powder diffraction (XRPD) pattern substantially as set forth in FIG. 13;
b. a triclinic single crystal x-ray diffraction unit cell; and
c. a single crystal x-ray diffraction formula unit volume of about 511 $Å^3$; and
d. a differential scanning calorimetry (DSC) curve having an exotherm at about 120° C.

In some embodiments, crystalline Form F is characterized by:

a. an x-ray powder diffraction (XRPD) pattern substantially as set forth in FIG. 13;
b. a triclinic single crystal x-ray diffraction unit cell; and
c. a single crystal x-ray diffraction formula unit volume of about 511 $Å^3$; and
d. a differential scanning calorimetry (DSC) curve having an exotherm at about 120° C.

In one or more embodiments, crystalline Form F of Compound 1 is characterized by a single crystal x-ray diffraction formula unit volume between 506 $Å^3$ and 516 $Å^3$. For example, Form F of Compound 1, can be characterized by single crystal x-ray diffraction formula unit volume of 506 $Å^3$, 507 $Å^3$, 508 $Å^3$, 509 $Å^3$, 510 $Å^3$, 511 $Å^3$, 512 $Å^3$, 513 $Å^3$, 514 $Å^3$, 515 $Å^3$, 516 $Å^3$. In some embodiments, crystalline Form F of Compound 1 is characterized by a single crystal x-ray diffraction formula unit volume at 511 $Å^3$.

In one or more embodiments, crystalline Form F of Compound 1 is characterized by a differential scanning calorimetry (DSC) having an exotherm between 115° C. and 130° C. For example, Form F of Compound 1, can be characterized by a differential scanning calorimetry (DSC) having an exotherm at 115° C., 116° C., 117° C., 118° C., 119° C., 120° C., 121° C., 122° C., 123° C., 124° C., 125° C., 126° C., 127° C., 128° C., 129° C. or 130° C. For example, Form F of Compound 1, can be characterized by a differential scanning calorimetry (DSC) having an exotherm at about 115° C., about 116° C., about 117° C., about 118° C., about 119° C., about 120° C., about 121° C., about 122° C., about 123° C., about 124° C., about 125° C., about 126° C., about 127° C., about 128° C., about 129° C. or about 130° C. In some embodiments, crystalline Form F of Compound 1 is characterized by a differential scanning calorimetry (DSC) having an exotherm at 120° C. In some embodiments, crystalline Form F of Compound 1 is characterized by a differential scanning calorimetry (DSC) having an exotherm at about 120° C. In some embodiments, crystalline Form F of Compound 1 is characterized by a differential scanning calorimetry (DSC) having an exotherm above about 120° C.

In one or more embodiments, the disclosure is directed to a crystalline form of Compound 1, characterized by a higher thermodynamic stability as compared to other crystalline forms of Compound 1. The thermodynamic stability of crystalline forms A, B, C, E and F was investigated, wherein it was determined that polymorphic Form A of Compound 1 has superior thermodynamic stability as compared to Form B, Material D, Form C, Form E and Form F. It also has limited hygroscopicity, preserving crystallinity and potency and easing handling. Accordingly, in some embodiments, this disclosure is directed to a crystalline form of Compound 1, wherein the crystalline form corresponds to Form A.

Pharmaceutical Compositions and Combinations

In one aspect, this disclosure provides pharmaceutical compositions and combinations comprising a crystalline form of Compound 1 (e.g., Form A, Form B, Form C, Form E or Form F), and, optionally, one or more additional therapeutic agents. Ins some embodiments, this disclosure provides pharmaceutical compositions and combinations comprising a crystalline form of Compound 1, wherein the crystalline form is Form A, and, optionally, one or more additional therapeutic agents. In some embodiments, the one or more additional therapeutic agents are selected from the group consisting of an antipsychotic, memantine, an SV2A inhibitor, and an AChEI, or a pharmaceutically acceptable salt, hydrate, solvate, polymorph or prodrug of any of the foregoing. In some embodiments, at least one of the one or more additional therapeutic agents is an SV2A inhibitor selected from the group consisting of levetiracetam, seletracetam, and brivaracetam, or a pharmaceutically acceptable salt, hydrate, solvate, polymorph or prodrug of any of the foregoing. In some embodiments, at least one of the one or more additional therapeutic agents is an antipsychotic selected from the group consisting of aripiprazole, olanzapine, and ziprasidone, or a pharmaceutically acceptable salt, hydrate, solvate, polymorph or prodrug of any of the foregoing. In some embodiments, at least one of the one or more additional therapeutic agents is memantine, or a pharmaceutically acceptable salt, hydrate, solvate, polymorph or prodrug thereof. In some embodiments, at least one of the one or more additional therapeutic agents is an AChEI selected from the group consisting of donepezil, galantamine, ambenonium and rivastigmine, or a pharmaceutically acceptable salt, hydrate, solvate, polymorph or prodrug of any of the forgoing. In some embodiments, the pharmaceutical compositions and combinations described herein comprise a crystalline form of Compound 1, and one or more additional therapeutic agents. In some embodiments, the pharmaceutical compositions and combinations described herein comprise more than crystalline form of Compound 1.

In some embodiments, the disclosure provides a pharmaceutical combination comprising a first pharmaceutical composition comprising a crystalline form of Compound 1 (e.g., Form A, Form B, Form C, Form E or Form F) as described herein; and one or more additional pharmaceutical compositions comprising a therapeutic agent selected from the groups consisting of an antipsychotic, memantine, an SV2A inhibitor, and an AChEI, or a pharmaceutically acceptable salt, hydrate, solvate, polymorph or prodrug of any of the foregoing. In some embodiments, the disclosure provides a pharmaceutical combination comprising a first pharmaceutical composition comprising a crystalline form of Compound 1, wherein the crystalline form is Form A, as described herein; and one or more additional pharmaceutical compositions comprising one or more therapeutic agents selected from the groups consisting of an antipsychotic, memantine, an SV2A inhibitor, and an AChEI, or a pharmaceutically acceptable salt, hydrate, solvate, polymorph or prodrug of any of the foregoing. In some embodiments, the first pharmaceutical composition comprises more than one crystalline form of Compound 1. In some embodiments, at least one of the one or more additional pharmaceutical compositions comprises an SV2A inhibitor selected from the group consisting of levetiracetam, seletracetam, and brivaracetam, or a pharmaceutically acceptable salt, hydrate, solvate, polymorph or prodrug of any of the foregoing. In some embodiments, at least one of the one or more additional pharmaceutical compositions comprises an antipsychotic selected from the group consisting of aripiprazole, olanzapine, and ziprasidone, or a pharmaceutically acceptable salt, hydrate, solvate, polymorph or prodrug of any of the foregoing. In some embodiments, at least one of the one or more additional pharmaceutical compositions comprises memantine, or a pharmaceutically acceptable salt, hydrate, solvate, polymorph or prodrug thereof. In some embodiments, at least one of the one or more additional pharmaceutical compositions comprises an AChEI selected from the group consisting of donepezil, galantamine, ambenonium, and rivastigmine, or a pharmaceutically acceptable salt, hydrate, solvate, polymorph or prodrug of any of the forgoing.

In some embodiments, the first and one or more additional pharmaceutical compositions are formulated separately. In certain such embodiments, the first and one or more additional pharmaceutical compositions are packaged together. In some embodiments, the first and one or more additional pharmaceutical compositions are packaged separately. In some embodiments, the first and one or more additional pharmaceutical compositions are formulated together.

In certain embodiments, the pharmaceutical compositions and combinations according to this disclosure, or one or more of their components are formulated in a solid form. In certain embodiments, the pharmaceutical compositions and combinations according to this disclosure, or one or more of their components are formulated in a liquid form. In certain embodiments, the pharmaceutical compositions and combinations according to this disclosure, or one or more of their components are formulated in a suspension form. In certain embodiments, the pharmaceutical compositions and combinations according to this disclosure, or one or more of their components are formulated is a unit dosage form. In certain embodiments, the pharmaceutical compositions and combinations according to this disclosure, or one or more of their components are formulated in a capsule or tablet form. In certain embodiments, the pharmaceutical compositions and combinations according to this disclosure, or one or more of their components are formulated is for oral administration. In certain embodiments, the pharmaceutical compositions and combinations according to this disclosure, or one or more of their components are formulated is for intraperenteral administration.

In some embodiments, the pharmaceutical compositions and combinations described herein, or one or more of their components are formulated with a pharmaceutically acceptable carrier. Pharmaceutically acceptable carries include, but are not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Examples of suitable aqueous and non-aqueous carriers which may be employed in the pharmaceutical compositions or combinations (or components thereof) of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In some embodiments, no carrier is used. The pharmaceutical compositions and combinations described herein may be formulated in any convenient way for use in human medicine.

The pharmaceutical compositions and combinations described herein, or one or more of their components may be formulated for administration by any suitable route as described herein and known in the art. For example, the pharmaceutical compositions and combinations described herein (or one or more of their components) for parental administration (e.g., subcutaneously, intravenously, arterially, intradermally, intramuscularly, intraperitoneally) or intraspinal or intracerebral administration include sterile aqueous and nonaqueous injectable solutions, dispersions, suspensions or emulsions as well as sterile powders to be reconstituted in sterile injectable solutions or dispersions prior to use, which may contain antioxidants, buffers, bacteriostats, solutes which render the pharmaceutical composition or combination (or a component thereof) isotonic with the blood of the intended recipient, or suspending or thickening agents. When administered parenterally, the crystalline form of Compound 1 as described herein, and/or the one or more additional therapeutic agent may be in a pyrogen-free, physiologically acceptable form. Techniques and formulations generally may be found in Remington's Pharmaceutical Sciences, Meade Publishing Co., Easton, Pa.

Pharmaceutical compositions or combinations according to the disclosure for intraoral and oral delivery (including sublingual and buccal administration, e.g. Danckwerts et al, and oral) include but are not limited to bioadhesive polymers, tablets, patches, thin films, liquids and semisolids (see e.g., Smart et al).

In some embodiments, pharmaceutical compositions or combinations (or one or more of their components) according to the disclosure may be in a solid dosage form such as a capsule, tablet, dragee, pill, lozenge, cachet, powder, troche, wafer, or granule. In solid dosage forms for oral administration, the crystalline form of Compound 1 as described herein, and/or the one or more additional therapeutic agent may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions or combinations (or components thereof) of the disclosure may also comprise buffering agents. Solid pharmaceutical compositions or combinations (or components thereof) of a similar type may also be employed as fillers in soft and hard-filled gelatin capsules using such excipients as lactose or milk sugars, as well as high molecular weight polyethylene glycols and the like.

In some embodiments, pharmaceutical compositions or combinations (or one or more of their components) according to the disclosure may also be in an aqueous or non-aqueous liquid dosage form including solution, emulsion, microemulsion, suspension, syrup, pastille, or elixir. In some embodiments, the pharmaceutical composition or combination of the disclosure is in an aqueous solution. In some embodiments, the pharmaceutical composition or combination of the disclosure is in a suspension form. Where appropriate, the pharmaceutical composition or combination of the disclosure may be prepared with coatings such as enteric coatings or they may be formulated so as to provide extended release (e.g., a controlled release, a prolonged release, a sustained release, a delayed release, or a slow release) of the crystalline form of Compound 1, and/or the one or more additional therapeutic agent according to methods well known in the art. Liquid dosage forms may also comprise inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, oral pharmaceutical compositions or combinations can also include adjuvants such as wetting agents, emulsifying and suspending agents, sweetening, flavoring, coloring, perfuming, and preservative agents. In some embodiments, the pharmaceutical composition or combination according to the disclosure (or one or more of their components) may comprise suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Pharmaceutical compositions or combinations of the disclosure, or one or more of their components, for respiratory delivery (pulmonary and nasal delivery) include but are not limited to a variety of pressurized metered dose inhalers, dry powder inhalers, nebulizers, aqueous mist inhalers, drops, solutions, suspensions, sprays, powders, gels, ointments, and specialized systems such as liposomes and microspheres (see e.g. Owens et al, "Alternative Routes of Insulin Delivery" and Martini et al). Pharmaceutical compositions or combinations (or components thereof) of the disclosure for transdermal delivery include but are not limited to colloids, patches, and microemulsions.

Other suitable administration forms for the pharmaceutical compositions or combinations (or one or more of their components) of the disclosure include depot injectable formulations, suppositories, sprays, ointments, cremes, gels, inhalants, dermal patches, implants, devices, formulations for ocular administration, etc.

The pharmaceutical compositions or combinations of the disclosure, or one or more of their components, may also comprise adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the pharmaceutical compositions or combinations or components. In addition, prolonged absorption of the injectable pharmaceutical form may be brought about by the inclusion of agents which delay absorption, such as aluminum monostearate and gelatin.

Pharmaceutical compositions or combinations of the disclosure can be prepared by methods well known in the art of pharmacy, see, e.g., Goodman et al., 2001; Ansel, et al., 2004; Stoklosa et al., 2001; and Bustamante, et al., 1993.

In some embodiments, the pharmaceutical compositions and/or combinations according to this disclosure comprise a crystalline form of Compound 1 (e.g., Form A, Form B, Form C, Form E or Form F) in an amount of 0.05 mg to 5000 mg or 5 mg to 1000 mg. In some embodiments, the pharmaceutical composition may comprise about 0.5 mg, about 5 mg, about 20 mg, about 50 mg, about 75 mg, about 100 mg, about 150 mg, about 250 mg, about 500 mg, about 750 mg, about 1000 mg, about 1250 mg, about 2500 mg, about 3500 mg, or 5000 mg of the crystalline form of Compound 1.

In some embodiments of pharmaceutical compositions and/or combinations comprising an SV2A inhibitor (e.g., levetiracetam, brivaracetam, or seletracetam), or the pharmaceutically acceptable salt, hydrate, solvate, polymorph, or isomer thereof, the SV2A inhibitor (e.g., levetiracetam, brivaracetam, or seletracetam), or the pharmaceutically acceptable salt, hydrate, solvate, polymorph, or isomer thereof, is present in an amount of 0.07 mg-60 mg, 0.07 mg-350 mg, 3 mg-50 mg, 3 mg-60 mg, 25 mg-60 mg, 25 mg-125 mg, 50 mg-250 mg, 5 mg-140 mg, 0.7 mg-180 mg, 125 mg-240 mg, or 190-220 mg. In some embodiments of pharmaceutical compositions and/or combinations comprising an SV2A inhibitor (e.g., levetiracetam, brivaracetam, or seletracetam), or the pharmaceutically acceptable salt, hydrate, solvate, polymorph, or isomer thereof, the SV2A inhibitor (e.g., levetiracetam, brivaracetam, or seletracetam), or the pharmaceutically acceptable salt, hydrate, solvate, polymorph, or isomer thereof, is present in an amount of 220 mg.

Methods of Producing Crystalline Forms of Compound 1

The exemplary methods according to the present disclosure are useful for producing a crystalline form of Compound 1. In some embodiments, the present disclosure is directed to a method for producing a crystalline form of Compound 1, wherein the crystalline form is Form A, Form B, Form C, Form E or Form F. In some embodiments, the methods according to the present disclosure are directed to producing crystalline Form A of Compound 1.

In some embodiments, the methods of the present disclosure are directed to a method of producing an anhydrous crystalline form, Form A, of Compound 1, the method comprising:

- a. dissolving the compound in a first solvent to produce a solution at a first temperature;
- b. adding a second solvent to the solution to form a mixture;
- c. optionally cooling the mixture to a second temperature; and
- d. recovering the resulting precipitate to afford the anhydrous crystalline form, Form A, of the compound.

In some embodiments according to the disclosure, the first and second solvents are selected from the group consisting of acetone, acetonitrile, tetrahydrofuran, dichloromethane, dimethylformamide, ethanol, methanol, ethyl acetate, diethyl ether, toluene, water, or any mixtures thereof.

In some embodiments, the first solvent is dichloromethane, dimethylformamide, tetrahydrofuran, or any mixtures thereof. In some embodiments, the first solvent is dimethylformamide.

The first solvent can be added to Compound 1 using a number of methods recognizable to those skilled in the art. For example, the solvent can be added to Compound 1 by pouring, pipetting or canula transferring the solvent into a container containing Compound 1. Alternatively, Compound 1 can be added to a container containing the solvent. In some embodiments, the solution comprising the first solvent and Compound 1 are agitated, e.g., by stirring, to aid in the dissolution of Compound 1. In some embodiments, the solution comprising the solvent and Compound 1 is adjusted to a first temperature to aid in the dissolution of Compound 1. In some embodiments, the first temperature is ambient temperature, e.g., between about 20° C. and about 22° C. In some embodiments, the first temperature is at least 20° C. In some embodiments, the solution comprising the first solvent and Compound 1 is dilute, concentrated, nearly saturated, or saturated. In some embodiments, the solution comprising the first solvent and Compound 1 is nearly saturated or saturated.

In some embodiments, the second solvent in the methods according to this disclosure an anti-solvent (i.e., a solvent Compound 1 is partially soluble or not soluble in), and is selected to induce precipitation of a crystalline form of Compound 1 (e.g., crystalline Form A) from solution. The skilled worker can determine which solvents Compound 1 is soluble through routine experimentation in the art. In some embodiments, the second solvent is ethanol, methanol, ethyl acetate, diethyl ether, toluene or water. In some embodiments, the second solvent is water. The second solvent can be added to the mixture using techniques known to those skilled in the art. For example, the second solvent can be added to the solution by pouring, pipetting or canula transferring the second solvent into the solution to form a mixture.

In some embodiments, the methods optionally further comprise adjusting the first temperature to a second temperature that is different from the first temperature in order to induce precipitation of the crystalline form of Compound 1 (e.g., crystalline Form A). In some embodiments, the second temperature is below the first temperature. In some embodiments, the second temperature is ambient temperature (i.e., between about 20° C. and 22° C.). In some embodiments, the second temperature is less than about 20° C. In some embodiments, the temperature is between about −30° C. and about 20° C. In some embodiments, the second temperature is between 0° C. and 20° C., e.g., 1, 2, 3, 4, 5, 6, 7, 8, 9, 10, 11, 12, 13, 14, 15, 16, 17, 18, or 19° C. In some embodiments, the second temperature is between about 0° C. and about 20° C., e.g., about 1, about 2, about 3, about 4, about 5, about 6, about 7, about 8, about 9, about 10, about 11, about 12, about 13, about 14, about 15, about 16, about 17, about 18, or about 19° C. In some embodiments, the mixture is not adjusted to a second temperature. As those skilled in the art will recognize, the length of time during which the mixture is maintained at the second temperature can vary based on the concentration of the solution, and the temperature at which the solution is being held. In some embodiments, the mixture is maintained at the second temperature for between 1 hour and 7 days. In some embodiments, the mixture is maintained at the second temperature for at least 1 hour, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days or 7 days. In some embodiments, the mixture is maintained at the second temperature for at least 1 day, 2 days or 3 days. In some embodiments, the mixture is maintained at the second temperature for between about 1 hour and about 7 days.

The methods according to this disclosure further comprise recovering the resulting precipitate from the mixture. The precipitate can be recovered using methods known to those skilled in the art, e.g., filtering the precipitate, decanting the mother liquor into a separate container to leave behind the precipitate, or removing the mother liquor with a pipette.

In another embodiment, this disclosure provides a method of producing a crystalline form of Compound 1 (e.g., Form A), the method comprising:

- a. dissolving the compound in a solvent to form a solution;
- b. evaporating the solvent to produce a precipitate; and
- c. recovering the precipitate to afford the crystalline form of Compound 1 (e.g., anhydrous crystalline Form A).

In some embodiments, the solvent is selected from the group consisting of acetone, acetonitrile, tetrahydrofuran, dichloromethane, dimethylformamide, ethanol, methanol, ethyl acetate, diethyl ether, toluene, water, or any mixtures thereof. In some embodiments, the solvent is dichloromethane, dimethylformamide, tetrahydrofuran, or any mixtures thereof.

The solvent can be evaporated from the solution using a number of methods known to those skilled in the art, e.g., evaporation under a flow of an inert gas, e.g., nitrogen, flash evaporation (i.e., evaporation under reduced pressure), evaporation at elevated temperature, or a combination thereof. In some embodiments, the solvent is evaporated under a flow of inert gas, e.g., nitrogen. In some embodiments, the solvent is evaporated under reduced pressure. In some embodiments, the solvent is evaporated while heating the solution under reduced pressure. The temperature to which the solution is heated can depend on the boiling point of the solvent. In some embodiments, the solution is heated to at least the boiling point of the solvent. In some embodiments, the solvent is heated to below the boiling point of the solvent. In some embodiments, the solution is heated to between about 30° C. and about 170° C. In some embodiments, the solution is heated to between about 50° C. and about 150° C., or between about 70° C. and about 120° C., or between about 80° C. and about 110° C. In some embodiments, the solution is heated to at least 80° C. The extent to which the solvent is evaporated can vary. In some embodiments, the solvent is evaporated to dryness (i.e., such that, at most, only trace amounts of the solvent remain). In some embodiments, the solvent is evaporated until a precipitate is formed.

The methods further comprise recovering the precipitate to afford the crystalline form of Compound 1 (i.e., anhydrous crystalline Form A). The precipitate can be collected using methods known to those skilled in the art, e.g., collecting with a spatula, filtering the remaining solvent, decanting the remaining solvent, or removing the remaining solvent from the precipitate with a pipette.

In another embodiment, the disclosure provides a method of producing a methanolate crystalline form, Form C, of Compound 1 the method comprising:

a. combining the compound in a methanol to form a mixture;

b. mixing the mixture for a period of time;

c. optionally evaporating the methanol from the mixture; and d. recovering the precipitate to afford the methanolate crystalline form, Form C, of the compound.

The methanol can be added to Compound 1 using a number of methods recognizable to those skilled in the art. For example, the solvent can be added to Compound 1 by pouring, pipetting or canula transferring the methanol into a container containing Compound 1. As another example, Compound 1 can be added to a container already containing methanol. In some embodiments, methanol and Compound 1 are combined to form a slurry.

The mixture can be mixed for a period of time ranging from 30 minutes to 1 day. In some embodiments, the mixture is mixed for 30 minutes or for 1 day.

In some embodiments, the methanol is evaporated after the mixture has been mixed for a period of time. The methanol can be evaporated using a number of methods known to those skilled in the art. For example, the mixture can be dried by removing the solvent under reduced pressure, or under a stream of an inert gas, e.g., nitrogen. Alternatively, the mixture can be dried under reduced pressure and elevated temperature. In some embodiments, the mixture is dried under reduced pressure at a temperature of at least 40° C. In certain such embodiments, the temperature is between about 40° C. and about 70° C. In some embodiments, the mixture is not dried. In some embodiments, the solvent is evaporated to dryness (i.e., such that, at most, trace amounts of methanol remain). In other embodiments, the solvent is removed to concentrate the mixture to induce precipitation, i.e., by forming a saturated solution.

The precipitate can be recovered using any methods known to those skilled in the art. For example, the precipitate can be recovered by filtering the solution to isolate the precipitate. Alternatively, the precipitate can be recovered by decanting the mother liquor or removing the mother liquor with a pipette.

In another embodiment, the disclosure provides a method of producing a desolvated crystalline form, Form B, of Compound 1 the method comprising:

a. obtaining methanolate Form C of the compound;

b. heating the compound for a period of time to form the desolvated crystalline form, Form B, of the compound.

Methanolate Form C of Compound 1 can be obtained using the methods described herein.

The methods comprise heating methanolate Form C in order to drive out the solvent to produce desolvate Form B. In some embodiments, methanolate Form C is heated above ambient temperature. In some embodiments, methanolate Form C is heated to at least 60° C. In some embodiments, methanolate Form C is heated to between about 60° C. and about 150° C. In some embodiments, methanolate Form C is heated to between about 60° C. and about 100° C. In some embodiments, methanolate Form C is heated to at least 80° C.

In some embodiments, methanolate Form C is heated for at least 1 hour, 2 hours, 4 hours, 3 hours, 4 hours, 5 hours or 6 hours. In some embodiments, methanolate Form C is heated for between 1 hour and 24 hours, e.g., 1, 2, 3, 4, 5, 6, 7, 8, 9, 10, 11, 12, 13, 14, 15, 16, 17, 18, 19, 20, 21, 22, 23 or 24 hours. In some embodiments, methanolate Form C is heated for between about 1 hour and about 24 hours, e.g., about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 hours.

In another embodiment, the disclosure provides a method of producing a monohydrate crystalline form, Form F, of Compound 1, the method comprising:

a. obtaining a hydrochloride salt of the compound;

b. adding the hydrochloride salt of the compound to a solvent to form a mixture;

c. mixing the mixture for a period of time;

d. recovering the precipitate to afford the monohydrate crystalline form, Form F, of the compound.

In some embodiments, the hydrochloride salt of Compound 1 is obtained by reacting Compound 1 with hydrochloric acid. Compound 1 can be reacted with hydrochloric acid by dissolving Compound 1 in a solvent and adding stoichiometric amounts, or an excess of HCl to the mixture. The solvent can be selected from the group consisting of acetone, acetonitrile, tetrahydrofuran, dichloromethane, dimethylformamide, ethanol, methanol, ethyl acetate, diethyl ether, toluene, water, or any mixtures thereof. In some embodiments, the hydrochloride salt is isolated prior to its use in producing monohydrate crystalline form, Form F. The hydrochloride salt can be isolated according to methods known to those skilled in the art, e.g., filtration, drying under reduced pressure recrystallization, etc.

The solvent that the hydrochloride salt is added to in step (b) of the method can be selected from the group consisting of acetone, acetonitrile, tetrahydrofuran, dichloromethane, dimethylformamide, ethanol, methanol, ethyl acetate, diethyl ether, toluene, water, or any mixtures thereof. In some embodiments, the solvent is water. The mixture is then subsequently mixed (i.e., agitated or stirred) for a period of time ranging between 1 day and 14 days. In some embodiments, the mixture is mixed for at least 1 day. In another embodiment, the mixture is mixed for at least 6 days.

The precipitate can then be recovered using any methods known to those skilled in the art. For example, the precipitate can be recovered by filtering the solution to isolate the precipitate. Alternatively, the precipitate can be recovered by decanting the mother liquor or removing the mother liquor with a pipette.

In another embodiment, the disclosure provides a method of producing an anhydrous crystalline form, Form E, of Compound 1, the method comprising:

a. dissolving the compound in tetrahydrofuran at a first temperature to form a solution;
b. adjusting the first temperature to a second temperature to induce precipitation;
c. recovering the precipitate to afford the anhydrous crystalline form, Form E, of the compound.

In some embodiments, the first temperature is ambient temperature, e.g., between about 20° C. and 22° C. In some embodiments, the first temperature is at least 20° C. In some embodiments, the first temperature is between about 20° C. and about 66° C. In some embodiments, the solution comprising the first solvent and Compound 1 is dilute, concentrated, nearly saturated, or saturated. In some embodiments, the solution comprising the first solvent and Compound 1 is nearly saturated or saturated.

In some embodiments, the methods optionally further comprise adjusting the first temperature to a second temperature that is different from the first temperature in order to induce precipitation of the crystalline form of Compound 1 (e.g., anhydrous crystalline Form E). In some embodiments, the second temperature is below the first temperature. In some embodiments, the second temperature is less than 66° C. In some embodiments, the second temperature is less than 20° C. In some embodiments, the temperature is between about −30° C. and about 30° C. In some embodiments, the second temperature is between 0° C. and 20° C., e.g., 1, 2, 3, 4, 5, 6, 7, 8, 9, 10, 11, 12, 13, 14, 15, 16, 17, 18, or 19° C. In some embodiments, the second temperature is between about 0° C. and about 20° C., e.g., about 1, about 2, about 3, about 4, about 5, about 6, about 7, about 8, about 9, about 10, about 11, about 12, about 13, about 14, about 15, about 16, about 17, about 18, or about 19° C. As those skilled in the art will recognize, the length of time during which the mixture is maintained at the second temperature can vary based on the concentration of the solution, and the temperature at which the solution is being held. In some embodiments, the mixture is maintained at the second temperature for between 1 hour and 7 days. In some embodiments, the mixture is maintained at the second temperature for at least 1 hour, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days or 7 days. In some embodiments, the mixture is maintained at the second temperature for at least 1 day, 2 days or 3 days. In some embodiments, the mixture is maintained at the second temperature for between about 1 hour and about 7 days.

It will be understood by one of ordinary skill in the art that the methods described herein may be adapted and modified as is appropriate for the application being addressed and that the methods described herein may be employed in other suitable applications, and that such other additions and modifications will not depart from the scope hereof.

This disclosure will be better understood from the Examples and experimental details which follow. However, one skilled in the art will readily appreciate that the specific methods and results discussed are merely illustrative of the invention as described more fully in the embodiments which follow thereafter.

EXAMPLES

Example 1: Synthesis of Compound 1

Scheme 1: Synthesis of Compound 1

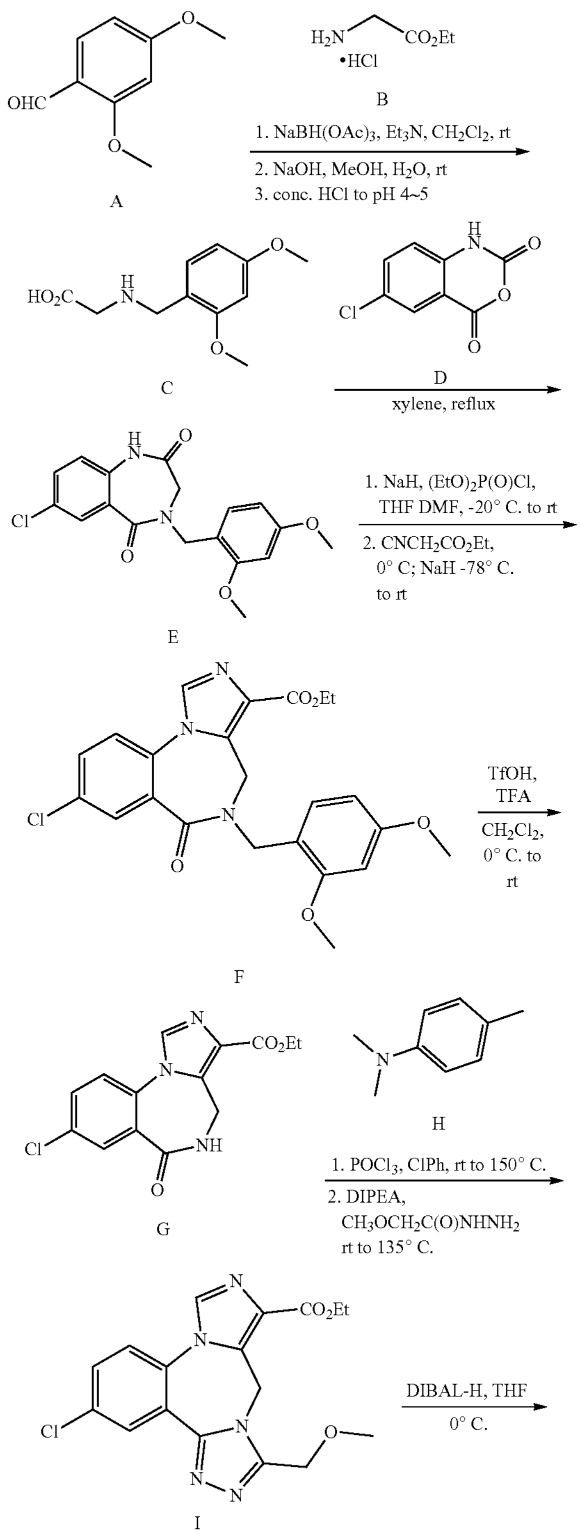

-continued

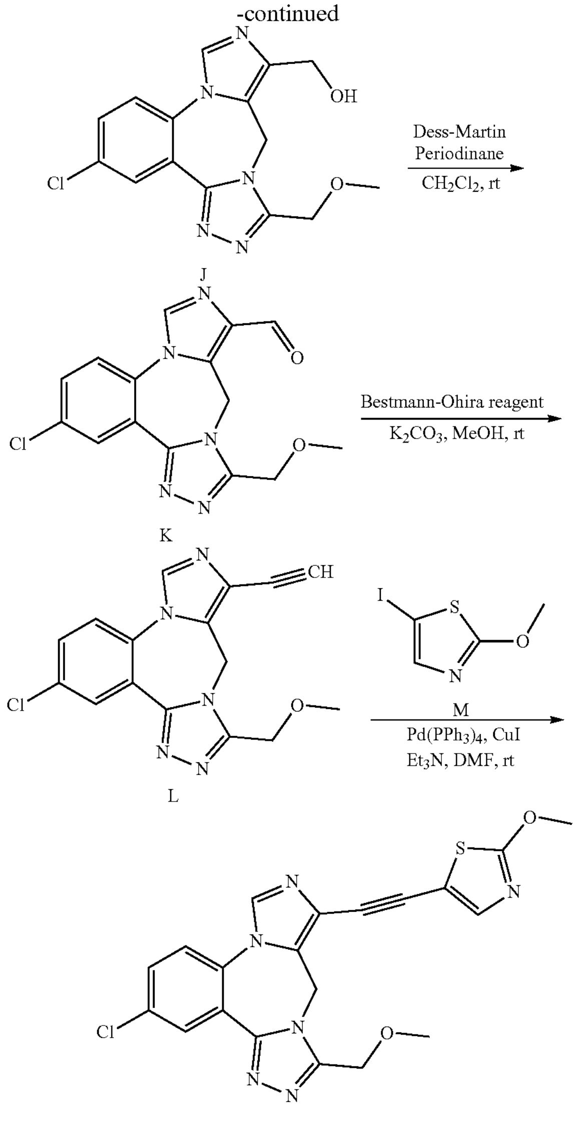

J

K

L

1

Preparation of 2-((2,4-dimethoxybenzyl)amino)acetic acid (C)

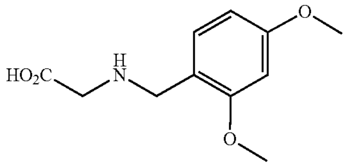

C

A mixture of compound A (40.0 g, 240 mmol), compound B (50.2 g, 360 mmol), and $Et_3N$ (50.2 mL, 360 mmol) in anhydrous $CH_2Cl_2$ (800 mL) was stirred at rt under $N_2$ for 1 h. After this time, $NaBH(OAc)_3$ (76.4 g, 360 mmol) was added portionwise over 20 min with a cold water cooling bath (exothermal). The resulting mixture was stirred at rt for overnight. The reaction mixture was then cooled with an ice/water bath and quenched by slow addition of saturated $NaHCO_3$ aqueous solution (~800 mL). The resulting mixture was stirred for 30 min. The layers were separated. The aqueous layer was extracted with $CH_2Cl_2$ (2×500 mL). The combined organic layers were washed with saturated $NaHCO_3$ aqueous solution (300 mL) and water (300 mL), dried over anhydrous $Na_2SO_4$, filtered, and concentrated under reduced pressure. The residue was dissolved in methanol (320 mL). NaOH aqueous solution (2 N, 360 mL) was added. The reaction mixture was stirred at rt for 2 h. After this time, the reaction mixture was cooled with an ice/water bath and acidified by slow addition of concentrated HCl (~12 N) to pH 4-5. The resulting mixture was concentrated under reduced pressure. The residue was added water (80 mL) and stirred at 70° C. bath until all solid dissolved. The resulting solution was cooled with an ice/water bath and ultrasonicated for 10 min. The solid was collected by filtration and dried under high vacuum to give compound C as a white solid (44.3 g, 82%): $^1H$ NMR (500 MHz, DMSO-$d_4$) δ 7.26 (d, J=8.3 Hz, 1H), 6.59 (d, J=2.4 Hz, 1H), 6.53 (dd, J=8.3, 2.4 Hz, 1H), 3.92 (s, 2H), 3.80 (s, 3H), 3.77 (s, 3H), 3.04 (s, 2H).

Preparation of 7-chloro-4-(2,4-dimethoxybenzyl)-3,4-dihydro-1H-benzo[e][1,4]diazepine-2,5-dione (E)

E

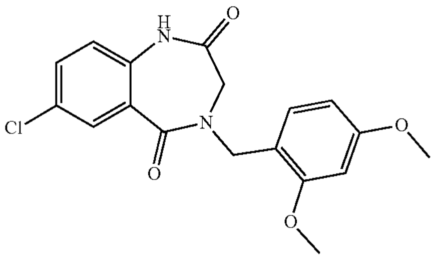

A suspension of compound C (12.5 g, 55.5 mmol) and compound D (10.0 g, 50.6 mmol) in xylenes (140 mL) was heated to reflux with stirring under $N_2$ for 3 h. After this time, the reaction mixture was cooled to rt and concentrated under reduced pressure to dryness. The residue was triturated with EtOAc/methanol (10:1, ~40 mL) and filtered. The filter cake was dried under high vacuum to give compound E as an off-white solid (14.0 g, 77%): ESI MS, m/z=361 $[M+H]^+$.

Preparation of ethyl 8-chloro-5-(2,4-dimethoxybenzyl)-6-oxo-5,6-dihydro-4H-benzo[f]imidazo[1,5-a][1,4]diazepine-3-carboxylate (F)

F

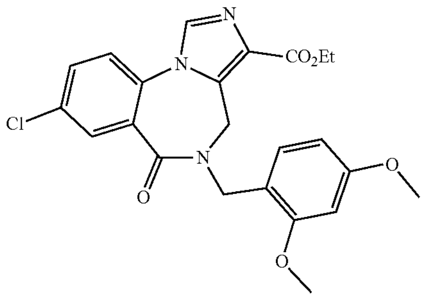

To a stirred solution of compound E (23.0 g, 63.7 mmol) in anhydrous THF (250 mL) and anhydrous DMF (125 mL) was added NaH (60% in mineral oil, 3.82 g, 95.5 mmol) at −20° C. under $N_2$. The resulting mixture was warmed to rt and stirred at rt for 30 min. After this time, the reaction mixture was cooled to −20° C. and $(EtO)_2P(O)Cl$ (13.8 mL, 95.5 mmol) was added. The resulting mixture was then warmed to rt and stirred at rt for 2.5 h. The reaction mixture was cooled with an ice/water bath and $CNCH_2CO_2Et$ (10.4 mL, 95.2 mmol) was added. The resulting mixture was stirred at 0° C. for 5 min and then cooled to −78° C. NaH (60% in mineral oil, 3.82 g, 95.5 mmol) was added. The reaction mixture was stirred at −78° C. for 10 min and slowly warmed to rt overnight. After this time, the reaction mixture was quenched with half saturated $NaHCO_3$ aqueous solution (400 mL), extracted with EtOAc (3×400 mL). The combined extracts were washed with 10% LiCl aqueous solution (2×100 mL) and brine (100 mL), dried over anhydrous $Na_2SO_4$, filtered, and concentrated under reduced pressure. The resulting residue was purified by flash column chromatography on silica gel eluting with 80% to 100% $EtOAc/CH_2Cl_2$ to afford compound F as an off-white solid (18.3 g, 63%): ESI MS, m/z=456 $[M+H]^+$.

Preparation of ethyl 8-chloro-6-oxo-5,6-dihydro-4H-benzo[f]imidazo[1,5-a][1,4]diazepine-3-carboxylate (G)

G

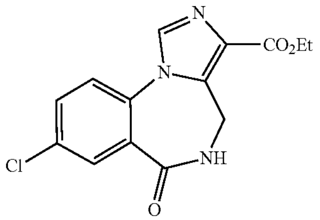

To a stirred solution of compound F (18.3 g, 40.1 mmol) in anhydrous $CH_2Cl_2$ (96 mL) was added TFA (48 mL) followed by TfOH (7.1 mL, 80.8 mmol) at 0° C. The reaction mixture was warmed to rt and stirred for 2 h. After this time, the reaction mixture was concentrated under reduced pressure. The residue was diluted with $CH_2Cl_2$ (300 mL), cooled with an ice/water bath, and basified by slow addition of saturated $NaHCO_3$ aqueous solution to pH>7. The mixture was filtered. The filter cake was washed with water (2×30 mL). The layers of filtrate were separated. The aqueous layer was extracted with $CH_2Cl_2$ (4×300 mL). The combined organic layers were washed with water (100 mL), dried over anhydrous $Na_2SO_4$, filtered, and concentrated under reduced pressure. The resulting residue was triturated with EtOAc and filtered. The combined filter cakes were dried under high vacuum to afford compound G as an off-white solid (12.9 g, >99%): ESI MS, m/z=306 $[M+H]^+$.

Preparation of ethyl 3-chloro-7-(methoxymethyl)-9H-benzo[f]imidazo[1,5-a][1,2,4]triazolo[4,3-d][1,4]diazepine-10-carboxylate (I)

I

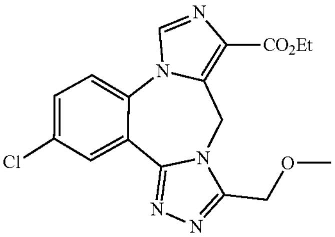

To a stirred suspension of compound G (12.9 g, ca. 40.1 mmol) and compound H (23.1 mL, 160 mmol) in chlorobenzene (400 mL) was added $POCl_3$ (7.5 mL, 80.5 mmol) at rt under $N_2$. The reaction mixture was heated in a 150° C. oil bath (refluxed) with stirring for 2.5 h. After this time, the reaction mixture was cooled to rt and $CH_3OCH_2C(O)NHNH_2$ (25.0 g, 240 mmol) was added followed by DIPEA (35 mL, 201 mmol). The resulting mixture was stirred at rt for 30 min and then heated in a 135° C. oil bath for 1.5 h. After this time, the reaction mixture was cooled to rt, diluted with $CH_2Cl_2$ (500 mL), quenched with saturated $NaHCO_3$ aqueous solution (500 mL). The layers were separated. The aqueous layer was extracted with $CH_2Cl_2$ (4×300 mL). The combined organic layers were dried over anhydrous $Na_2SO_4$, filtered, and concentrated under reduced pressure. The resulting residue was purified by flash column chromatography on silica gel eluting with 0% to 8% MeOH/EtOAc to afford compound I as a light yellow solid (11.5 g, 77%): ESI MS, m/z=374 $[M+H]^+$. Also recovered compound G (1.80 g).

Preparation of (3-chloro-7-(methoxymethyl)-9H-benzo[f]imidazo[1,5-a][1,2,4]triazolo[4,3-d][1,4]diazepin-10-yl)methanol (J)

J

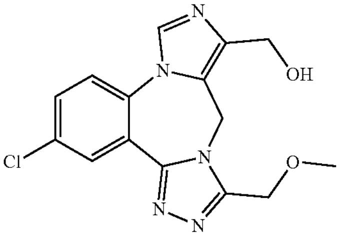

To a stirred solution of compound I (3.74 g, 10.0 mmol) in anhydrous THF (40 mL) was added DIBAL-H (1 M in THF, 30 mL, 30 mmol) dropwise over 10 min at 0° C. under $N_2$. The reaction mixture was stirred at 0° C. for 2.5 h. After this time, the reaction mixture was quenched with saturated Rochelle's salt aqueous solution (40 mL) and water (50 mL). The resulting mixture was stirred at rt for 1.5 h. The solid was filtered and washed with water (10 mL) and EtOAc (10 mL). The layers of filtrate were separated. The aqueous layer was extracted with EtOAc (3×30 mL). The combined organic layers were dried over $Na_2SO_4$, filtered, and concentrated under reduced pressure. The resulting residue was triturated with EtOAc (5 mL) and filtered. The combined filter cakes were dried under high vacuum to afford compound G as a light yellow solid (2.95 g, 89%): ESI MS, m/z=354 $[M+Na]^+$.

Preparation of 3-chloro-7-(methoxymethyl)-9H-benzo[f]imidazo[1,5-a][1,2,4]triazolo[4,3-d][1,4]diazepine-10-carbaldehyde (K)

K

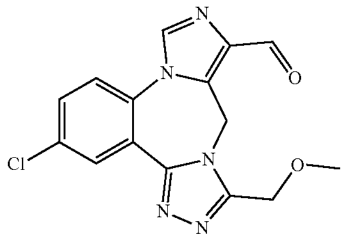

To a stirred suspension of compound J (2.95 g, 8.89 mmol) in anhydrous $CH_2Cl_2$ (50 mL) was added Dess-Martin periodinane (4.53 g, 10.7 mmol) at 0° C. under $N_2$. The reaction mixture was stirred at 0° C. for 10 min and then warmed to rt for 3 h. After this time, the reaction mixture was quenched with methanol (5 mL) and stirred at rt for 1 h. The resulting mixture was added brine (50 mL). The layers were separated. The aqueous layer was extracted with EtOAc (3×50 mL). The combined organic layers were dried over anhydrous $Na_2SO_4$, filtered, and concentrated under reduced pressure. The resulting residue was purified by flash column chromatography on silica gel eluting with EtOAc; then 0% to 10% MeOH/$CH_2Cl_2$ to afford compound K as a white solid (2.62 g, 89%): ESI MS, m/z=330 $[M+H]^+$.

Preparation of 3-chloro-10-ethynyl-7-(methoxymethyl)-9H-benzo[f]imidazo[1,5-a][1,2,4]triazolo[4,3-d][1,4]diazepine (L)

L

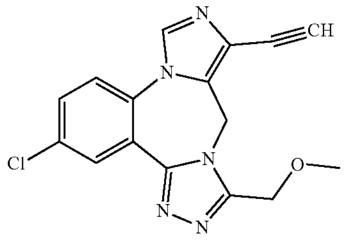

To a stirred solution of compound K (2.62 g, 7.95 mmol) in anhydrous MeOH (70 mL) was added $K_2CO_3$ (2.20 g, 15.9 mmol) followed by Bestmann-Ohira reagent (2.29 g, 11.9 mmol) at rt under $N_2$. The reaction mixture was stirred at rt for overnight. After this time, the reaction mixture was quenched with saturated $NaHCO_3$ aqueous solution. The resulting mixture was extracted with $CH_2Cl_2$ (3×50 mL). The combined extracts were concentrated under reduced pressure. The residue was dissolved in $CH_2Cl_2$ (200 mL), washed with water (30 mL), dried over anhydrous $Na_2SO_4$, filtered, and concentrated under reduced pressure. The resulting residue was triturated with $CH_2Cl_2$ (10 mL) and filtered. The filtrate was purified by flash column chromatography on silica gel eluting with 2% to 4% MeOH/EtOAc. The product obtained from column purification was combined with the filter cake and dried under high vacuum to afford compound L as a white solid (1.96 g, 76%): ESI MS, m/z=326 $[M+H]^+$.

Preparation of 5-((3-chloro-7-(methoxymethyl)-9H-benzo[f]imidazo[1,5-a][1,2,4]triazolo[4,3-d][1,4]diazepin-10-yl)ethynyl)-2-methoxythiazole (1)

1

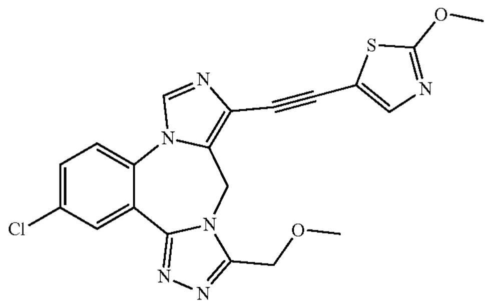

A suspension of compound L (500 mg, 1.53 mmol), compound M (see synthesis below) (1.10 g, 4.60 mmol), and CuI (87 mg, 0.460 mmol) in anhydrous DMF (15 mL) was bubbled with argon for 5 min. After this time, $Et_3N$ (1.07 mL, 7.65 mmol) was added followed by Pd $(PPh_3)_4$(353 mg, 0.306 mmol). The resulting mixture was stirred at rt under argon for overnight. The reaction mixture was then diluted with water (50 mL) and extracted with EtOAc (4×50 mL). The combined extracts were washed with 10% LiCi aqueous solution (2×20 mL), brine (20 mL), dried over anhydrous $Na_2SO_4$, filtered, and concentrated under reduced pressure. The resulting residue was purified by flash column chromatography on silica gel eluting with 0% to 5% MeOH/$CH_2Cl_2$ to afford Compound 1 as a light grey solid (468 mg, 69%): $^1H$ NMR (300 MHz, DMSO-$d_6$) δ 8.36 (s, 1H), 8.08 (d, J=2.3 Hz, 1H), 7.97 (d, J=8.7 Hz, 1H), 7.87 (dd, J=8.7, 2.3 Hz, 1H), 7.62 (s, 1H), 5.43 (s, 2H), 4.76 (s, 2H), 4.09 (s, 3H), 3.31 (s, 3H); ESI MS, m/z=439 $[M+H]^+$.

General Procedures for Salt and Polymorph Screening

Anti-Solvent Additions

Solutions were contacted with anti-solvents. These anti-solvent additions were added to help lower the solubility of the solvent system and induce crystallization.

Cooling and Slow Cools

Solutions were prepared in the selected solvent or solvent/anti-solvent system. These solutions were chilled below room temperature within a refrigerator for varying lengths of time in an attempt to induce nucleation. The presence or absence of solids was noted. Upon observation of solids, in quantities sufficient for analysis, isolation of material was conduction. If insufficient quantities were present further cooling was performed in a freezer. Samples were either isolated for analysis wet or as dry powders.

Fast Evaporation

Solutions were prepared in selected solvents and agitated between aliquot additions to assist in dissolution. Once a mixture reached complete dissolution, as judged by visual observation, the solution was filtered through a 0.2-μm nylon filter and allowed to evaporate at ambient temperature in an uncapped vial or at ambient under nitrogen. The solids that formed were isolated for evaluation.

Slow Evaporation

Solutions were prepared in selected solvents and agitated between aliquot additions to assist in dissolution. Once a mixture reached complete dissolution, as judged by visual observation, the solution was filtered through a 0.2-μm nylon filter into a sample vial. The vial opening was covered with foil and pierced 3× to slow and allowed to evaporate at ambient. The solids that formed were isolated for evaluation.

Slurry

Solutions were prepared by adding enough solids to a given solvent so that excess solids were present. The mixture was then agitated in a sealed vial at either ambient or an elevated temperature. After a given amount of time, the solids were isolated for analysis.

Solubility Estimation

Aliquots of various solvents were added to measured amounts of a given material with agitation (typically sonication) at stated temperatures until complete dissolution was achieved, as judged by visual observation. If dissolution occurred after the addition of the first aliquot, values are reported as ">". If dissolution did not occur, values are reported as "<".

General Instrumental Techniques for Salt and Polymorph Screening

Differential Scanning Calorimetry (DSC)

DSC was performed using a Mettler-Toledo DSC3+ differential scanning calorimeter. A tau lag adjustment is performed with indium, tin, and zinc. The temperature and enthalpy are adjusted with octane, phenyl salicylate, indium, tin and zinc. The adjustment is then verified with octane, phenyl salicylate, indium, tin, and zinc. The sample was placed into a hermetically sealed aluminum DSC pan, the weight was accurately recorded, and the sample was inserted into the DSC cell. A weighed aluminum pan configured as the sample pan was placed on the reference side of the cell. The pan lid was pierced prior to sample analysis. The samples were analyzed from −25° C. to 250° C. at 10° C./min.

Dynamic Vapor Sorption (DVS)

Dynamic vapor sorption data was collected on a Surface Measurement System DVS Intrinsic instrument. The samples were not dried prior to analysis. Sorption and desorption data were collected over a range from 5% to 95% RH in 10% RH increments under a nitrogen purge. The equilibrium criteria used for the analyses were 0.001 dm/dt weight change in 5 minutes with a minimum step time of 30 minutes and maximum equilibration time of 180 minutes with a 3-minute data logging interval. Data were not corrected for the initial moisture content of the sample. The samples were identified as having low, limited or significant hygroscopicity based on the definitions in the below table.

| Term | Definition |
|---|---|
| Low hygroscopicity | Material exhibits <0.5 wt % water uptake over a specified RH range. |
| Limited hygroscopicity | Material exhibits <2.0 wt % water uptake over a specified RH range. |
| Significant hygroscopicity | Material exhibits ≥2.0 wt % water uptake over a specified RH range. |

Thermogravimetry (TGA or TGA/DSC)

Thermogravimetric analyses were performed using a Mettler-Toledo TGA/DSC3+ analyzer. Temperature calibration was performed using calcium oxalate, indium, tin, and zinc. The sample was placed in an aluminum pan. The pan was hermetically sealed, the lid was pierced, and the pan was then inserted into the TG furnace. A weighed aluminum pan configured as the sample pan was placed on the reference platform. The furnace was heated under nitrogen. Samples were analyzed from 25° C. to 350° C. at 10° C./min.

Thermogravimetric analyses typically experience a period of equilibration at the start of each analysis, indicated by red parentheses on the thermograms. The starting temperature for relevant weight loss calculations is selected at a point beyond this region (typically above 35° C.) for accuracy.

DSC analysis on this instrument is less sensitive than on the DSC3+ differential scanning calorimeter. Therefore, samples with sufficient solids were analyzed by both instruments and only the TGA thermogram from this instrument is reported.

X-Ray Powder Diffraction (XRPD)

Transmission Geometry (Most Samples)

XRPD patterns were collected with a PANalytical X'Pert PRO MPD or a PANalytical Empyrean diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 5.5. The data acquisition parameters for each pattern are displayed above the image in the Data section of this report. All images have the instrument labeled as X'Pert PRO MPD regardless of the instrument used.

Example 2: Salt Screen of Compound 1

Figure 19:
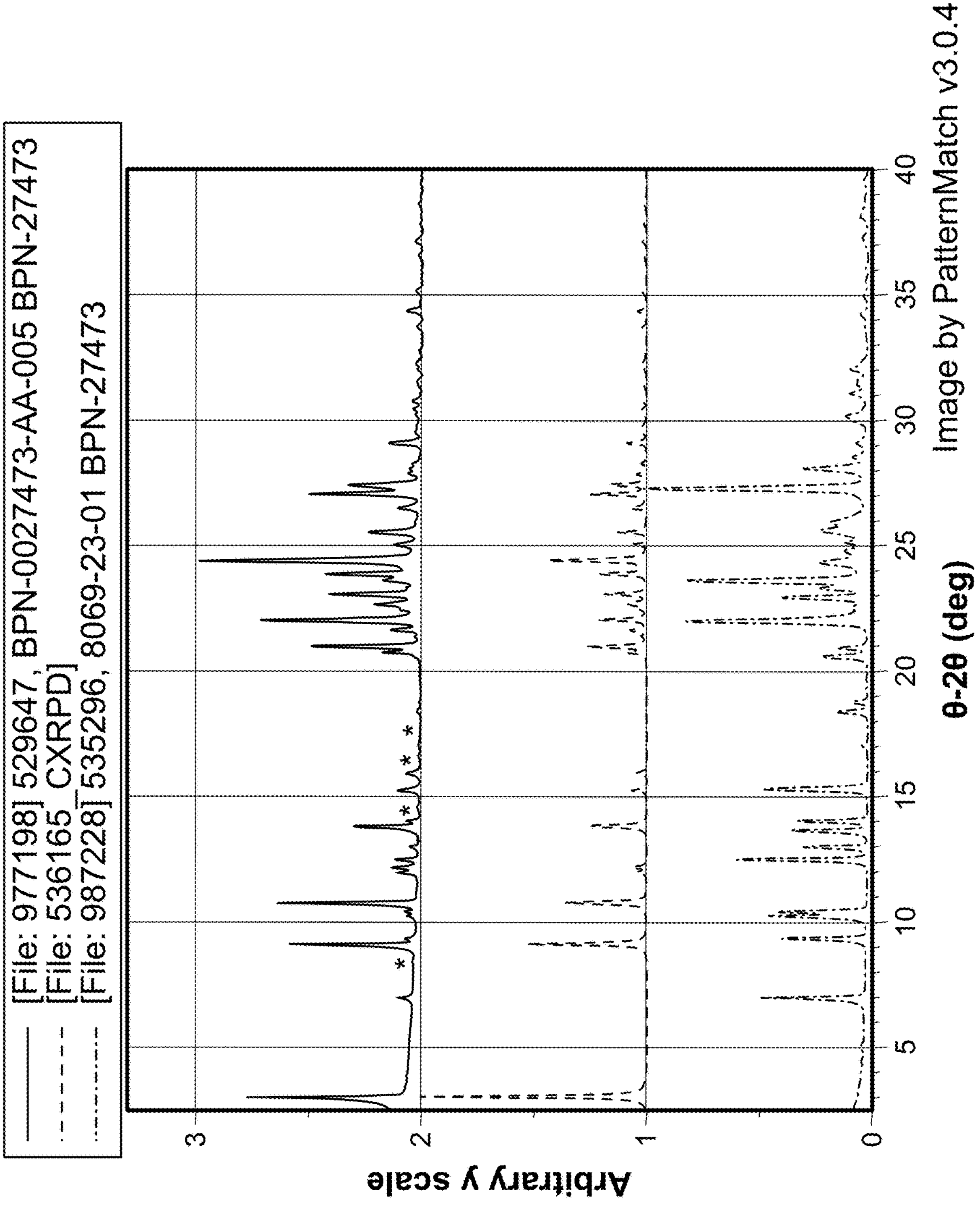
FIG. 19 is an XRPD overlay of crude Compound 1 (top), calculated Form A (middle), and experimental Form B (bottom). The * symbol denotes additional peaks not attributable to either Form A or Form B.

Unless otherwise indicated, reference to the use of Compound 1 in the below procedures refers to a mixture of Form A and Form B that is observable, in some circumstances, after carrying out the synthesis of Compound 1 (see FIG. 19), referred to herein as "crude".

Based on the weakly basic $pK_a$ values of Compound 1, strong acids were selected for salt formation. The eight strong acids used were hydrochloric, sulfuric, benzenesulfonic, ethane-1,2-disulfonic, methanesulfonic, naphthalene-1,5-disulfonic, naphthalene-2-sulfonic and toluenesulfonic.

These experiments generally involved the direct addition of 0.5, 1, or 2 molar equivalents of acidic solutions to solutions or suspensions of the free base form of Compound 1. Materials were harvested immediately if precipitation of sufficient quantity occurred. If necessary, additional steps including (but not limited to) cooling, anti-solvent addition, melting/cooling, evaporation, and/or slurrying were performed in attempts to increase yield or crystallinity of the resulting material.

The products were qualitatively evaluated for crystallinity by polarized light microscopy (PLM) and/or x-ray powder diffraction (XRPD). Crystalline materials were successfully isolated with all eight strong acids used. However, the edisylate salt was found to be decomposed as determined by $^1H$ NMR. With the exception of the edisylate, at least one representative crystalline salt from each counterion was isolated.

Example 3: Compound 1 Free Base Polymorph Screen

Unless otherwise indicated, reference to the use of Compound 1 in the below procedures refers to a mixture of Form A and Form B that is observable, in some circumstances, after carrying out the synthesis of Compound 1 (see FIG. 19), referred to herein as "crude".

A solvent-based screen designed to identify crystalline forms of Compound 1 is summarized in Table 1. More than 60 evaporative, slurry, crash precipitation, and cooling experiments were conducted. In some instances, solids were purposefully analyzed wet to further increase the likelihood of identifying hydrated or solvated forms. Water activity slurries were utilized to evaluate the propensity of Compound 1 to form hydrates and to help identify the stability range in which they would occur. Non-solvent based methods consisting of heat-induced transformations were also included. In addition, experiments to help determine the relative thermodynamic stability between anhydrous forms at various temperatures were conducted (see Example 4).

TABLE 1

Polymorph Experiments of Compound 1

| Solvent | Method | Observation[1] | Result (Observed Form) |
|---|---|---|---|
| acetone | slurry, ambient, 1 d | off white, yellow solution | A + B |
| ACN | slurry, ambient, 1 d | white, yellow solution | A + B |
| DCM | dissolved<br>treated w/charcoal<br>fast evaporation | yellow solution<br>reduction of hue<br>aciculars, B | A |
| | flash evap at 80° C. | solids formed rapidly, fine aciculars, B | A |
| | $N_2$ evaporation | off white solids, fines, oily areas | A |
| | solvent/anti-solvent<br>1 mL of DCM solution filtered into 10 ml $Et_2O$<br>10 ml of $Et_2O$ added | 1. turbid<br>2. fine aciculars, B | E + A |
| | rotary evaporation | off white fines, B | D + A + peaks |
| | rotary evaporation | fines, B | D + A |
| | seeded w/Form E of Compound 1<br>$N_2$ fast evaporation | —<br>— | A |
| | 1. saturated solution at ambient, filtered<br>2. seeded w/Form E of Compound 1<br>3. $Et_2O$ added | clear solution<br>seed retained<br>fine aciculars, B | A |
| | volume reduced w/heat<br>seeded w/Form E of Compound 1<br>cold $Et_2O$ added<br>filtered | clear solution<br>seed retained<br>precipitates formed<br>aciculars, B | A |
| | 1. saturated solution a ambient, filtered<br>2. seeded w/Form E of Compound 1 in cold $Et_2O$<br>3. filtered | clear solution<br>—<br>fine aciculars, B | A + E |
| DMF | solvent/anti-solvent<br>1. 80° C. DMF solution filtered into EtOH (RT) w/Form A of Compound 1<br>2. stirred, 1 hour<br>3. filtered, vacuum dried overnight | no changes<br>nucleation, ~2 min.<br>off-white solids | A |
| | solvent/anti-solvent<br>1. 80° C. DMF solution filtered into EtOH (RT) w/8010-94-03 (Form E)<br>filtered, EtOH wash<br>vacuum overnight | nucleation ~10 min.<br>—<br>— | A + E |

| Solvent | Method | Observation[2] | Result (Observed Form) |
|---|---|---|---|
| DMF | slow cool, 80° C.<br>treated with charcoal | white fine aciculars, B | A |
| | solvent/anti-solvent<br>1. DMF solution filtered into water | 1. gel, few fines, B | diffuse scatter |

TABLE 1-continued

| Polymorph Experiments of Compound 1 | | | |
|---|---|---|---|
| | 2. sub sample isolated on slide, smashed<br>3. bulk seeded with slide material<br>4. slurry, ambient, 1 d<br>5. centrifuged sub sample | 2. gel collapsed, fines<br>3. —<br>4. —<br>5. gel | |
| | 5. slurry Compound 1 centrifuged, decanted, dried under $N_2$ | would not filter | A |
| | solvent/anti-solvent<br>1. DMF solution filtered into ethanol<br>2. refrigerated, 3 d | clear solution<br>blades | A[3] |
| | solvent/anti-solvent 1 80° C. DMF solution filtered into EtOH (RT)<br>2. stirring<br>3. filtered, vacuum dried overnight | clear solution nucleation after ~2 min.<br>off-white solids | A |
| | 1. heated to reflux to reduce EtOH<br>2. water added slurry, 6 days filtered, rinsed w/water, $N_2$ dried | clear<br>no changes<br>aciculars after 2 days<br>light brown aciculars, B | A |
| $Et_2O$ | slurry, ambient, 1 d | off white, yellow solution | A + B |
| EtOH | slow cool, 50° C. | aciculars, wispy, B | A |
| EtOAc | slurry, ambient, 1 d | off white, yellow solution | A + B |
| MeOH | slurry, ambient, 1d | white, yellow solution | C |
| | 1. iterative wash<br>2. filter cake rinsed with DCM | white solids<br>— | C + peaks |
| | slurry, ambient, ½ hr, $N_2$ dried at 60° C. | — | C |
| | Form F MeOH, sonicated centrifuged, decanted | gel then broke<br>— | C + peaks |
| THF | fast evaporation | yellow dendritic, B | A |
| | slow cool | white fines, B | E |
| toluene | slurry, ambient, 1 d | off-white, yellow solution | A + B |
| **Solvent** | **Method** | **Observation[4]** | **Result (Observed Form)** |
| water | slurry, ambient, 1 d | tan solids, yellow solution | A + B |
| | Napsylate salt of Compound 1 and Form E of Compound 1 slurry, ambient, 8 d | gel and fines, B | disordered E |
| | Disordered E from above sub sampled after 2 days, centrifuge, left wet | gel | diffuse scatter |
| | HCl salt of Compound 1 slurry, ambient, 6 days | tan solids | disordered F |
| water/DMF | slurry, ambient, 19 d | — | A + B |
| 90:10 v/v (0.97 $a_w$) | A mixture of Form A and B of Compound 1 slurry, ambient, 6 d | — | A |
| | 1. 2 ml DMF solution (12 mg/mL) slowly added to 18 mL $H_2O$ seeded w/13.8 mg of Form F of Compound 1<br>2. subdivided | irregular mass, limited amount of fines, B<br>filtrate pH 4.5 | diffuse scatter + F |
| | Form F of Compound 1 left at ambient, 5 d | — | diffuse scatter + F |
| | Form F of Compound 1 left at ambient, 14 d | — | diffuse scatter + F |

TABLE 1-continued

| Polymorph Experiments of Compound 1 | | | |
|---|---|---|---|
| | Form F of Compound 1 55° C. slurry, 1 d continued 5 d total filtered, $N_2$ dried | solids settled, blades no changes low recovery | Form E |
| | Form F of Compound 1 dilute HCl added subdivided ambient, 5 d | pH: 1.5 — — | diffuse scatter + F |
| | Form F of Compound 1 ambient, 9 d | — — | diffuse scatter + F |
| water/DMF | slurry, ambient, 19 d | — | A + B |
| 50:50 v/v (0.70 $a_w$) | A mixture of Form A and B of Compound 1 slurry, ambient, 6 d | — | A + B |
| | 0.5 mL DMF solution (12 mg/mL) slowly added to 0.5 mL $H_2O$ seeded w/ 6.7 mg Form F | aciculars, B | A |
| water/DMF 25:75 v/v (0.45 $a_w$) | 1 mL water added slowly to 3 mL DMF solution (12 mg/mL) | aciculars after 5 min., B | A |
| | 1 mL water seeded w/ 8010-85-03 (Form F) added to 3 mL DMF solution (12 mg/mL) | aciculars, B | A |

[1]B = birefringent.
[2]B = birefringent.
[3]Single crystal isolated
[4]B = birefringent.

Figure 2:
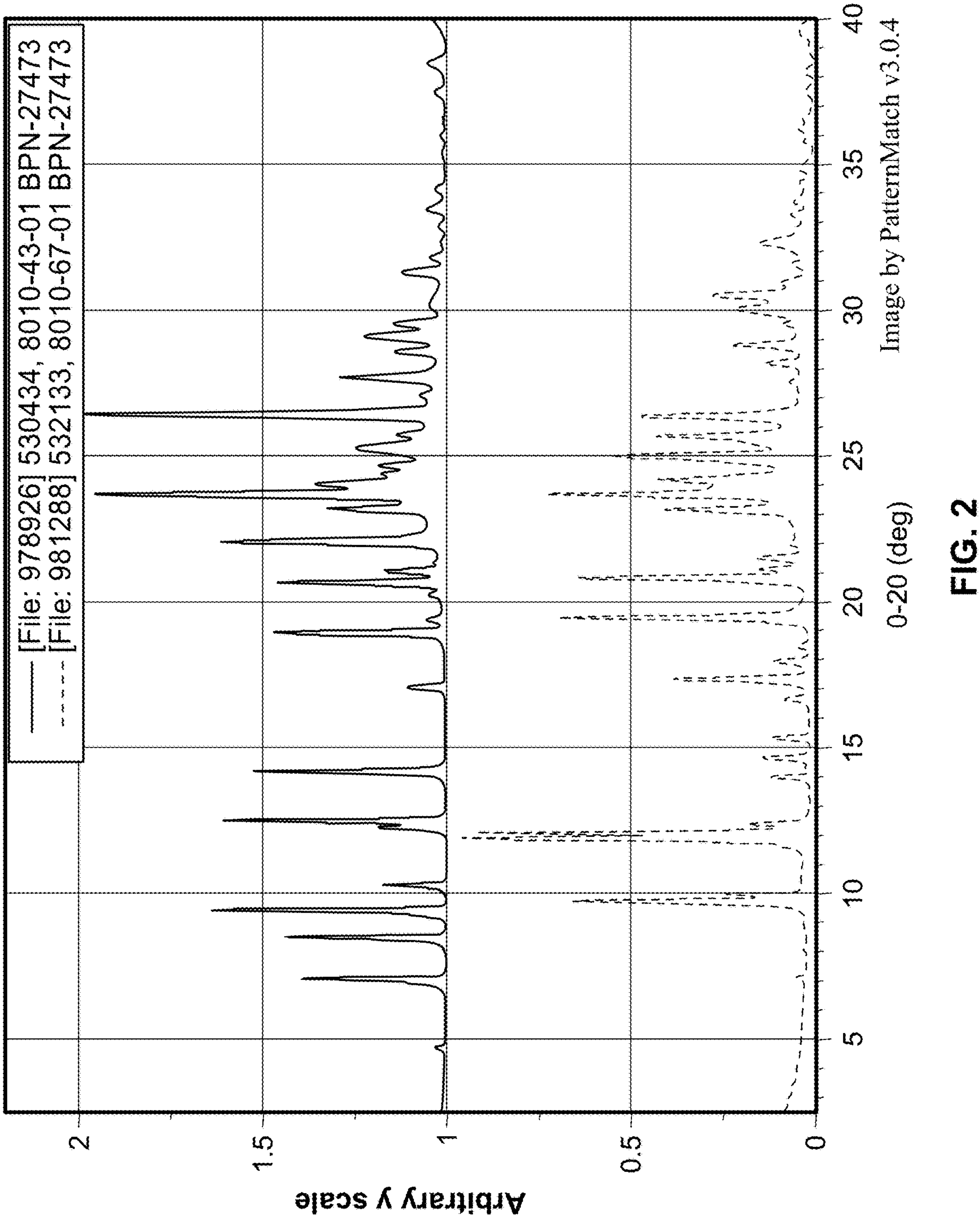
FIG. 2 is an XRPD pattern overlay of the solvated polymorphic forms of Compound 1. The top diffractogram corresponds to methanolate Form C, and the bottom corresponds to monohydrate Form F.

Forms A, B, Material D, and Form E are anhydrous forms of Compound 1; Form F is a hydrate; and Form C is a methanolate. The X-ray powder patterns of these forms are compared in FIGS. 1 and 2. Crystalline Form A Anhydrate of Compound 1 exhibits limited hygroscopicity, a decomposition onset of 207° C., and was identified as the most thermodynamically stable, relative to the other anhydrous forms of Compound 1. Crystalline Form B of Compound 1 is a metastable desolvate, and is obtained through the desolvation of crystalline Form C Methanolate upon overnight exposure to 80° C. Crystalline Form E of Compound 1 is a metastable anhydrate and was most frequently observed through the disproportionation of various salts of Compound 1 in water. Crystalline Form F of Compound 1 is a hydrate, and was generated by slurrying the HCl salt of Compound 1, in water. It is probable that the hydrate results from the displacement of $Cl^-$ from the crystal structure, which is unlikely to occur without the HCl salt as an intermediate. The hydrate was shown to remain unchanged for 5 days under vacuum at ambient temperature but does dehydrate with concomitant decomposition upon exposure to 100° C. Characterization data are discussed in more detail below.

Anhydrous Forms

Form A, Stable Anhydrate

Crystalline Form A is an anhydrate of Compound 1 with a decomposition onset of 207° C. (FIG. 3A and FIG. 3B). Form A is the most thermodynamically stable, relative to the other anhydrous forms, at ambient temperature (see Example 4).

Form A was routinely observed from various solvents and can be generated through slurries in solvents with adequate solubility, evaporations, cooling of saturated solutions, and solvent/anti-solvent additions (see Table 1). For example, dissolving Compound 1 in dichloromethane (DCM) followed by either flash evaporation at 80° C. or under $N_2$ led to the isolation of Form A of Compound 1. Further seeding the DCM solution with Form E of Compound 1, followed by fast evaporation under $N_2$ also resulted in the isolation of pure Form A of Compound 1. Various other experiments in dimethylformamide (DMF), tetrahydrofuran (THF), Ethanol (EtOH), and water/DMF mixtures also lead to the isolation of pure Form A of Compound 1.

The XRPD pattern and the peak list for Form A of compound 1 is illustrated in FIG. 5 (experimental, top) and Table 2, respectively.

TABLE 2

| Observed peaks for Form A of Compound 1. | | |
|---|---|---|
| °2θ | d space (Å) | Intensity (%) |
| 3.02 ± 0.20 | 29.232 ± 1.935 | 100 |
| 9.10 ± 0.20 | 9.710 ± 0.213 | 71 |
| 10.74 ± 0.20 | 8.231 ± 0.153 | 43 |
| 11.95 ± 0.20 | 7.400 ± 0.123 | 10 |
| 12.16 ± 0.20 | 7.273 ± 0.119 | 15 |
| 13.79 ± 0.20 | 6.416 ± 0.093 | 32 |
| 15.22 ± 0.20 | 5.817 ± 0.076 | 12 |
| 15.93 ± 0.20 | 5.559 ± 0.069 | 8 |
| 18.46 ± 0.20 | 4.802 ± 0.052 | 4 |
| 20.74 ± 0.20 | 4.279 ± 0.041 | 11 |
| 20.97 ± 0.20 | 4.233 ± 0.040 | 30 |
| 21.36 ± 0.20 | 4.156 ± 0.038 | 6 |
| 21.62 ± 0.20 | 4.107 ± 0.038 | 11 |
| 22.04 ± 0.20 | 4.030 ± 0.036 | 33 |
| 22.66 ± 0.20 | 3.921 ± 0.034 | 16 |
| 23.06 ± 0.20 | 3.854 ± 0.033 | 27 |
| 23.86 ± 0.20 | 3.726 ± 0.031 | 29 |
| 24.40 ± 0.20 | 3.645 ± 0.029 | 59 |
| 25.03 ± 0.20 | 3.555 ± 0.028 | 10 |
| 25.55 ± 0.20 | 3.484 ± 0.027 | 16 |

TABLE 2-continued

| Observed peaks for Form A of Compound 1. | | |
|---|---|---|
| °2θ | d space (Å) | Intensity (%) |
| 26.51 ± 0.20 | 3.360 ± 0.025 | 11 |
| 27.07 ± 0.20 | 3.291 ± 0.024 | 28 |
| 27.43 ± 0.20 | 3.249 ± 0.023 | 19 |
| 27.85 ± 0.20 | 3.201 ± 0.023 | 7 |
| 28.29 ± 0.20 | 3.152 ± 0.022 | 5 |

TABLE 2-continued

| Observed peaks for Form A of Compound 1. | | |
|---|---|---|
| °2θ | d space (Å) | Intensity (%) |
| 29.09 ± 0.20 | 3.067 ± 0.021 | 11 |
| 29.52 ± 0.20 | 3.023 ± 0.020 | 6 |
| 30.44 ± 0.20 | 2.934 ± 0.019 | 5 |
| 30.76 ± 0.20 | 2.904 ± 0.018 | 4 |

Figure 4:
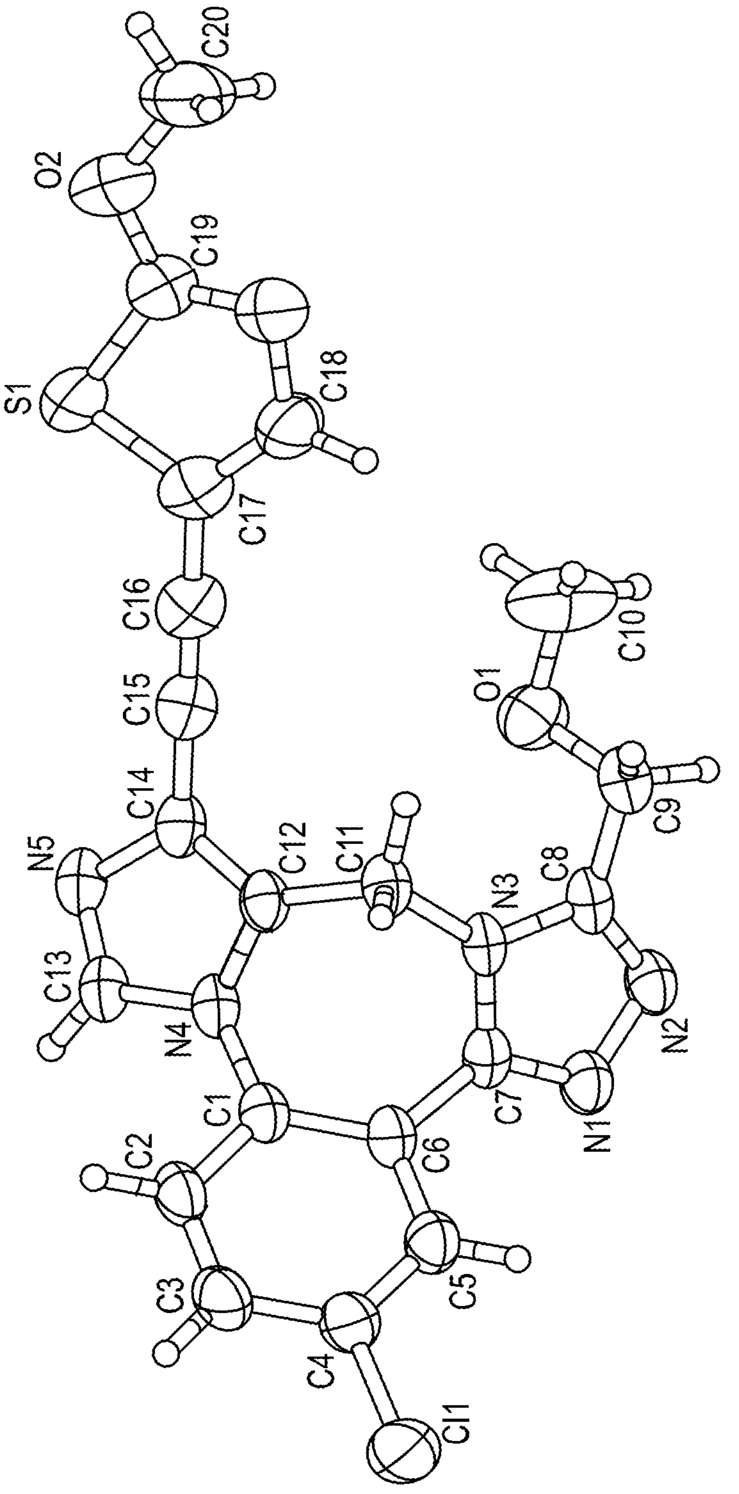
FIG. 4 depicts the atomic displacement ellipsoid diagram of anhydrous Form A. Non-hydrogen atoms are represented by 50% probability anisotropic thermal ellipsoids.

The single-crystal structure of Form A was determined (FIG. 4). Single crystals suitable for X-ray diffraction of Form A were obtained by dissolving Compound 1 in dimethylformamide, filtering the solution into ethanol, and cooling the mixture in a refrigerator (4C) for a period of 3 days to induce crystallization of Form A. The crystal system is monoclinic and the space group is C2/c. The cell parameters and calculated volume are: a=58.1415(14) Å, b=4.03974(8) Å, c=17.1204(3) Å, α=90, β=90.261(2)°, γ=90°, V=4021.15(14) $Å^3$. The molecular weight is 438.89 g $mol^{-1}$ with Z=8, resulting in a calculated density of 1.450 g $cm^{-3}$. Further details of the crystal data and crystallographic data collection parameters are summarized in Table 3. The asymmetric unit contains one Compound 1 molecule. The thiazole and ether are rotated by 1800, refining to 88% occupancy in the predominant orientation. An atomic displacement ellipsoid drawing of Compound 1 Form A in the predominant orientation is shown in FIG. 4. The calculated XRPD pattern, from the single crystal data, is compared to the experimental pattern in FIG. 5.

TABLE 3

| Crystal Data and Data Collection Parameters for Form A. | |
|---|---|
| Empirical formula | $C_{20}H_{15}ClN_6O_2S$ |
| Formula weight (g $mol^{-1}$) | 438.89 |
| Temperature (K) | 293(9) |
| Wavelength (Å) | 1.54184 |
| Crystal system | monoclinic |
| Space group | C2/c |
| Unit cell parameters | |
| a = 58.1415(14) Å | α = 90° |
| b = 4.03974(8) Å | β = 90.261(2)° |
| c = 17.1204(3) Å | γ = 90° |
| Unit cell volume ($Å^3$) | 4021.15(14) |
| Cell formula units, Z | 8 |
| Calculated density (g $cm^{-3}$) | 1.450 |
| Absorption coefficient ($mm^{-1}$) | 2.917 |
| F(000) | 1808 |
| Crystal size ($mm^3$) | 0.38 × 0.04 × 0.02 |
| Reflections used for cell measurement | 6912 |
| θ range for cell measurement | 5.1510°-76.6050° |
| Total reflections collected | 9098 |
| Index ranges | −53 ≤ h ≤ 71; −4 ≤ k ≤ 4; −21 ≤ l ≤ 21 |
| θ range for data collection | $θ_{min}$ = 4.563°, $θ_{max}$ = 77.412° |
| Completeness to $θ_{max}$ | 95% |
| Completeness to $θ_{full}$ = 67.684° | 99.8% |
| Absorption correction | multi-scan |
| Transmission coefficient range | 0.681-1.000 |
| Refinement method | full matrix least-squares on $F^2$ |
| Independent reflections | 4047 [$R_{int}$ = 0.0225, $R_σ$ = 0.0298] |
| Reflections [I > 2σ(I)] | 3294 |
| Reflections/restraints/parameters | 4047/7/299 |
| Goodness-of-fit on $F^2$ | S = 1.03 |
| Final residuals [I > 2σ(I)] | R = 0.0381, $R_w$ = 0.1057 |
| Final residuals [all reflections] | R = 0.0471, $R_w$ = 0.1125 |
| Largest diff. peak and hole (e $Å^{-3}$) | 0.247, −0.281 |
| Max/mean shift/standard uncertainty | 0.001/0.000 |

Thermograms of Form A are shown in FIG. 3A and FIG. 3B. The TGA does not show weight loss up to 207° C., consistent with an anhydrous form. The DSC curve exhibits an exotherm, due to decomposition, with an onset at about 207° C.

Figure 6:
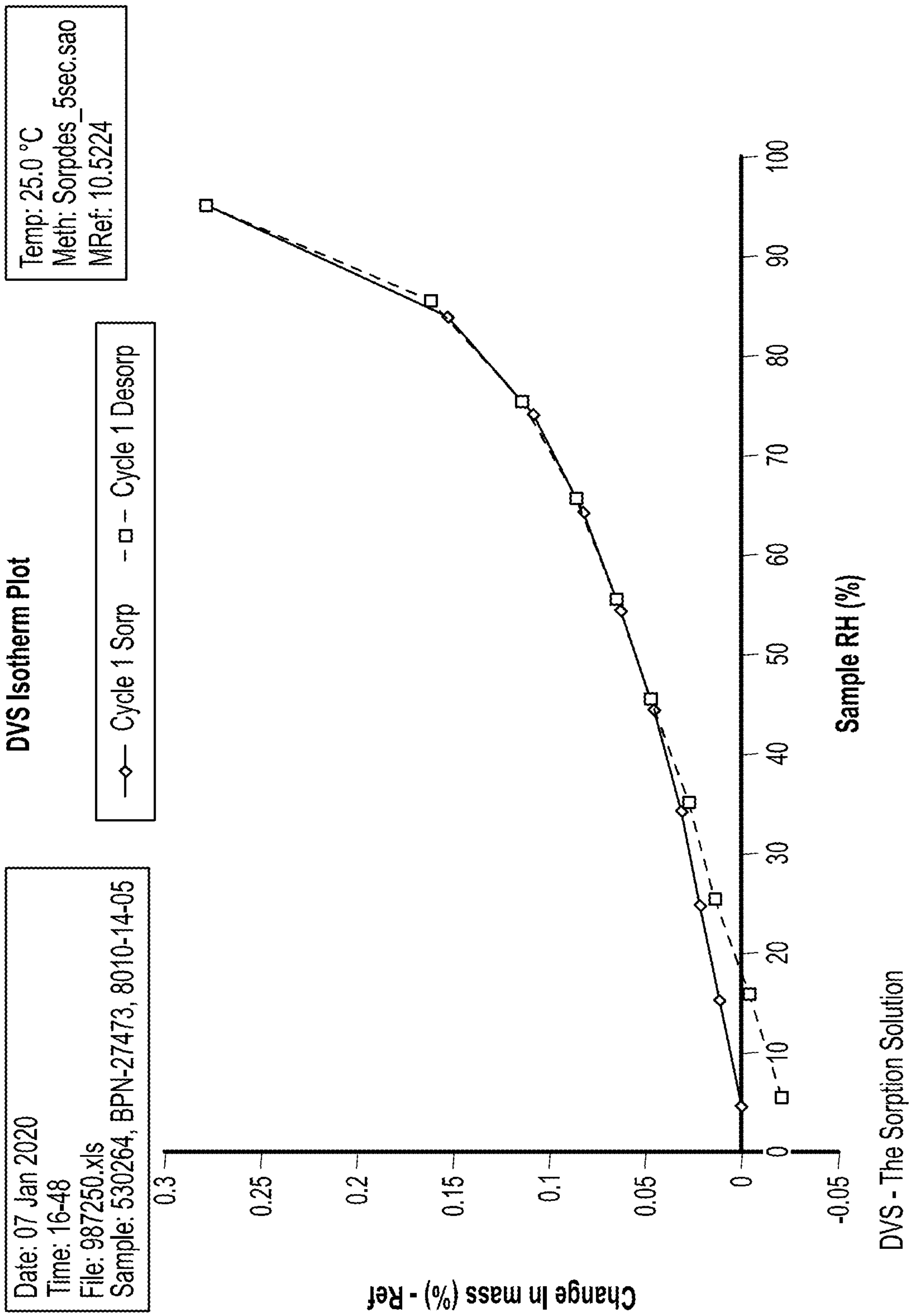
FIG. 6 depicts the dynamic vapor sorption isotherm of anhydrous Form A.

The dynamic vapor sorption (DVS) isotherm suggests that Form A exhibits low hygroscopicity (FIG. 6). Hygroscopicity can be described as low, limited, or significant in part on concepts presented in reference (see Dynamic Vapor Absorption Experimental). The weight change through the sorption/desorption cycle was negligible at ~0.3% with no hysteresis. The material recovered from the DVS experiment was identified as the same as the starting material by XRPD.

Form B, Metastable Desolvate

Form B is a metastable anhydrate of Compound 1 obtained through the desolvation of polymorphic Form C Methanolate of Compound 1 upon overnight exposure to 80°

C. Based on the thermograms for Form C, the desolvated form (Form B) exhibits a decomposition onset at about 190° C. Form B was shown to convert to Form A in solvent-mediated experiments at ambient temperature (see Example 4), confirming that Form B is metastable relative to Form A at that condition.

The XRPD pattern and its peak list for Form B of compound 1 are illustrated in FIG. 7 and Table 4, respectively. The XRPD pattern of Form B was successfully indexed and provides a robust description of the crystalline form through tentative crystallographic unit cell parameters and strong evidence that the pattern is representative of a single crystalline phase (FIG. 7). The form has a monoclinic unit cell likely containing four Compound 1 molecules. Consequently, the formula unit volume of 497 Å$^3$ calculated from the indexing results would be consistent with an anhydrous form.

TABLE 4

Observed peaks for Form B of compound 1.

| °2θ | d space (Å) | Intensity (%) |
|---|---|---|
| 5.09 ± 0.20 | 17.347 ± 0.681 | 5 |
| 6.99 ± 0.20 | 12.636 ± 0.361 | 47 |
| 9.34 ± 0.20 | 9.461 ± 0.202 | 39 |
| 10.23 ± 0.20 | 8.640 ± 0.168 | 46 |
| 10.40 ± 0.20 | 8.499 ± 0.163 | 41 |
| 12.48 ± 0.20 | 7.087 ± 0.113 | 58 |
| 12.97 ± 0.20 | 6.820 ± 0.105 | 30 |
| 13.62 ± 0.20 | 6.496 ± 0.095 | 35 |
| 14.01 ± 0.20 | 6.316 ± 0.090 | 32 |
| 15.28 ± 0.20 | 5.794 ± 0.075 | 47 |
| 17.03 ± 0.20 | 5.202 ± 0.061 | 5 |
| 18.38 ± 0.20 | 4.823 ± 0.052 | 16 |
| 18.76 ± 0.20 | 4.726 ± 0.050 | 9 |
| 19.23 ± 0.20 | 4.612 ± 0.048 | 3 |
| 19.68 ± 0.20 | 4.507 ± 0.045 | 3 |
| 20.57 ± 0.20 | 4.314 ± 0.041 | 23 |
| 20.92 ± 0.20 | 4.243 ± 0.040 | 15 |
| 21.98 ± 0.20 | 4.041 ± 0.036 | 81 |
| 22.54 ± 0.20 | 3.941 ± 0.035 | 9 |
| 22.92 ± 0.20 | 3.877 ± 0.033 | 39 |
| 23.29 ± 0.20 | 3.816 ± 0.032 | 22 |
| 23.60 ± 0.20 | 3.767 ± 0.031 | 81 |
| 24.31 ± 0.20 | 3.658 ± 0.030 | 23 |
| 24.78 ± 0.20 | 3.590 ± 0.029 | 12 |
| 25.11 ± 0.20 | 3.544 ± 0.028 | 12 |
| 25.60 ± 0.20 | 3.477 ± 0.027 | 23 |
| 25.94 ± 0.20 | 3.432 ± 0.026 | 18 |
| 27.28 ± 0.20 | 3.266 ± 0.023 | 100 |
| 28.07 ± 0.20 | 3.176 ± 0.022 | 30 |
| 28.52 ± 0.20 | 3.127 ± 0.021 | 9 |
| 29.09 ± 0.20 | 3.067 ± 0.021 | 7 |
| 30.17 ± 0.20 | 2.960 ± 0.019 | 12 |
| 31.07 ± 0.20 | 2.876 ± 0.018 | 10 |

Material D, Metastable Anhydrate

Figure 8:
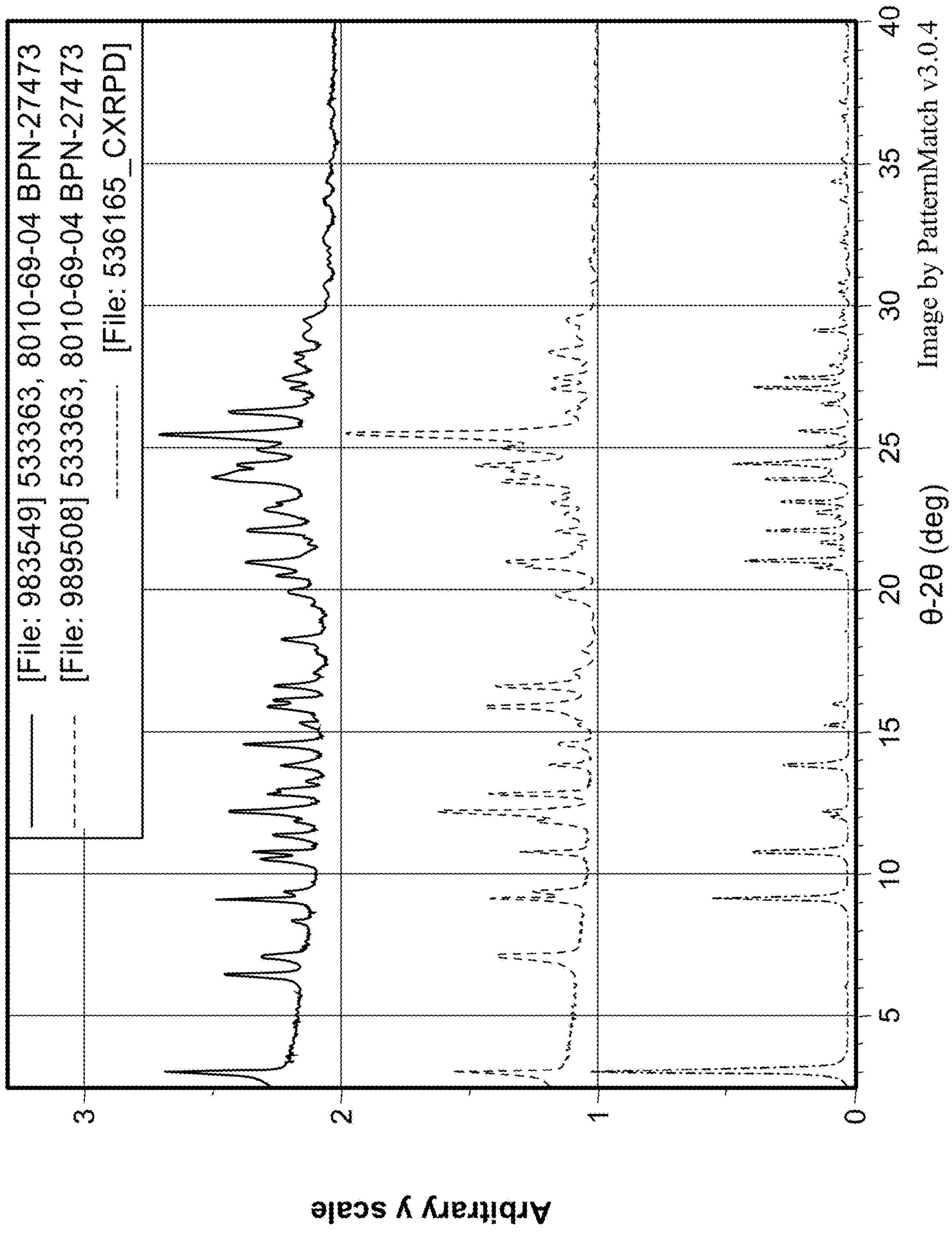
FIG. 8 is an XRPD overlay of Material D taken initially after preparation (top) and after 7 weeks at ambient storage (middle). The XRPD pattern of Form A is provided as a reference (bottom).

Material D of Compound 1 is tentatively identified as an anhydrate. Material D was only obtained as a mixture with Form A (and additional unidentified peaks) from failed attempts to isolate amorphous Compound 1 through rotary evaporations out of DCM. Although the additional unidentified peaks in the XRPD diffractogram were no longer evident after 7 weeks of ambient storage, Material D still remained (FIG. 8). This implies that Material D exhibits some kinetic stability at ambient temperature. Regardless, Material D was shown to convert to Form A in solvent-mediated experiments at ambient temperature (see Example 4), confirming that Material D is metastable relative to Form A at that condition.

Figure 9A:
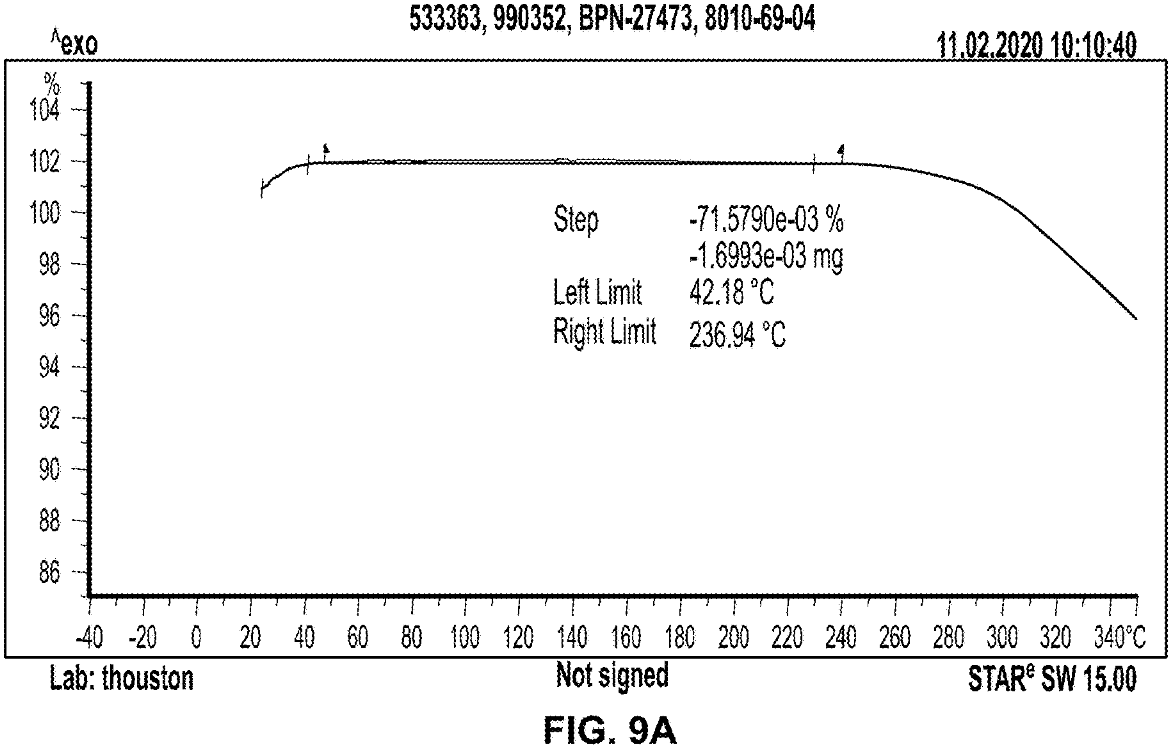
FIGS. 9A and 9B depict the thermograms of Material D (as a mixture with Form A).
Figure 9B:
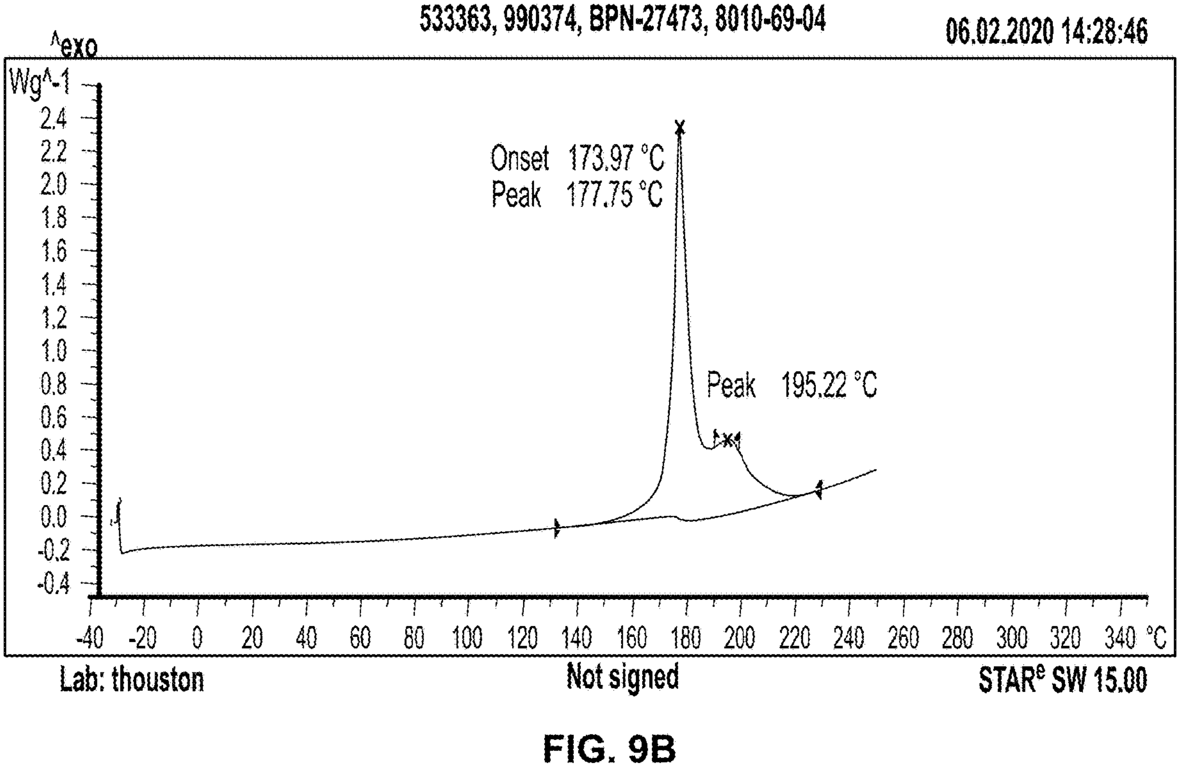

Thermograms of Material D (as a mixture with Form A) are shown in FIG. 9A and FIG. 9B. The TGA does not show weight loss up to 237° C., consistent with a mixture of anhydrous forms. The DSC exhibits exotherms, due to decomposition, with an onset near 174° C.

Form E, Metastable Anhydrate

Form E is an anhydrate of Compound 1 with a decomposition onset of 201° C. (FIG. 12*a* and FIG. 12 B). Form E is metastable relative to Form A; the relative thermodynamic relationship was confirmed with interconversion slurry experiments performed at ambient temperature, 55° C., and 77° C. (see Example 4). Form E was most frequently observed through the disproportionation of various salts of Compound 1 in water. A crystal suitable for single crystal x-ray diffraction was obtained by slowly cooling a THF solution saturated with amorphous Compound 1.

The XRPD pattern and the peak list for Form E of compound 1 is illustrated in FIG. 11 (experimental, top) and Table 5 respectively.

TABLE 5

Observed peaks for Form E of compound 1.

| °2θ | d space (Å) | Intensity (%) |
|---|---|---|
| 7.24 ± 0.20 | 12.198 ± 0.336 | 65 |
| 7.49 ± 0.20 | 11.788 ± 0.314 | 27 |
| 8.48 ± 0.20 | 10.413 ± 0.245 | 14 |
| 9.73 ± 0.20 | 9.079 ± 0.186 | 17 |
| 10.71 ± 0.20 | 8.255 ± 0.154 | 5 |
| 11.40 ± 0.20 | 7.757 ± 0.136 | 50 |
| 11.57 ± 0.20 | 7.640 ± 0.132 | 16 |
| 12.43 ± 0.20 | 7.116 ± 0.114 | 16 |
| 13.00 ± 0.20 | 6.806 ± 0.104 | 8 |
| 13.13 ± 0.20 | 6.738 ± 0.102 | 9 |
| 13.61 ± 0.20 | 6.500 ± 0.095 | 18 |
| 14.32 ± 0.20 | 6.181 ± 0.086 | 3 |
| 14.53 ± 0.20 | 6.092 ± 0.083 | 4 |
| 15.04 ± 0.20 | 5.885 ± 0.078 | 10 |
| 15.27 ± 0.20 | 5.797 ± 0.075 | 4 |
| 15.74 ± 0.20 | 5.624 ± 0.071 | 45 |
| 16.30 ± 0.20 | 5.435 ± 0.066 | 20 |
| 16.82 ± 0.20 | 5.268 ± 0.062 | 13 |
| 17.05 ± 0.20 | 5.197 ± 0.061 | 38 |
| 17.44 ± 0.20 | 5.080 ± 0.058 | 23 |
| 18.07 ± 0.20 | 4.906 ± 0.054 | 58 |
| 18.53 ± 0.20 | 4.784 ± 0.051 | 9 |
| 19.03 ± 0.20 | 4.660 ± 0.049 | 51 |
| 19.19 ± 0.20 | 4.621 ± 0.048 | 39 |
| 19.51 ± 0.20 | 4.546 ± 0.046 | 10 |
| 19.85 ± 0.20 | 4.469 ± 0.045 | 11 |
| 20.09 ± 0.20 | 4.416 ± 0.044 | 21 |
| 21.01 ± 0.20 | 4.225 ± 0.040 | 22 |
| 21.54 ± 0.20 | 4.122 ± 0.038 | 42 |
| 21.62 ± 0.20 | 4.106 ± 0.038 | 44 |
| 22.01 ± 0.20 | 4.035 ± 0.036 | 86 |
| 22.64 ± 0.20 | 3.924 ± 0.034 | 16 |
| 22.92 ± 0.20 | 3.877 ± 0.033 | 100 |
| 23.29 ± 0.20 | 3.816 ± 0.032 | 10 |
| 24.18 ± 0.20 | 3.678 ± 0.030 | 36 |
| 25.04 ± 0.20 | 3.554 ± 0.028 | 33 |
| 25.33 ± 0.20 | 3.513 ± 0.027 | 17 |
| 25.69 ± 0.20 | 3.465 ± 0.027 | 14 |
| 25.93 ± 0.20 | 3.434 ± 0.026 | 9 |
| 26.21 ± 0.20 | 3.397 ± 0.025 | 12 |
| 26.64 ± 0.20 | 3.344 ± 0.025 | 51 |
| 26.93 ± 0.20 | 3.309 ± 0.024 | 24 |
| 27.24 ± 0.20 | 3.271 ± 0.024 | 12 |
| 27.64 ± 0.20 | 3.225 ± 0.023 | 15 |
| 27.97 ± 0.20 | 3.187 ± 0.022 | 10 |
| 28.35 ± 0.20 | 3.145 ± 0.022 | 9 |
| 28.99 ± 0.20 | 3.078 ± 0.021 | 14 |
| 29.37 ± 0.20 | 3.038 ± 0.020 | 11 |
| 30.72 ± 0.20 | 2.908 ± 0.018 | 16 |
| 31.07 ± 0.20 | 2.876 ± 0.018 | 7 |
| 31.57 ± 0.20 | 2.831 ± 0.017 | 17 |

Figure 10:
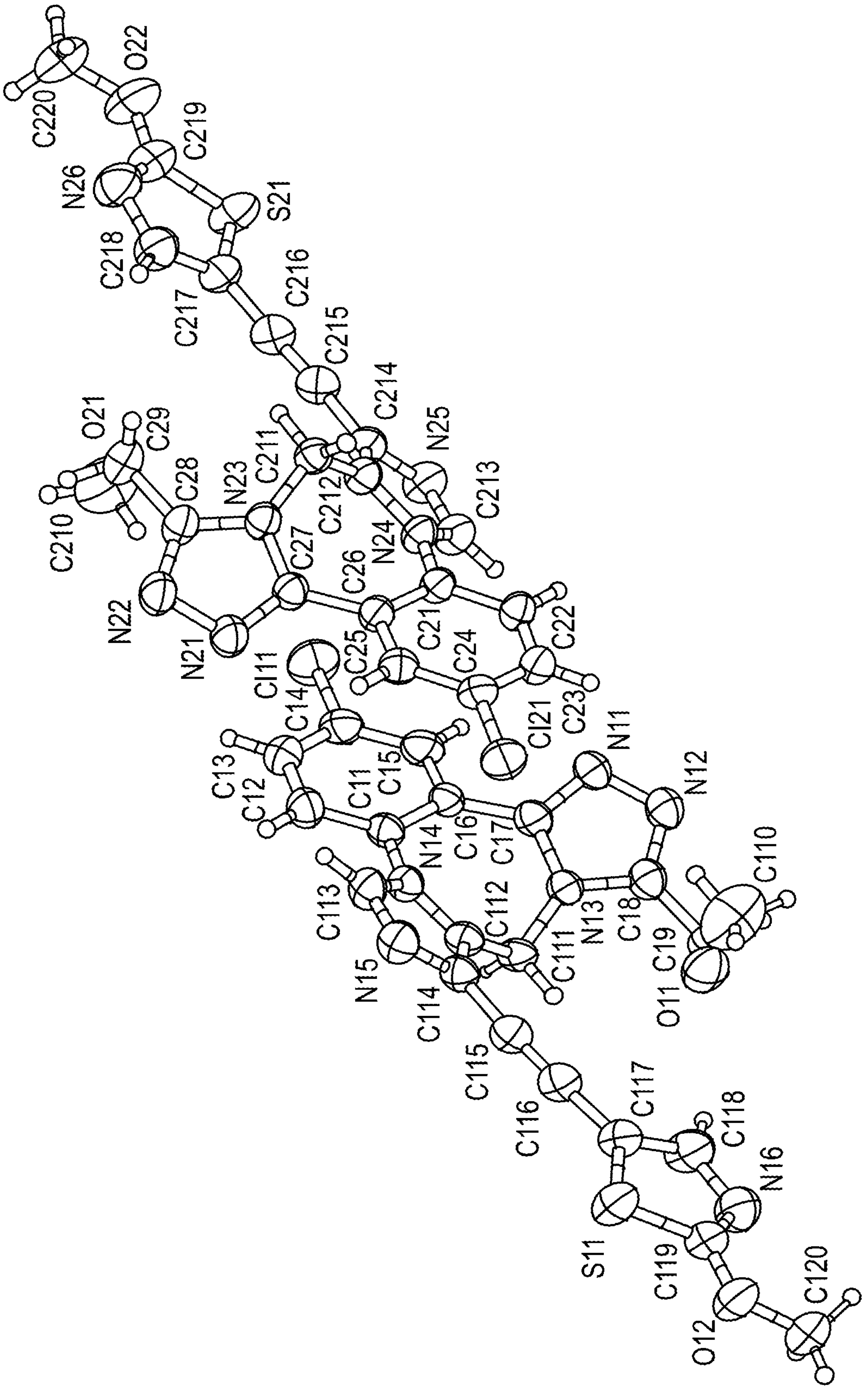
FIG. 10 depicts the atomic displacement ellipsoid diagram of anhydrous Form E. Non-hydrogen atoms are represented by 50% probability anisotropic thermal ellipsoids.

The single-crystal structure of Form E was determined successfully (FIG. 10). The crystal system is monoclinic and the space group is $P2_1/n$. The cell parameters and calculated volume are: a=11.83974(13) Å, b=23.5195(2) Å, c=14.48807(17) Å, α=90°, β=101.5333(11)°, γ=90°, V=3952.96(7) $Å^3$. The molecular weight is 438.89 g $mol^{-1}$ with Z=8, resulting in a calculated density of 1.475 g $cm^{-3}$. Further details of the crystal data and crystallographic data collection parameters are summarized in Table 6. An atomic displacement ellipsoid drawing of Compound 1 Form E is shown in FIG. 10. The asymmetric unit shown contains two Compound 1 molecules. The calculated powder pattern is compared to the experimental pattern in FIG. 11.

TABLE 6

| Crystal Data and Data Collection Parameters for Form E | |
|---|---|
| Empirical formula | $C_{20}H_{15}ClN_6O_2S$ |
| Formula weight (g $mol^{-1}$) | 438.89 |
| Temperature (K) | 299.8(3) |
| Wavelength (Å) | 1.54184 |
| Crystal system | monoclinic |
| Space group | $P2_1/n$ |
| Unit cell parameters | |
| a = 11.83974(13) Å | α = 90° |
| b = 23.5195(2) Å | β = 101.5333(11)° |
| c = 14.48807(17) Å | γ = 90° |
| Unit cell volume ($Å^3$) | 3952.96(7) |
| Cell formula units, Z | 8 |
| Calculated density (g $cm^{-3}$) | 1.475 |
| Absorption coefficient ($mm^{-1}$) | 2.968 |
| F(000) | 1808 |
| Crystal size ($mm^3$) | 0.19 × 0.1 × 0.04 |
| Reflections used for cell measurement | 9088 |
| θ range for cell measurement | 3.6260°-76.9860° |
| Total reflections collected | 21119 |
| Index ranges | −14 ≤ h ≤ 12; −21 ≤ k ≤ 29; −18 ≤ l ≤ 18 |
| θ range for data collection | $θ_{min}$ = 3.637°, $θ_{max}$ = 77.701° |
| Completeness to $θ_{max}$ | 97.4% |
| Completeness to $θ_{full}$ = 67.684° | 100% |
| Absorption correction | multi-scan |
| Transmission coefficient range | 0.888-1.000 |
| Refinement method | full matrix least-squares on $F^2$ |
| Independent reflections | 8184 [$R_{int}$ = 0.0266, $R_σ$ = 0.0339] |
| Reflections [I > 2σ(I)] | 6319 |
| Reflections/restraints/parameters | 8184/0/545 |
| Goodness-of-fit on $F^2$ | S = 1.04 |
| Final residuals [I > 2σ(I)] | R = 0.0427, $R_w$ = 0.1155 |
| Final residuals [all reflections] | R = 0.0572, $R_w$ = 0.1243 |
| Largest diff. peak and hole (e $Å^{-3}$) | 0.315, −0.321 |

Thermograms for Form E are shown in FIG. 12A and FIG. 12B. The TGA does not show weight loss up to ~200° C., consistent with an anhydrous form. The DSC curve exhibits an exotherm, due to decomposition, with an onset near 201° C.

Hydrated Forms

Form F Hydrate

Form F is a likely hydrate of Compound 1. Form F was generated by slurrying the HCl salt of Compound 1 in water (see Example 2 and Table 1). The hydrate was shown to remain unchanged for 5 days under vacuum at ambient temperature but does dehydrate upon exposure to 100° C. Thermal characterization suggests that decomposition occurs immediately upon dehydration at elevated temperatures.

The XRPD patterns of the HCl salt of Compound 1 and Free Base Form F hydrate are similar (FIG. 13), suggesting that the crystal structures are also similar. It is probable that the hydrate results from the displacement of $Cl^-$ from the structure. Multiple attempts to crystallize a hydrated form directly from the free base were unsuccessful-even with seeding with up to 50 wt %. Instead, gels of the free base would remain in aqueous solvent systems at high water activity or would eventually crystallize to Form A at water activities of 0.7 and below. Therefore, it is unlikely that hydrate formation of the free base will occur without the HCl salt as an intermediate.

Figure 14:
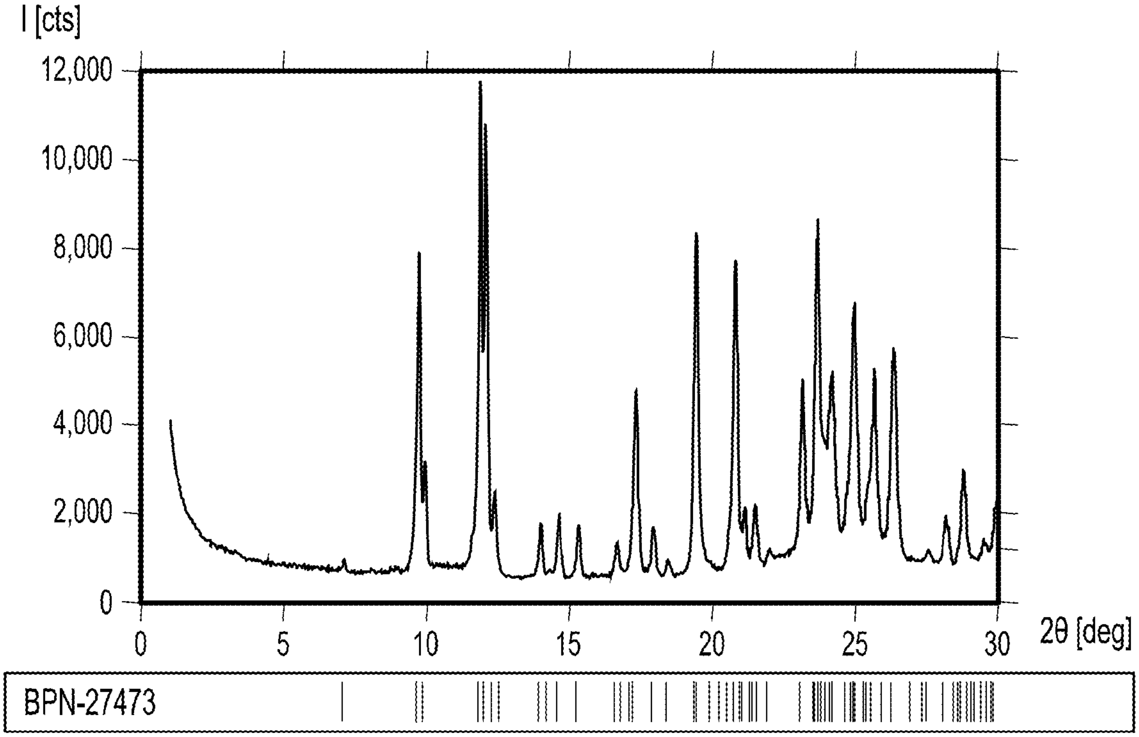
FIG. 14 is the indexed XRPD pattern of monohydrate Form F.

The XRPD pattern and its peak list for Form F of compound 1 are illustrated in FIG. 14 and Table 7, respectively. The XRPD pattern was successfully indexed and provides strong evidence that the pattern is representative of a single crystalline phase (FIG. 14). The form has a triclinic unit cell likely containing two Compound 1 molecules. Consequently, the formula unit volume of 511 $Å^3$ calculated from the indexing results would be consistent with a hydrate that can theoretically accommodate up to one mol/mol of water.

TABLE 7

Observed peaks for Form F of compound 1.

| °2θ | d space (Å) | Intensity (%) |
|---|---|---|
| 7.11 ± 0.20 | 12.423 ± 0.349 | 8 |
| 9.73 ± 0.20 | 9.083 ± 0.186 | 67 |
| 9.93 ± 0.20 | 8.900 ± 0.179 | 27 |
| 11.88 ± 0.20 | 7.443 ± 0.125 | 100 |
| 12.07 ± 0.20 | 7.327 ± 0.121 | 91 |
| 12.37 ± 0.20 | 7.150 ± 0.115 | 21 |
| 13.98 ± 0.20 | 6.330 ± 0.090 | 15 |

TABLE 7-continued

| Observed peaks for Form F of compound 1. | | |
|---|---|---|
| °2θ | d space (Å) | Intensity (%) |
| 14.63 ± 0.20 | 6.050 ± 0.082 | 16 |
| 15.33 ± 0.20 | 5.775 ± 0.075 | 15 |
| 16.67 ± 0.20 | 5.314 ± 0.063 | 11 |
| 17.33 ± 0.20 | 5.113 ± 0.059 | 41 |
| 17.94 ± 0.20 | 4.940 ± 0.055 | 14 |
| 18.46 ± 0.20 | 4.802 ± 0.052 | 8 |
| 19.44 ± 0.20 | 4.562 ± 0.046 | 71 |
| 20.81 ± 0.20 | 4.265 ± 0.041 | 66 |
| 21.13 ± 0.20 | 4.201 ± 0.039 | 18 |
| 21.50 ± 0.20 | 4.130 ± 0.038 | 19 |
| 22.00 ± 0.20 | 4.037 ± 0.036 | 10 |
| 23.16 ± 0.20 | 3.837 ± 0.033 | 43 |
| 23.68 ± 0.20 | 3.754 ± 0.031 | 74 |
| 24.18 ± 0.20 | 3.678 ± 0.030 | 44 |
| 24.97 ± 0.20 | 3.563 ± 0.028 | 58 |
| 25.67 ± 0.20 | 3.468 ± 0.027 | 45 |
| 26.35 ± 0.20 | 3.380 ± 0.025 | 49 |
| 27.55 ± 0.20 | 3.235 ± 0.023 | 10 |
| 28.19 ± 0.20 | 3.163 ± 0.022 | 17 |
| 28.81 ± 0.20 | 3.096 ± 0.021 | 25 |
| 29.53 ± 0.20 | 3.022 ± 0.020 | 12 |
| 30.07 ± 0.20 | 2.969 ± 0.019 | 25 |
| 30.50 ± 0.20 | 2.929 ± 0.019 | 30 |
| 30.93 ± 0.20 | 2.889 ± 0.018 | 13 |
| 31.59 ± 0.20 | 2.830 ± 0.017 | 9 |
| 32.29 ± 0.20 | 2.770 ± 0.017 | 18 |

The solution $^1H$ NMR spectrum is consistent with the chemical structure of Compound 1. Peaks that could be attributed to residual organic solvent are not evident. Although derived from the HCl salt, ion chromatography quantitates a negligible amount of $Cl^-$, confirming that Form F is a crystalline form of the free base.

Figure 15A:
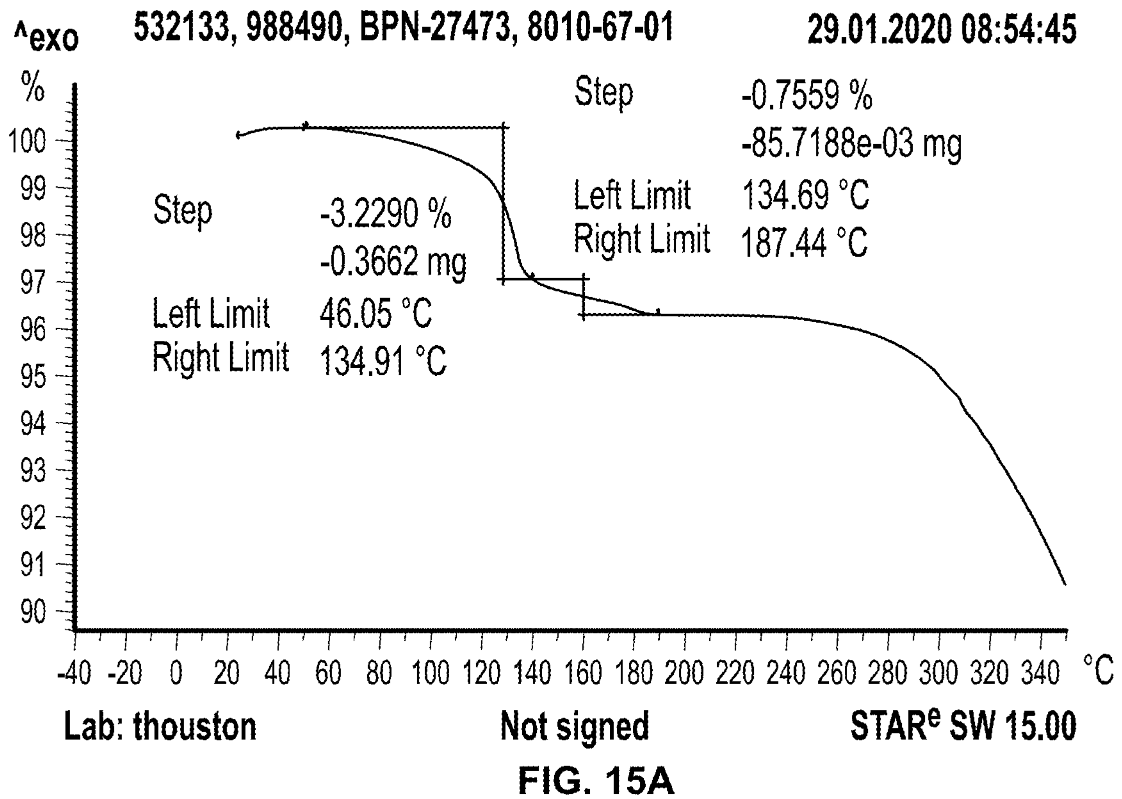
FIGS. 15A and 15B depict the thermograms of monohydrate Form F.
Figure 15B:
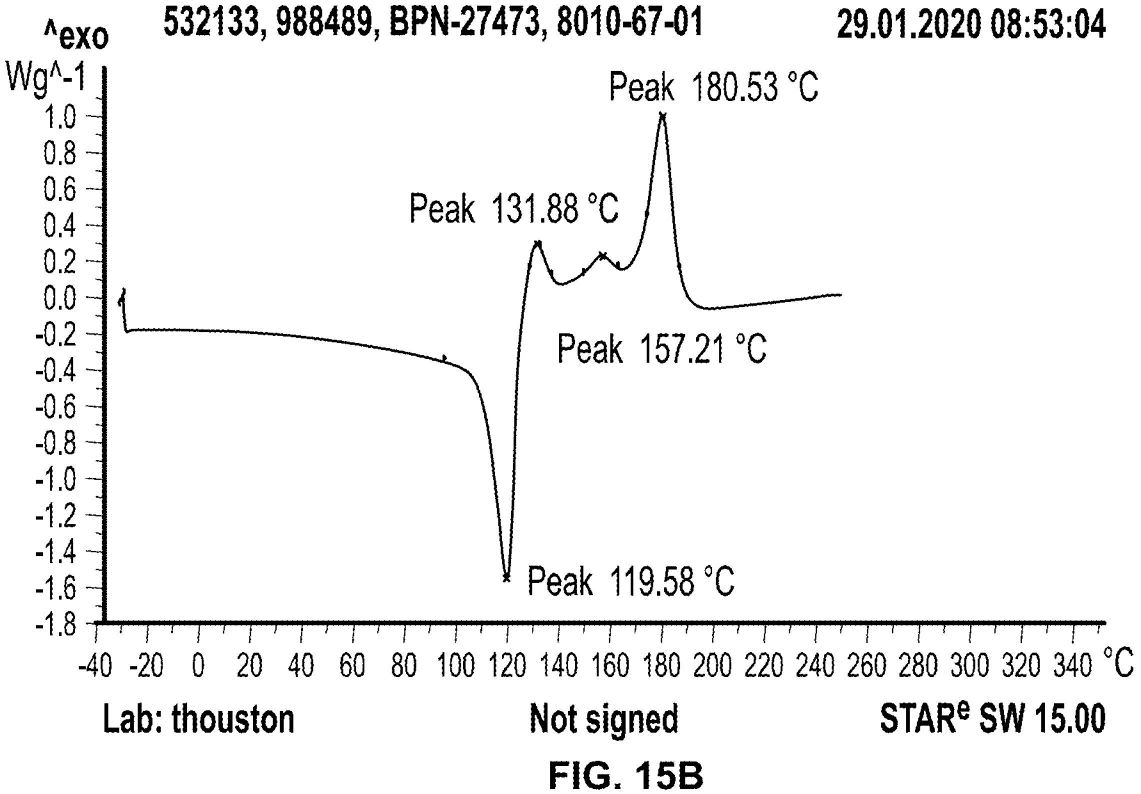

Thermograms for Form F are provided in FIG. 15A and FIG. 15B. The TGA shows an initial 3.2% weight loss up to 135° C. and an additional 0.8% loss from 135 to 187° C. Assuming water is the only volatile (residual organic solvent was not evident in the $^1H$ NMR spectrum, discussed above), the weight loss in the initial step is equivalent to ~0.8 moles of water per mole of Compound 1. The DSC curve exhibits a broad dehydration endotherm that immediately leads into exotherms above 120° C. The DSC exotherms suggest that decomposition occurs immediately upon dehydration. Accordingly, exposing the sample to 100° C. for several minutes resulted in loss of crystallinity by XRPD.

Figure 16:
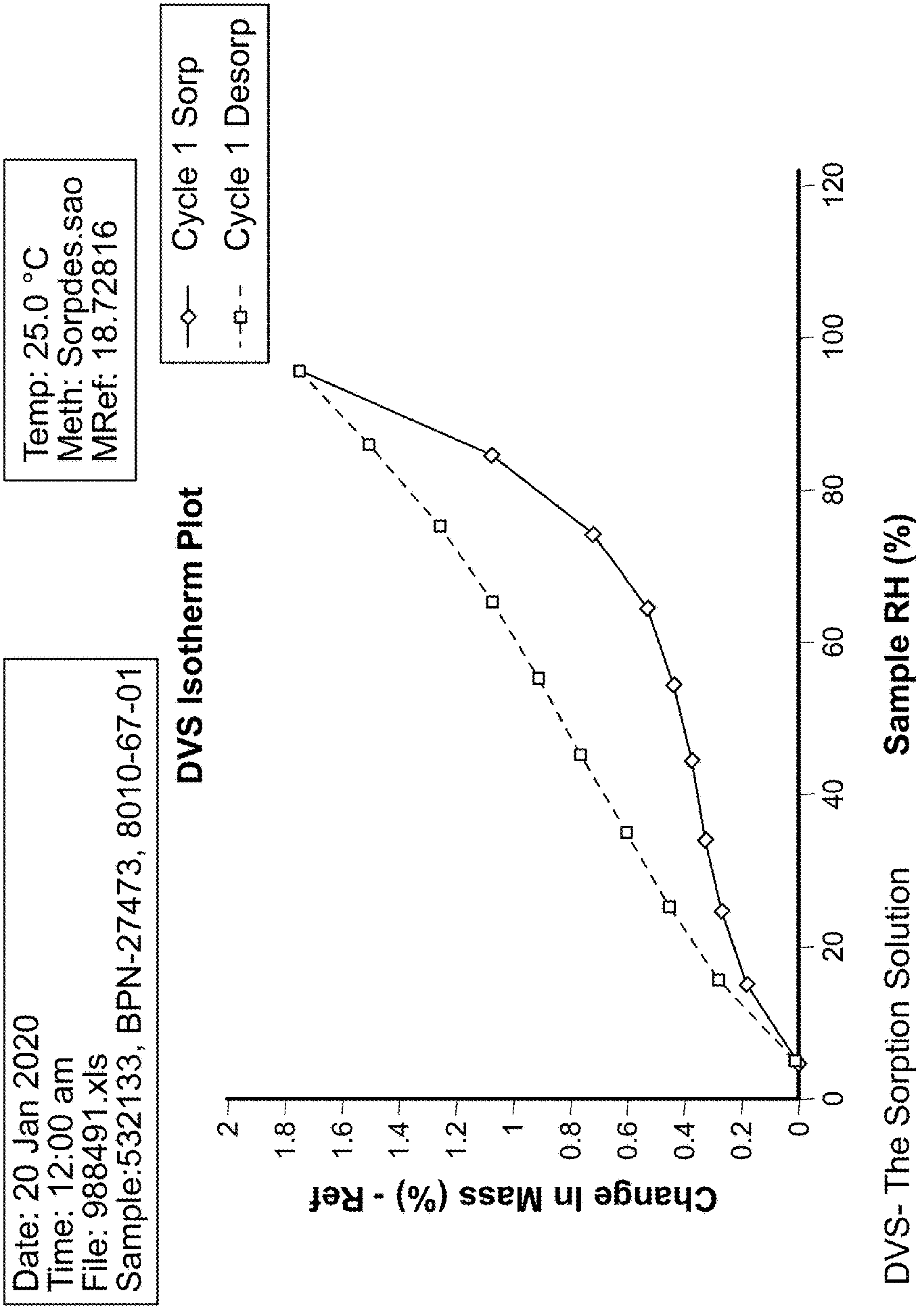
FIG. 16 depicts the dynamic vapor sorption (DVS) isotherm of monohydrate Form F.

The DVS isotherm indicates Form F exhibits limited hygroscopicity (FIG. 16). A 1.8% weight gain from 5-95% RH and a 1.5% weight loss with significant hysteresis upon desorption is observed. The recovered post DVS sample was still Form F by XRPD.

Solvated Forms

Form C Methanolate

Form C is a methanolate observed from experiments involving methanol. In particular, amorphous Compound 1 was slurried in a methanol solution at ambient temperature for 30 minutes under $N_2$. The subsequent removal of the solvent at 60° C. resulted in isolation of Form C (Table 1). The solvate is kinetically stable and was shown to remain unchanged for 9 weeks under ambient conditions. However, the methanolate will desolvate to Form B (see Form B) upon overnight exposure to 80° C.

The XRPD pattern and its peak list for Form F of compound 1 are illustrated in FIG. 17 and Table 8, respectively. The XRPD pattern was successfully indexed and provides strong evidence that the pattern is representative of a single crystalline phase (FIG. 17). The form has a monoclinic unit cell likely containing four Compound 1 molecules. Consequently, the formula unit volume of 544 $Å^3$ calculated from the indexing results would be consistent with a solvate that can theoretically accommodate up to one mol/mol of methanol.

TABLE 8

| Observed peaks for Form C of compound 1. | | |
|---|---|---|
| °2θ | d space (Å) | Intensity (%) |
| 4.71 ± 0.20 | 18.746 ± 0.796 | 6 |
| 7.06 ± 0.20 | 12.511 ± 0.354 | 41 |
| 8.50 ± 0.20 | 10.394 ± 0.244 | 44 |
| 9.41 ± 0.20 | 9.391 ± 0.199 | 65 |
| 10.27 ± 0.20 | 8.606 ± 0.167 | 20 |
| 12.26 ± 0.20 | 7.214 ± 0.117 | 21 |
| 12.49 ± 0.20 | 7.081 ± 0.113 | 62 |
| 14.17 ± 0.20 | 6.245 ± 0.088 | 54 |
| 17.05 ± 0.20 | 5.196 ± 0.061 | 13 |
| 18.92 ± 0.20 | 4.687 ± 0.049 | 49 |
| 19.39 ± 0.20 | 4.574 ± 0.047 | 8 |
| 20.26 ± 0.20 | 4.380 ± 0.043 | 8 |
| 20.65 ± 0.20 | 4.298 ± 0.041 | 47 |
| 21.05 ± 0.20 | 4.217 ± 0.040 | 19 |
| 22.06 ± 0.20 | 4.026 ± 0.036 | 63 |
| 23.19 ± 0.20 | 3.832 ± 0.033 | 35 |
| 23.67 ± 0.20 | 3.756 ± 0.031 | 96 |
| 24.02 ± 0.20 | 3.702 ± 0.030 | 38 |
| 24.35 ± 0.20 | 3.652 ± 0.030 | 20 |
| 24.68 ± 0.20 | 3.604 ± 0.029 | 21 |
| 25.25 ± 0.20 | 3.524 ± 0.027 | 27 |
| 25.73 ± 0.20 | 3.460 ± 0.026 | 16 |
| 26.42 ± 0.20 | 3.371 ± 0.025 | 100 |
| 27.09 ± 0.20 | 3.289 ± 0.024 | 10 |
| 27.70 ± 0.20 | 3.218 ± 0.023 | 31 |
| 28.58 ± 0.20 | 3.121 ± 0.021 | 17 |
| 29.12 ± 0.20 | 3.064 ± 0.021 | 25 |
| 29.52 ± 0.20 | 3.023 ± 0.020 | 17 |
| 30.14 ± 0.20 | 2.963 ± 0.019 | 8 |
| 31.31 ± 0.20 | 2.855 ± 0.018 | 15 |
| 31.80 ± 0.20 | 2.812 ± 0.017 | 7 |

Thermograms for Form C are provided in FIG. 18A and FIG. 18B. The TGA shows 3.2% weight loss up to 196° C. Assuming MeOH is the only volatile, the weight loss is equivalent to 0.5 moles of MeOH per mole of Compound 1. The broad endotherms prior to 60° C. in the DSC are due to desolvation and form conversion to Form B. The exotherm, due to decomposition of the desolvated form, exhibits an onset of 190° C.

Example 4: Relative Thermodynamic Stability

Interconversion experiments were performed to identify the most thermodynamically stable anhydrous form of Compound 1 (Table 9). Interconversion or competitive slurry experiments are a solution mediated process that provides a pathway for the less soluble (more stable) crystal to grow at the expense of the more soluble crystal form. Outside the formation of a solvate or degradation, the resulting more stable polymorph from an interconversion experiment is independent of the solvent used because the more thermodynamically stable polymorph has a lower energy and therefore lower solubility. The choice of solvent affects the kinetics of polymorph conversion and not the thermodynamic relationship between polymorphic forms.

TABLE 9

| Competitive Interconversion Slurry Experiments between Crystalline Forms | | | | |
|---|---|---|---|---|
| Forms | Temp | Solvent (v/v) [11] | Time | Result |
| A + B | RT | DCM | 2 d | A + B |
| | | DCM | 8 d | A + B(minor) |
| | | 90:10 $H_2O$/DMF (0.97 $a_w$) | 6 d | A |
| A + D | RT | DCM | 11 d | A |
| | | EtOH | <1 min | A |
| A + E | RT | DCM | 11 d | A |
| | 55° C. | THF | 1 d | A |
| | | THF | 1 d | A |
| | 77° C. | DMF | 1 d | A disordered |
| | | DMF | 1 d | A |
| A + B + F | RT | 60:40 $H_2O$/DMF (0.78 $a_w$) | 9 d | A |
| | | 07:93 $H_2O$/THF (0.91 $a_w$) | 11 d | A |

Various combinations of Forms B, E, F, and Material D were slurried with Form A at ambient and elevated temperatures (for experiments involving Form E). Different solvent systems were used and included a variety of water activities. Saturated solutions were generated and then added to the mixtures composed of approximately equivalent quantities of the forms. The mixtures were slurried for a particular duration of time and the solids harvested and analyzed by XRPD.

Regardless of the mixtures used, Form A prevailed for each experiment. This suggests that Form A is more thermodynamically stable than Form B and Material D at ambient temperature and more thermodynamically stable than Form E at ambient temperature, 55° C., and 77° C.

CONCLUSIONS

Based on the weakly basic $pK_a$ values of Compound 1, stronger acids were selected for salt formation. Crystalline materials were successfully isolated with all eight strong acids used and at least one representative crystalline sample from purported besylate, HCl, mesylate, napadisylate, napsylate, sulfate, and tosylate salts were isolated.

The Free Base forms of Compound 1, Forms A, B, Material D, and Form E, are anhydrous forms; Form F is a hydrate; and Form C is a methanolate. Form A Anhydrate exhibits limited hygroscopicity, a decomposition onset of 207° C., and appears to be the most thermodynamically stable, relative to the other anhydrous forms. Form B Metastable Desolvate is obtained through the desolvation of Form C Methanolate upon overnight exposure to 80° C. Form E Metastable Anhydrate was most frequently observed through the disproportionation of various salts of Compound 1 in water. Form F Hydrate was generated by slurrying the HCl salt, HCl Form A, in water. Without wishing to be bound by theory, it is probable that the hydrate results from the displacement of $Cl^-$ from the crystal structure, which is unlikely to occur without the HCl salt as an intermediate. The hydrate was shown to remain unchanged for 5 days under vacuum at ambient temperature but does dehydrate with concomitant decomposition upon exposure to 100° C. From these experiments, it was determined that Form A of Compound 1 has superior stability as compared to the other polymorphs studied.

Example 5: Effect of Compound 1 on Aged-Impaired Rats

Subjects

Aged, male Long-Evans rats were obtained at 9 months of age from Charles River Laboratories (Raleigh, N.C.) and housed in a vivarium at The Johns Hopkins University until background behavioral assessment in a water maze at 24 months of age. Young rats obtained from the same source were housed in the same vivarium and were included in the background assessment at 6 months of age but were not used for drug testing in a radial arm maze task. All rats were individually housed at 25° C. and maintained on a 12 h light/dark cycle. Food and water were provided ad libitum unless noted otherwise. The rats were examined for health and pathogen-free status throughout the experiments, as well as necropsies at the time of killing. All procedures were in accordance with NIH guidelines using protocols approved by the Institutional Animal Care and Use Committee at The Johns Hopkins University.

Background Behavioral Assessment

All rats were screened in a standardized assessment of spatial cognition before the commencement of drug studies. The background assessment used a well-established Morris water maze protocol as described in detail elsewhere (Gallagher et al, 1993). Briefly, the rats were trained for 8 days (three trials per day) to locate a camouflaged escape platform that remained at the same location throughout training in a water maze. Every sixth trial consisted of a probe trial (free swim with no escape platform) that served to assess the development of a spatially localized search for the escape platform. During these probe trials, a learning index was generated from the proximity of the rat to the escape platform and was used to define impairment in the aged rats. The learning index is the sum of weighted proximity scores obtained during probe trials, with low scores reflecting a search near the escape platform and high scores reflecting searches farther away from the platform (Gallagher et al, 1993). Cue training (visible escape platform) occurred on the last day of training to test for sensorimotor and motivational factors independent of spatial learning. Aged rats with impaired spatial memory performance (i.e., those with learning index scores outside the young 'normative' range) but successful cued training performance were used for the studies as described below.

1. Acute Treatment with Compound 1 Via PO on Radial Arm Maze

Food-deprived aged rats maintained at approximately 85% free-feeding weights were tested for their hippocampal-dependent memory in a radial arm maze task under varying doses of crude Compound 1 (a $GABA_A$ $\alpha5$ receptor agonist).

The radial arm maze apparatus used consisted of eight equidistant-spaced arms. An elevated maze arm (7 cm width×75 cm length) projected from each facet of an octagonal center platform (30 cm diameter, 51.5 cm height). Clear side walls on the arms were 10 cm high and are angled at 650 to form a trough. A food well (4 cm diameter, 2 cm deep) was located at the distal end of each arm. Froot Loops™ (Kellogg Company) were used as rewards. Blocks constructed of Plexiglas™ (30 cm height×12 cm width) could be positioned to prevent entry to any arm. Numerous extra maze cues surrounding the apparatus were also provided. The rats were initially subjected to pre-training (Chappell et al., 1998). Pre-training consisted of a habituation phase, a training phase on the standard win-shift task and another training phase in which a progressively longer delay was imposed between presentation of a subset of arms designated by the experimenter (five arms available and three arms blocked) and completion of the eight-arm win-shift task (i.e., with all eight arms available).

In the habituation phase, rats were familiarized to the maze for a 10-minute session on several days. In each of these sessions, food rewards were scattered on the maze, initially on the center platform and arms and then progressively confined to the arms. After this habituation phase, a standard training protocol was used, in which a food pellet is located at the end of each arm. Rats received one trial each day. Each daily trial terminates when all eight food pellets have been obtained or when either 16 choices were made or 10 minutes had elapsed. After completion of this training phase, a second training phase was carried out in which the memory demand was increased by imposing a brief delay during the trial. At the beginning of each trial, three arms of the eight-arm maze were blocked. Rats were allowed to obtain food on the five arms to which access was permitted during this initial 'information phase' of the trial. Rats were then removed from the maze for progressively longer delays over days (1 min, 30 min, 60 min, etc), during which time the barriers on the maze were removed, thus allowing access to all eight arms. Rats were then placed back onto the center platform and allowed to obtain the remaining food rewards during this 'retention test' phase of the trial. The identity and configuration of the blocked arms varied across trials.

The number of errors the rats made during the retention test phase was tallied. An error occurred in the trial if the rats entered an arm from which food had already been retrieved in the pre-delay component of the trial, or if it re-visited an arm in the post-delay session that had already been visited. After completion of the pre-training test, rats were tested on the task with different doses of Compound 1 using a 5-hr memory retention delay between the information and the test trial.

The efficacy of Compound 1 was tested using oral gavages (PO), in which the drug was administered 30-40 min before each information trial at a volume of 10 ml/kg. Doses tested were 0, 3, 10, and 30 mg/kg using ascending-descending dose series; that is, the dose series was given first in an ascending order and then repeated in a descending order. Therefore, each dose had two determinations; the average number of errors made from the two determinations for each dose was used for analysis. Each drug test was given every other day with intervening washout days, and the vehicle used to deliver the drug was 20% Tween-80.

Figure 20:
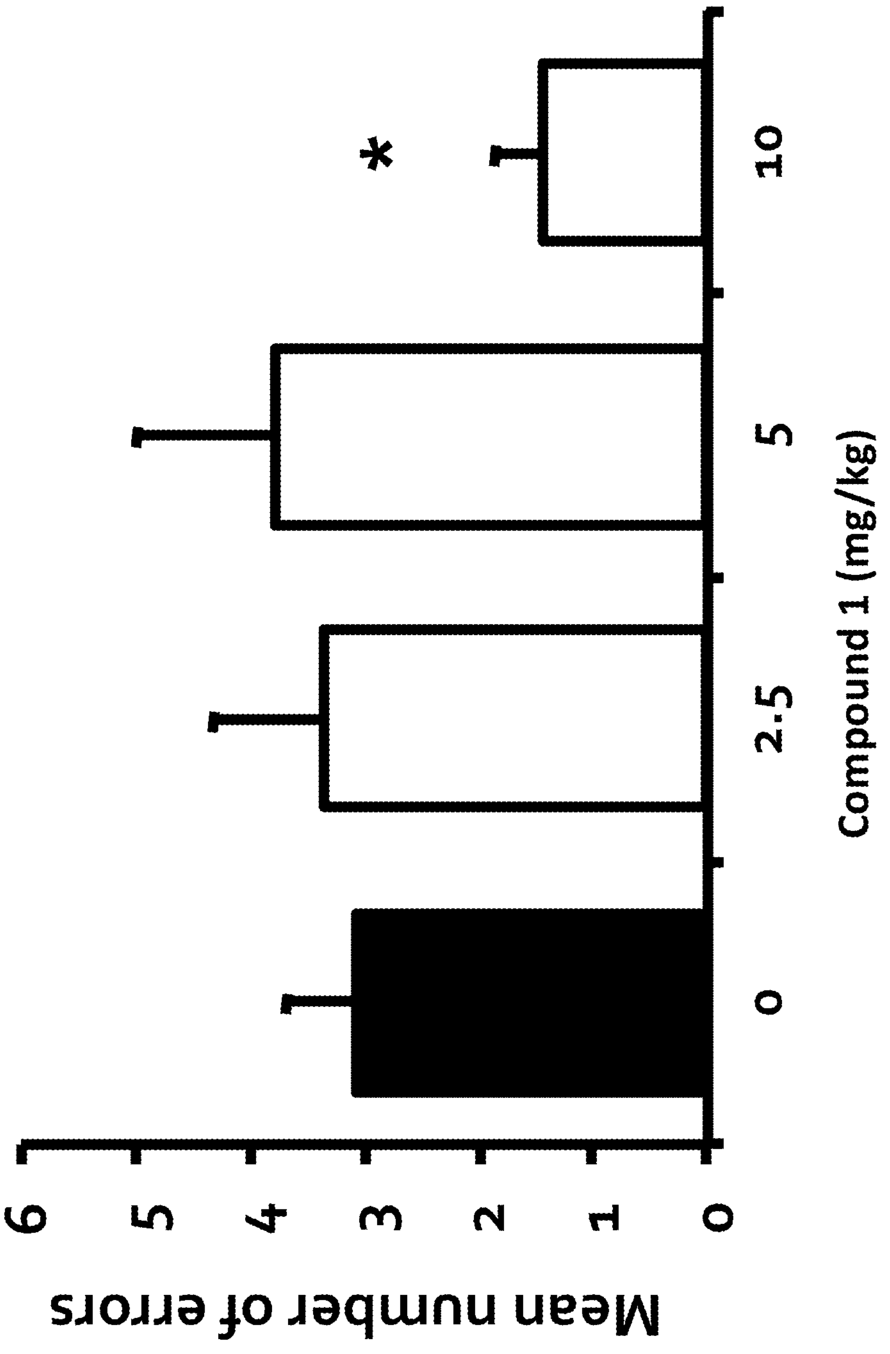
FIG. 20 is a graph showing the effect of Compound 1, as compared to vehicle control in aged-impaired rats using a Radial Arm Maze behavioral task. The graphs show the mean number of errors made by aged-impaired rats treated with varying doses of Compound 1 (2.5 mg/kg, 5 mg/kg, and 10 mg/kg).

The results demonstrate that aged-impaired rats treated with Compound 1 at a dose of 10 mg/kg performed the radial arm maze with fewer errors (FIG. 20). These results indicate that Compound 1 improves the cognition of aged-impaired rats.

2. Acute and Chronic Treatments with Compound 1 on Water Maze

Rats were trained and tested in a novel water maze environment to assess the effect of the treatments. The water maze used here was housed in a different room and was surrounded by curtains with a novel set of patterns relative to the maze used for initial assessment of cognitive status. The training and testing protocol used was identical to the spatial learning-activated protocol described in Haberman et al., (2008, Proceedings of the National Academy of Sciences USA, 105, 10601-10606). The task required rats to swim to a visible escape platform at a fixed location in the presence of spatial cues for 8 training trials with an inter-trial interval of 8 min. An hour after the last training trial, rats were given a probe test in the absence of the escape platform (free swim) to assess the memory of the platform location as measured by time spent searching at the target location.

To assess the acute and chronic effects of Compound 1 treatment, rats received 15-16 days of drug injections with assessment on the water maze on the first day (acute effect) and last day (chronic effect) of treatment. Different surrounding spatial cues and escape location in the water maze were used for the initial and subsequent assessments. Compound 1 was given at 10 mg/kg using intraperitoneal injection (IP) at a volume of 1 ml/kg. On days of water maze assessment, the drug was given 30-40 min before the first training trial. The vehicle used to deliver Compound 1 consisted of 10% N-methyl-2-pyrrolidone (NMP), 45% PEG-400, 11.25% of 2-hydroxypropyl-β-cyclodextrin (HPCD) at 25% concentration, and 33.75% of distilled water.

Figure 21A:
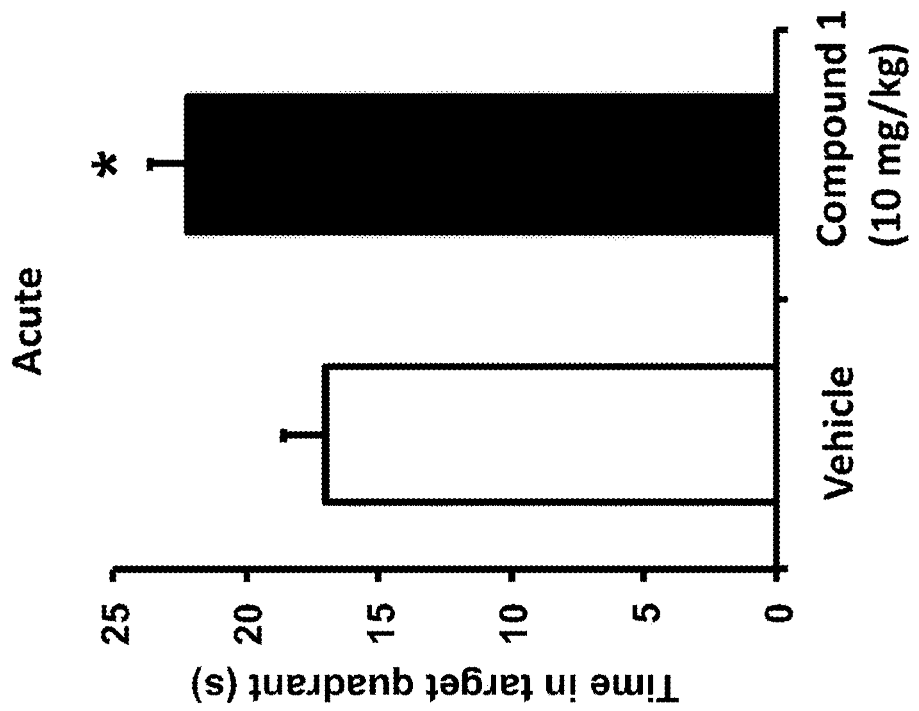
FIGS. 21A and 21B are graphs showing the effect of Compound 1, as compared to vehicle control in aged-impaired rats using a Morris Water Maze behavioral task.
Figure 21B:
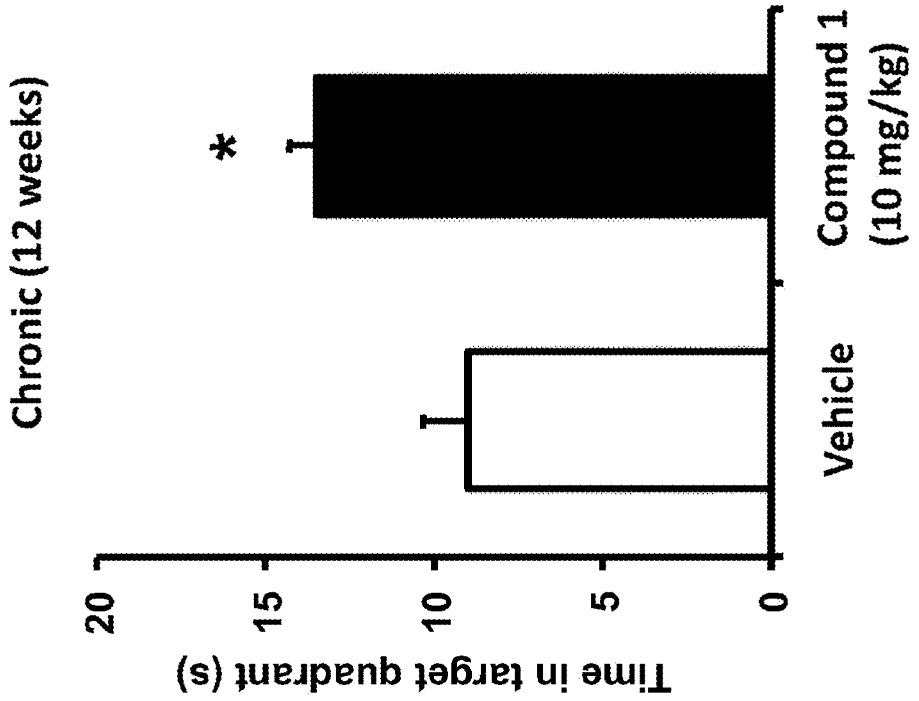

The results demonstrate that rats treated with Compound 1 at a dose of 10 mg/kg spent more time in the target quadrant of the Morris Water Maze (FIG. 21). The results indicate that Compound 1 improves the cognition of aged-impaired rats.

We claim:

1. A crystalline form of a compound having the structure

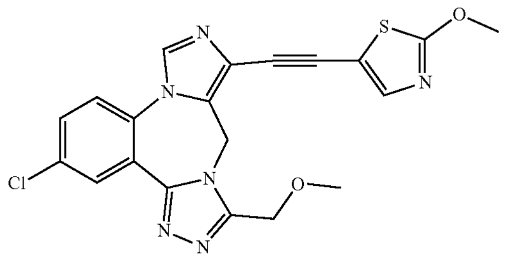 [SMILES: COCc1nnc2n1Cc1c(C#Cc3cnc(OC)s3)ncn1-c1ccc(Cl)cc1-2]

, wherein the crystalline form is Form A, wherein the crystalline Form A is anhydrous and is characterized by one or more of:

(a) an X-ray diffraction pattern (XRPD) comprising at least one peak selected from 3.0 and 21.0 degrees 2θ+0.2 degrees 2θ;

(b) a C2/c single crystal x-ray diffraction space group;

(c) a single crystal x-ray diffraction unit cell having the parameters: a=58.1415 (14) Å, b=4.03974 (8) Å, c=17.1204 (3) Å, a=90°, B=90.261 (2)°, γ=90°, V=4021.15 (14) $Å^3$; and (d) a differential scanning calorimetry (DSC) curve having an exotherm with an onset at about 207° C.

2. A pharmaceutical composition comprising the crystalline Form A of the compound according to claim 1, and a pharmaceutically acceptable carrier, wherein the pharmaceutical composition is formulated in a solid form or a suspension form.

3. A pharmaceutical combination comprising:

a. a first pharmaceutical composition according to claim 2; and b. one or more additional pharmaceutical compositions comprising one or more therapeutic agents selected from the group consisting of an antipsychotic, memantine, an SV2A inhibitor, and an AChEI, or a pharmaceutically acceptable salt, hydrate, solvate, polymorph or prodrug of any of the foregoing.

4. A method of treating cognitive impairment associated with a CNS disorder or cognitive impairment associated with a brain cancer, comprising the step of administering the crystalline Form A of the compound according to claim 1, or administering a pharmaceutical composition comprising that crystalline form, or administering a pharmaceutical combination comprising that crystalline form.

5. The method of claim 4, wherein the CNS disorder is age-related cognitive impairment, Mild Cognitive Impairment (MCI), amnestic Mild Cognitive Impairment (aMCI), dementia, Alzheimer's disease, schizophrenia, amyotrophic lateral sclerosis (ALS), post-traumatic stress disorder (PTSD), mental retardation, Parkinson's disease (PD), autism, compulsive behavior, substance addiction, bipolar disorder, or a disorder associated with cancer therapy.

6. A method of treating a brain cancer or Parkinson's disease psychosis in a subject, comprising the step of administering the crystalline Form A of the compound according to claim 1, or administering a pharmaceutical composition comprising that crystalline form, or administering a pharmaceutical combination comprising that crystalline form.

7. A method of producing the anhydrous crystalline Form A according to claim 1 comprising the steps of:

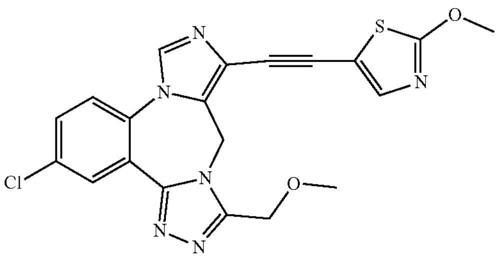

in a. dissolving a compound having the structure dichloromethane to form a solution;

b. evaporating the dichloromethane to produce a precipitate; and c. recovering the precipitate to afford the anhydrous crystalline Form A.

8. A method of producing the anhydrous crystalline Form A according to claim 1 comprising the steps of:

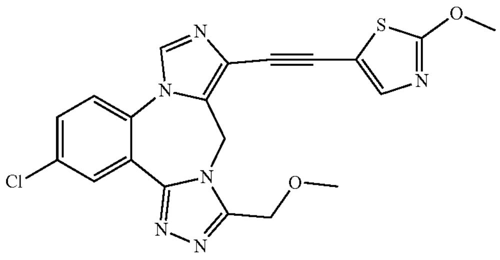 [SMILES: COCc1nnc2n1Cc1c(C#Cc3cnc(OC)s3)ncn1-c1ccc(Cl)cc1-2]

in a first a. dissolving a compound having the structure solvent to produce a solution at a first temperature;

b. adding a second solvent to the solution to form a mixture;

c. optionally cooling the mixture to a second temperature; and d. recovering the resulting precipitate to afford the anhydrous crystalline Form A.

* * * * *